United States Patent
Crew et al.

(10) Patent No.: US 7,741,324 B2
(45) Date of Patent: Jun. 22, 2010

(54) IMIDAZOTRIAZINES AS PROTEIN KINASE INHIBITORS

(75) Inventors: Andrew Philip Crew, Farmingdale, NY (US); Mark Joseph Mulvihill, Farmingdale, NY (US); Douglas Scott Werner, Farmingdale, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 919 days.

(21) Appl. No.: 11/185,599

(22) Filed: Jul. 20, 2005

(65) Prior Publication Data

US 2006/0019957 A1 Jan. 26, 2006

Related U.S. Application Data

(60) Provisional application No. 60/589,514, filed on Jul. 20, 2004.

(51) Int. Cl.
*C07D 487/04* (2006.01)
*C07D 487/12* (2006.01)
*A61K 31/53* (2006.01)
*A61K 35/00* (2006.01)

(52) U.S. Cl. .................................................. 514/243
(58) Field of Classification Search ................ 544/184; 514/243
See application file for complete search history.

(56) References Cited

U.S. PATENT DOCUMENTS

| | | | |
|---|---|---|---|
| 5,217,999 | A | 6/1993 | Levitzki |
| 5,302,606 | A | 4/1994 | Spada |
| 5,397,787 | A | 3/1995 | Buzzetti |
| 5,556,874 | A | 9/1996 | Dobrusin |
| 6,194,439 | B1 | 2/2001 | Dow |
| 6,265,411 | B1 | 7/2001 | Thomas |
| 6,337,338 | B1 | 1/2002 | Kozlowski |
| 6,362,336 | B1 | 3/2002 | Lohmann |
| 6,486,179 | B2 | 11/2002 | Jirousek |
| 6,939,874 | B2 | 9/2005 | Harmange |
| 7,087,602 | B2 | 8/2006 | Thomas |
| 7,115,617 | B2 | 10/2006 | Buchanan |
| 7,202,243 | B2 | 4/2007 | Hendrix |
| 7,244,733 | B2 | 7/2007 | Hunt |
| 7,271,262 | B2 | 9/2007 | La Greca |
| 7,326,699 | B2 | 2/2008 | Capraro |
| 7,332,497 | B2 | 2/2008 | Hirst |
| 7,345,038 | B2 | 3/2008 | Bright |
| 2004/0014774 | A1 | 1/2004 | Myers |
| 2005/0054638 | A1 | 3/2005 | Barlaam |
| 2005/0215564 | A1 | 9/2005 | Stiles |
| 2006/0154982 | A1 | 7/2006 | Larsson |
| 2006/0166992 | A1 | 7/2006 | Hendrix |
| 2006/0235031 | A1* | 10/2006 | Arnold et al. ............ 514/263.2 |
| 2007/0238734 | A1 | 10/2007 | Nemecek |

FOREIGN PATENT DOCUMENTS

| | | |
|---|---|---|
| JP | 07133280 | 5/1995 |
| WO | WO 97/28161 | 8/1997 |
| WO | WO 01/72751 | 10/2001 |
| WO | WO-2005097800 | * 10/2005 |

OTHER PUBLICATIONS

Mass, R. D., Int. J. Radiation Oncology Bio. Phys. vol. 58(3): 932-940, 2004.*
Fabbro et al. Pharmacology & therapeutics 93, 79-98, 2002.*
Cecil Textbook of Medicine, edited by Bennet, J.C., and Plum F., 20th edition, vol. 1, 1004-1010, 1996.*
Snyder et al., J. Med. Liban 48(4): 208-214, 2000.*
Turner et al., Current Pharmaceutical Design. 2, 209-224, 1996.*
Sugar et al., Diagn. Microbiol. Infect. Dis. 21: 129-133, 1995.*
Albert, A. et al. (1970) Journal of the Chemical Society, vol. 11, pp. 1540-1547.
Albert, A. et al. (1969) Chem. Biol.Pterdines.Proc.Int.Symp., 4th, 4:1-5.
Baserga R. (1999) Exp.Cell.Res, vol. 253, pp. 1-6.
Parrizas et al (1997) Endocrinology, vol. 138, pp. 1427-1433.
(1998) Expert Opinion Ther. Pat., vol. 8, pp. 475-478.
International Search Report in PCT/US2005/025891.
International Preliminary Report on Patentability in PCT/US2005/025891.
Written Opinion of the International Search Authority in PCT/US2005/025891.
Machine English Translation of JP 07133280.

* cited by examiner

Primary Examiner—Venkataraman Balasubramanian

(57) ABSTRACT

Compounds of the formula

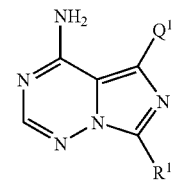

and pharmaceuticaly acceptable salts thereof, wherein $Q^1$ and $R^1$ are defined herein, inhibit the IGF-1R enzyme and are useful for the treatment and/or prevention of various diseases and conditions that respond to treatment by inhibition of tyrosine kinases.

12 Claims, No Drawings

IMIDAZOTRIAZINES AS PROTEIN KINASE INHIBITORS

This application claims the benefit of U.S. Provisional Application No. 60/589,514, filed Jul. 20, 2004.

BACKGROUND OF THE INVENTION

The present invention is directed to novel imidazotriazine compounds, their salts, and compositions comprising them. In particular, the present invention is directed to novel imidazotriazine compounds that inhibit the activity of tyrosine kinase enzymes in animals, including humans, for the treatment and/or prevention of various diseases and conditions such as cancer.

Protein tyrosine kinases (PTKs) are enzymes that catalyse the phosphorylation of specific tyrosine residues in various cellular proteins involved in regulation of cell proliferation, activation, or differentiation (Schlessinger and Ullrich, 1992, Neuron 9:383-391). Aberrant, excessive, or uncontrolled PTK activity has been shown to result in uncontrolled cell growth and has been observed in diseases such as benign and malignant proliferative disorders, as well as having been observed in diseases resulting from an inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular). The Receptor Tyrosine Kinases (RTKs) comprise a large family of transmembrane receptors with at least nineteen distinct RTK subfamilies having diverse biological activities. The RTK family includes receptors that are crucial for the growth and differentiation of a variety of cell types (Yarden and Ullrich, Ann. Rev. Biochem. 57:433-478, 1988; Ullrich and Schlessinger, Cell 61:243-254, 1990). The intrinsic function of RTKs is activated upon ligand binding, which results in phosphorylation of the receptor and multiple cellular substrates, and subsequently results in a variety of cellular responses (Ullrich & Schlessinger, 1990, Cell 61:203-212). Thus, RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate a corresponding cellular response such as cell division, differentiation, metabolic effects, and changes in the extracellular microenvironment (Schlessinger and Ullrich, 1992, Neuron 9:1-20).

Malignant cells are associated with the loss of control over one or more cell cycle elements. These elements range from cell surface receptors to the regulators of transcription and translation, including the insulin-like growth factors, insulin growth factor-I (IGF-1) and insulin growth factor-2 (IGF-2) (M. J. Ellis, "The Insulin-Like Growth Factor Network and Breast Cancer", Breast Cancer, Molecular Genetics, Pathogenesis and Therapeutics, Humana Press 1999). The insulin growth factor system consists of families of ligands, insulin growth factor binding proteins, and receptors.

A major physiological role of the IGF-1 system is the promotion of normal growth and regeneration. Overexpressed IGF-1R (type 1 insulin-like growth factor receptor) can initiate mitogenesis and promote ligand-dependent neoplastic transformation. Furthermore, IGF-1R plays an important role in the establishment and maintenance of the malignant phenotype.

IGF-1R exists as a heterodimer, with several disulfide bridges. The tyrosine kinase catalytic site and the ATP binding site are located on the cytoplasmic portion of the beta subunit. Unlike the epidermal growth factor (EGF) receptor, no mutant oncogenic forms of the IGF-1R have been identified. However, several oncogenes have been demonstrated to affect IGF-1 and IGF-1R expression. The correlation between a reduction of IGF-1R expression and resistance to transformation has been seen. Exposure of cells to the mRNA antisense to IGF-1R RNA prevents soft agar growth of several human tumor cell lines.

Apoptosis is a ubiquitous physiological process used to eliminate damaged or unwanted cells in multicellular organisms. Misregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, regulators of apoptosis have become an important therapeutic target. It is now established that a major mode of tumor survival is escape from apoptosis. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

Inappropriately high protein kinase activity has been implicated in many diseases resulting from abnormal cellular function. This might arise either directly or indirectly by a failure of the proper control mechanisms for the kinase, related to mutation, over-expression or inappropriate activation of the enzyme; or by an over- or underproduction of cytokines or growth factors participating in the transduction of signals upstream or downstream of the kinase. In all of these instances, selective inhibition of the action of the kinase might be expected to have a beneficial effect.

IGF-1R is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation and phosphorylation of cellular substrates (major substrates are IRS1 and Shc). The ligand-activated IGF-1R induces mitogenic activity in normal cells and plays an important role in abnormal growth.

The IGF-1 pathway in human tumor development has an important role: 1) IGF-1R overexpression is frequently found in various tumors (breast, colon, lung, sarcoma) and is often associated with an aggressive phenotype. 2) High circulating IGF1 concentrations are strongly correlated with prostate, lung and breast cancer risk Furthermore, IGF-1R is required for establishment and maintenance of the transformed phenotype in vitro and in vivo (Baserga R. Exp. Cell. Res., 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytoline-induced apoptosis. Conversely, inhibition of endogenous IGF-1R by dominant negative IGF-1R, triple helix formation or antisense expression vector has been shown to repress transforming activity in vitro and tumor growth in animal models.

Many of the tyrosine kinases, whether an RTK or non-receptor tyrosine kinase, have been found to be involved in cellular signaling pathways involved in numerous disorders, including cancer, psoriasis, fibrosis, atherosclerosis, restenosis, auto-immune disease, allergy, asthma, transplantation rejection, inflammation, thrombosis, nervous system diseases, and other hyperproliferative disorders or hyper-immune responses. It is desirable to provide novel inhibitors of kinases involved in mediating or maintaining disease states to treat such diseases.

The identification of effective small compounds that specifically inhibit signal transduction and cellular proliferation, by modulating the activity of receptor and non-receptor tyrosine and serine/threonine kinases, to regulate and modulate abnormal or inappropriate cell proliferation, differentiation, or metabolism is therefore desirable. In particular, the identification of methods and compounds that specifically inhibit the function of a tyrosine kinase essential for angiogenic processes or for the formation of vascular hyperpermeability leading to edema, ascites, effusions, exudates, macromolecular extravasation, matrix deposition, and their associated disorders would be beneficial.

It has been recognized that inhibitors of protein-tyrosine kinases are useful as selective inhibitors of the growth of mammalian cancer cells. For example, Gleevec™ (also known as imatinib mesylate, or STI571), a 2-phenylpyrimidine tyrosine kinase inhibitor that inhibits the kinase activity of the BCR-ABL fusion gene product, was recently approved by the U.S. Food and Drug Administration for the treatment of CML. This compound, in addition to inhibiting BCR-ABL kinase, also inhibits KIT kinase and PDGF receptor kinase, although it is not effective against all mutant isoforms of KIT kinase. In recent clinical studies on the use of Gleevec™ to treat patients with GIST, a disease in which KIT kinase is involved in transformation of the cells, many of the patients showed marked clinical improvement. Other kinase inhibitors show even greater selectively. For example, the 4-anilinoquinazoline compound Tarceva™ inhibits only EGF receptor kinase with high potency, although it can inhibit the signal transduction of other receptor kinases, probably because such receptors heterodimerize with the EGF receptor.

In view of the importance of PTKs to the control, regulation, and modulation of cell proliferation and the diseases and disorders associated with abnormal cell proliferation, many attempts have been made to identify small molecule tyrosine kinase inhibitors. Bis-, mono-cyclic, bicyclic or heterocyclic aryl compounds (International Patent Publication No. WO 92/20642) and vinylene-azaindole derivatives (International Patent Publication No. WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0566266 A1; Expert Opin. Ther. Pat. (1998), 8(4): 475-478), selenoindoles and selenides (International Patent Publication No. WO 94/03427), tricyclic polyhydroxylic compounds (International Patent Publication No. WO 92/21660) and benzylphosphonic acid compounds (International Patent Publication No. WO 91/15495) have been described as compounds for use as tyrosine kinase inhibitors for use in the treatment of cancer. Anilinocinnolines (PCT WO97/34876) and quinazoline derivative compounds (International Patent Publication No. WO 97/22596; International Patent Publication No. WO97/42187) have been described as inhibitors of angiogenesis and vascular permeability. Bis(indolylmaleimide) compounds have been described as inhibiting particular PKC serine/threonine kinase isoforms whose signal transducing function is associated with altered vascular permeability in VEGF-related diseases (International Patent Publication Nos. WO 97/40830 and WO 97/40831).

International Patent Publication Nos. WO 03/018021 and WO 03/018022 describe pyrimidines for treating IGF-1R related disorders, International Patent Publication Nos. WO 02/102804 and WO 02/102805 describe cyclolignans and cyclolignans as IGF-1R inhibitors, International Patent Publication No. WO 02/092599 describes pyrrolopyrimidines for the treatment of a disease which responds to an inhibition of the IGF-1R tyrosine kinase, International Patent Publication No. WO 01/72751 describes pyrrolopyrimidines as tyrosine kinase inhibitors. International Patent Publication No. WO 00/71129 describes pyrrolotriazine inhibitors of kinases. International Patent Publication No. WO 97/28161 describes pyrrolo [2,3-d]pyrimidines and their use as tyrosine kinase inhibitors.

Parrizas, et al. describes tyrphostins with in vitro and in vivo IGF-1R inhibitory activity (Endocrinology, 138:1427-1433 (1997)), and International Patent Publication No. WO 00/35455 describes heteroaryl-aryl ureas as IGF-1R inhibitors. International Patent Publication No. WO 03/048133 describes pyrimidine derivatives as modulators of IGF-1R. International Patent Publication No. WO 03/024967 describes chemical compounds with inhibitory effects towards kinase proteins. International Patent Publication No. WO 03/068265 describes methods and compositions for treating hyperproliferative conditions. International Patent Publication No. WO 00/17203 describes pyrrolopyrimidines as protein kinase inhibitors. Japanese Patent Publication No. JP 07/133280 describes a cephem compound, its production and antimicrobial composition. A. Albert et al., Journal of the Chemical Society, 11: 1540-1547 (1970) describes pteridine studies and pteridines unsubstituted in the 4-position, a synthesis from pyrazines via 3,4-dhydropteridines. A. Albert et al., Chem. Biol. Pteridines Proc. Int. Symp., 4th, 4: 1-5 (1969) describes a synthesis of pteridines (unsubstituted in the 4-position) from pyrazines, via 3-4-dihydropteridines.

IGF-1R performs important roles in cell division, development, and metabolism, and in its activated state, plays a role in oncogenesis and suppression of apoptosis. IGF-1R is known to be overexpressed in a number of cancer cell lines (IGF-1R overexpression is linked to acromegaly and to cancer of the prostate). By contrast, down-regulation of IGF-1R expression has been shown to result in the inhibition of tumorigenesis and an increased apoptosis of tumor cells.

Although the anticancer compounds described above have made a significant contribution to the art, there is a continuing need in this field of art to improve anticancer pharmaceuticals with better selectivity or potency, reduced toxicity, or fewer side effects.

SUMMARY OF THE INVENTION

The present invention relates to compounds of Formula I:

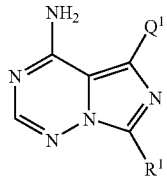

or a pharmaceutically acceptable salt thereof. The compounds of Formula I inhibit the IGF-1R enzyme and are useful for the treatment and/or prevention of various diseases and conditions that respond to treatment by inhibition of IGF-1R. In particular, compounds of this invention are useful as inhibitors of tyrosine kinases that are important in hyperproliferative diseases, especially cancer.

DETAILED DESCRIPTION OF THE INVENTION

The present invention relates to a compound of Formula I:

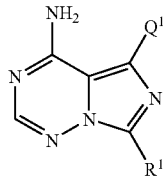

or a pharmaceutically acceptable salt thereof, wherein:

$Q^1$ is aryl$^1$, heteroaryl$^1$, cycloC$_{3-10}$alkyl, heterocyclyl, cycloC$_{3-10}$alkenyl, or heterocycloalkenyl, any of which is optionally substituted by one to five independent G$^{10}$ substituents;

$R^1$ is C$_{0-10}$alkyl, cycloC$_{3-10}$alkyl, bicycloC$_{5-10}$alkyl, aryl, heteroaryl, aralkyl, heteroaralkyl, heterocyclyl, or heterobicycloC$_{5-10}$alkyl, any of which is optionally substituted by one or more independent G$^{11}$ substituents;

G$^{10}$ and G$^{41}$ are each independently halo, oxo, —CF$_3$, —OCF$_3$, —OR$^2$, —NR$^2$R$^3$(R$^{2a}$)$_{j1}$, —C(O)R$^2$, —CO$_2$R$^2$, —CONR$^2$R$^3$, —NO$_2$, —CN, —S(O)$_{j1}$R$^2$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —C(=S)OR$^2$, —C(=O)SR$^2$, —NR$^2$C(=NR$^3$)NR$^{2a}$R$^{3a}$, —NR$^2$C(=NR$^3$)OR$^{2a}$, —NR$^2$C(=NR$^3$)SR$^{2a}$, —OC(=O)OR$^2$, —OC(=O)NR$^2$R$^3$, —OC(=O)SR$^2$, —SC(=O)OR$^2$, —SC(=O)NR$^2$R$^3$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$-alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{222}$, —NR$^{222}$R$^{333}$(R$^{222a}$)$_{j1a}$, —C(O)R$^{222}$, —CO$_2$R$^{222}$, —CONR$^{222}$R$^{333}$, —NO$_2$, —CN, —S(O)$_{j1a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(=O)SR$^{222}$, —SC(=O)OR$^{222}$, or —SC(=O)NR$^{222}$R$^{333}$ substituents;

or G$^{10}$ optionally is —(X$^1$)$_n$—(Y$^1$)$_m$—R$^4$;

or G$^{41}$ optionally is —(X$^1$)$_n$—(Y$^1$)$_m$—C$_{0-10}$alkyl;

or G$^{10}$ and G$^{41}$ are each optionally independently aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{222}$, —NR$^{222}$R$^{333}$(R$^{222a}$)$_{j2a}$, —C(O)R$^{222}$, —CO$_2$R$^{222}$, —CONR$^{222}$R$^{333}$, —NO$_2$, —CN, —S(O)$_{j2a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(=O)SR$^{222}$, —SC(=O)OR$^{222}$, or —SC(=O)NR$^{222}$R$^{333}$ substituents;

G$^{11}$ is halo, oxo, —CF$_3$, —OCF$_3$, OR$^{21}$, —NR$^{21}$R$^{31}$(R$^{21a}$)$_{j3}$, —C(O)R$^{21}$, —CO$_2$R$^{21}$, —CONR$^{21}$R$^{31}$, —NO$_2$, —CN, —S(O)$_{j3}$R$^{21}$, —SO$_2$NR$^{21}$R$^{31}$, —NR$^{21}$C(=O)R$^{31}$, —NR$^{21}$C(=O)OR$^{31}$, —NR$^{21}$C(=O)NR$^{21}$R$^{21a}$, —NR$^{21}$S(O)$_{j3}$R$^{31}$, —C(=S)OR$^{21}$, —C(=O)SR$^{21}$, —NR$^{21}$C(=NR$^{31}$)NR$^{21a}$R$^{31a}$, —NR$^{21}$C(=NR$^{31}$)OR$^{21a}$, —NR$^{21}$C(=NR$^{31}$)SR$^{21a}$, —OC(=O)OR$^{21}$, —OC(=O)NR$^{21}$R$^{31}$, —OC(=O)SR$^{21}$, —SC(=O)OR$^{21}$, —SC(=O)NR$^{21}$R$^{31}$, —P(O)OR$^{21}$OR$^{31}$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{2221}$, —NR$^{2221}$R$^{3331}$(R$^{2221a}$)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{333l}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents;

or G$^{11}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{2221a}$)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO NR$^{2221}$R$^{3331}$, —NR$^{2221}$C(=O)R$^{3331}$, —NR$^{2221}$C(=O)OR$^{3331}$, —NR$^{2221}$C(=)NR$^{3331}$R$^{2221a}$, —NR$^{2221}$S(O)$_{j3a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents;

or G$^{11}$ is C, taken together with the carbon to which it is attached forms a C=C double bond which is substituted with R$^5$ and G$^{12}$;

$R^2$, $R^{2a}$, $R^3$, $R^{3a}$, $R^{222}$, $R^{222a}$, $R^{333}$, $R^{333a}$, $R^{21}$, $R^{21a}$, $R^{31}$, $R^{31a}$, $R^{2221}$, $R^{2221a}$, $R^{3331}$, and $R^{3331a}$ are each independently $C_{0-10}$alkyl, $C_{2-10}$alkenyl, $C_{2-10}$alkynyl, $C_{1-10}$alkoxy $C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted by one or more independent $G^{13}$ substituents;

or in the case of $-NR^2R^3(R^{2a})_{j1}$ or $-NR^{21}R^{31}(R^{21a})_{j3}$ or $-NR^{222}R^{333}(R^{222a})_{j1a}$ or $-NR^{222}R^{333}(R^{222a})_{j2a}$ or $-NR^{2221}R^{3331}(R^{2221a})_{j3a}$, $R^2$ and $R^3$, or $R^{21}$ and $R^{31}$, or $R^{222}$ and $R^{333}$, or $R^{2221}$ and $R^{3331}$, respectfully, are optionally taken together with the nitrogen atom to which they are attached to form a 3-10 membered saturated or unsaturated ring, wherein said ring is optionally substituted by one or more independent $G^{14}$ substituents and wherein said ring optionally includes one or more independent heteroatoms other than the nitrogen to which $R^2$ and $R^3$, or $R^{222}$ and $R^{333}$, or $R^{2221}$ and $R^{3331}$ are attached;

$X^1$ and $Y^1$ are each independently —O—, —$NR^7$—, —$S(O)_{j4}$—, —$CR^5R^6$—, —$N(C(O)OR^7)$—, —$N(C(O)R^7)$—, —$N(SO_2R^7)$—, —$CH_2O$—, —$CH_2S$—, —$CH_2N(R^7)$—, —$CH(NR^7)$—, —$CH_2N(C(O)R^7)$—, —$CH_2N(C(O)OR^7)$—, —$CH_2N(SO_2R^7)$—, —$CH(NHR^7)$—, —$CH(NHC(O)R^7)$—, —$CH(NHSO_2R^7)$—, —$CH(NHC(O)OR^7)$—, —$CH(OC(O)R^7)$—, —$CH(OC(O)NHR^7)$—, —CH=CH—, —C≡C—, —$C(=NOR^7)$—, —$C(O)$—, —$CH(OR^7)$—, —$C(O)N(R^7)$—, —$N(R^7)C(O)$—, —$N(R^7)S(O)$—, —$N(R^7)S(O)_2$—, —$OC(O)N(R^7)$—, —$N(R^7)C(O)N(R^8)$—, —$NR^7C(O)O$—, —$S(O)N(R^7)$—, —$S(O)_2N(R^7)$—, —$N(C(O)R^7)S(O)$—, —$N(C(O)R^7)S(O)_2$—, —$N(R^7)S(O)N(R^8)$—, —$N(R^7)S(O)_2N(R^8)$—, —$C(O)N(R^7)C(O)$—, —$S(O)N(R^7)C(O)$—, —$S(O)_2N(R^7)C(O)$—, —$OS(O)N(R^7)$—, —$OS(O)_2N(R^7)$—, —$N(R^7)S(O)O$—, —$N(R^7)S(O)_2O$—, —$N(R^7)S(O)C(O)$—, —$N(R^7)S(O)_2C(O)$—, —$SON(C(O)R^7)$—, —$SO_2N(C(O)R^7)$—, —$N(R^7)SON(R^8)$—, —$N(R^7)SO_2N(R^8)$—, —$C(O)O$—, —$N(R^7)P(OR^8)O$—, —$N(R^7)P(OR^8)$—, —$N(R^7)P(O)(OR^8)O$—, —$N(R^7)P(O)(OR^8)$—, —$N(C(O)R^7)P(OR^8)O$—, —$N(C(O)R^7)P(OR^8)$—, —$N(C(O)R^7)P(O)(OR^8)O$—, —$N(C(O)R^7)P(OR^8)$—, —$CH(R^7)S(O)$—, —$CH(R^7)S(O)_2$—, —$CH(R^7)N(C(O)OR^8)$—, —$CH(R^7)N(C(O)R^8)$—, —$CH(R^7)N(SO_2R^8)$—, —$CH(R^7)O$—, —$CH(R^7)S$—, —$CH(R^7)N(R^8)$—, —$CH(R^7)N(C(O)R^8)$—, —$CH(R^7)N(C(O)OR^8)$—, —$CH(R^7)N(SO_2R^8)$—, —$CH(R^7)C(=NOR^8)$—, —$CH(R^7)C(O)$—, —$CH(R^7)CH(OR^8)$—, —$CH(R^7)C(O)N(R^8)$—, —$CH(R^7)N(R^8)C(O)$—, —$CH(R^7)N(R^8)S(O)$—, —$CH(R^7)N(R^8)S(O)_2$—, —$CH(R^7)OC(O)N(R^8)$—, —$CH(R^7)N(R^8)C(O)N(R^{7a})$—, —$CH(R^7)NR^8C(O)O$—, —$CH(R^7)S(O)N(R^8)$—, —$CH(R^7)S(O)_2N(R^8)$—, —$CH(R^7)N(C(O)R^8)S(O)$—, —$CH(R^7)N(C(O)R^8)S(O)$—, —$CH(R^7)N(R^8)S(O)N(R^{7a})$—, —$CH(R^7)N(R^8)S(O)_2N(R^{7a})$—, —$CH(R^7)C(O)N(R)C(O)$—, —$CH(R^7)S(O)N(R^8)C(O)$—, —$CH(R^7)S(O)_2N(R^8)C(O)$—, —$CH(R^7)OS(O)N(R^8)$—, —$CH(R^7)OS(O)_2N(R^8)$—, —$CH(R^7)N(R^8)S(O)O$—, —$CH(R^7)N(R^8)S(O)_2O$—, —$CH(R^7)N(R^8)S(O)C(O)$—, —$CH(R^7)N(R^8)S(O)_2C(O)$—, —$CH(R^7)SON(C(O)R^8)$—, —$CH(R^7)SO_2N(C(O)R^8)$—, —$CH(R^7)N(R^8)SON(R^{7a})$—, —$CH(R^7)N(R^8)SO_2N(R^{7a})$—, —$CH(R^7)C(O)O$—, —$CH(R^7)N(R^8)P(OR^{7a})O$—, —$CH(R^7)N(R^8)P(OR^{7a})$—, —$CH(R^7)N(R^8)P(O)(OR^{7a})O$—, —$CH(R^7)N(R^8)P(O)(OR^{7a})$—, —$CH(R^7)N(C(O)R^8)P(OR^{7a})O$—, —$CH(R^7)N(C(O)R^8)P(OR^{7a})$—, —$CH(R^7)N(C(O)R^8)P(O)(OR^{7a})O$—, or —$CH(R^7)N(C(O)R^8)P(OR^{7a})$—;

or $X^1$ and $Y^1$ are each independently represented by one of the following structural formulas:

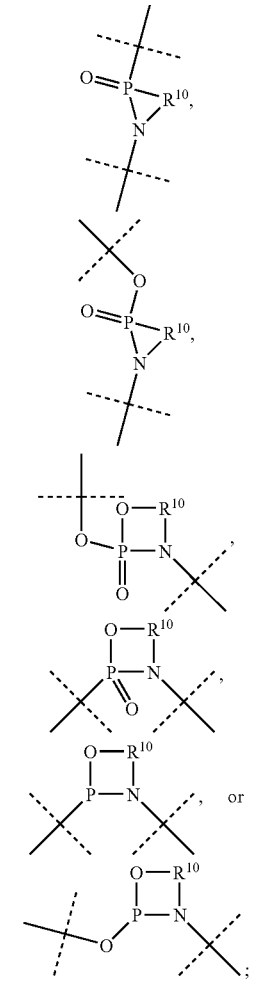

$R^{10}$, taken together with the phosphinamnide or phosphonamide, forms a 5-, 6-, or 7-membered aryl, heteroaryl, or heterocyclyl ring system;

$R^5$, $R^6$, $G^{12}$, $G^{13}$, $G^{14}$, and $G^{15}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, $CONR^{77}R^{87}$, —$NO_2$, —CN, —$S(O)_{j5a}R^{77}$, —$SO_2NR^{77}R^{87}$, —$NR^{77}C(=O)R^{87}$, —$NR^{77}C(=O)OR^{87}$, —$NR^{77}C(=O)NR^{87}R^{77a}$, —$NR^{77}S(O)_{j5a}R^{87}$, —C=S)$OR^{77}$, —$C(=O)SR^{77}$, —$NR^{77}C$ (=NR$^{87}$)NR$^{77a}$R$^{87a}$, —NR$^{77}$C(=NR$^{87}$)OR$^{77a}$, —NR$^{77}$C(=NR$^{87}$)SR$^{77a}$, —OC(=O)OR$^{77}$, —OC(=O)NR$^{77}$R$^{87}$, —OC(=O)SR$^{77}$, —SC(=O)OR$^{77}$, —P(O)OR$^{77}$OR$^{87}$, or —SC(=O)NR$^{77}$R$^{87}$ substituents;

or R$^5$ with R$^6$ are optionally taken together with the respective carbon atom to which they are attached form a 3-10 membered saturated or unsaturated ring, wherein said ring is optionally substituted with R$^{69}$ and wherein said ring optionally includes one or more independent heteroatoms;

R$^7$, R$^{7a}$, and R$^8$ are each independently acyl, C$_{0-10}$alkyl, C$_{2-10}$alkenyl, aryl, heteroaryl, heterocyclyl or cycloC$_{3-10}$alkyl, any of which is optionally substituted by one or more independent G$^{15}$ substituents;

R$^4$ is C$_{0-10}$alkyl, C$_{2-10}$alkenyl, C$_{2-10}$alkynyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents;

R$^{69}$ is halo, —OR$^{41}$, —SH, —NR$^{41}$R$^{51}$, —CO$_2$R$^{41}$, —CONR$^{41}$R$^{51}$, —NO$_2$, —CN, —S(O)$_{j6}$R$^{41}$, —SO$_2$NR$^{41}$R$^{51}$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, cyano, nitro, —OR$^{778}$, —SO$_2$NR$^{778}$R$^{888}$, or —NR$^{778}$R$^{888}$ substituents;

or R$^{69}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, hetaryl-C$_{2-10}$alkynyl, mono(C$_{1-6}$alkyl)aminoC$_{1-6}$alkyl, di(C$_{1-6}$alkyl)aminoC$_{1-6}$alkyl, mono(aryl)aminoC$_{1-6}$alkyl, di(aryl)aminoC$_{1-6}$alkyl, mono(hetaryl)aminoC$_{1-6}$alkyl, di(hetaryl)aminoC$_{1-6}$alkyl, or —N(C$_{1-6}$alkyl)-C$_{1-6}$alkyl-aryl, any of which is optionally substituted with one or more independent halo, cyano, nitro, —OR$^{778}$, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, C$_{1-4}$alkoxycarbonyl, —CONR$^{778}$R$^{888}$, —SO$_2$NR$^{778}$R$^{888}$, or —NR$^{778}$R$^{888}$ substituents;

or in the case of —NR$^{41}$R$^{51}$, R$^{41}$ and R$^{51}$ are optionally taken together with the nitrogen atom to which they are attached to form a 3-10 membered saturated or unsaturated ring, wherein said ring is optionally substituted with one or more independent halo, cyano, hydroxy, nitro, C$_{1-10}$alkoxy, —SO$_2$NR$^{778}$R$^{888}$, or —NR$^{778}$R$^{888}$ substituents and wherein said ring optionally includes one or more independent heteroatoms other than the nitrogen to which R$^{41}$ and R$^{51}$ are attached;

R$^{41}$, R$^{51}$, R$^{77}$, R$^{77a}$, R$^{87}$, R$^{87a}$, R$^{778}$, and R$^{888}$ are each independently C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, C$_{1-10}$alkylcarbonyl, C$_{2-10}$alkenylcarbonyl, C$_{2-10}$alkynylcarbonyl, C$_{1-10}$alkoxycarbonyl, C$_{1-10}$alkoxycarbonylC$_{1-10}$alkyl, monoC$_{1-6}$alkylaminocarbonyl, diC$_{1-6}$alkylaminocarbonyl, mono(aryl)aminocarbonyl, di(aryl)aminocarbonyl, C$_{1-10}$alkyl(aryl)aminocarbonyl, mono(hetaryl)aminocarbonyl, di(hetaryl)aminocarbonyl, or C$_{1-10}$alkyl alkyl(hetaryl)aminocarbonyl, any of which is optionally substituted with one or more independent halo, cyano, hydroxy, nitro, C$_{1-10}$alkoxy, —SO$_2$N(C$_{0-4}$alkyl)(C$_{0-4}$alkyl), or —N(C$_{0-4}$alkyl)(C$_{0-4}$alkyl) substituents;

or R$^{41}$, R$^{51}$, R$^{77}$, R$^{77a}$, R$^{87}$, R$^{87a}$, R$^{778}$, and R$^{888}$ are each independently aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, hetaryl-C$_{2-10}$alkynyl, mono(C$_{1-6}$alkyl)aminoC$_{1-6}$alkyl, di(C$_{1-6}$alkyl)aminoC$_{1-6}$alkyl, mono(aryl)aminoC$_{1-6}$alkyl, di(aryl)aminoC$_{1-6}$alkyl, mono(hetaryl)aminoC$_{1-6}$alkyl, di(hetaryl)aminoC$_{1-6}$alkyl, or —N(C$_{1-6}$alkyl)-C$_{1-6}$alkyl-aryl, any of which is optionally substituted with one or more independent halo, cyano, nitro, —(C$_{0-4}$alkyl), C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, C$_{1-4}$alkoxycarbonyl, —CON(C$_{0-4}$alkyl)(C$_{0-4}$alkyl), —SO$_2$N(C$_{0-4}$alkyl)(C$_{0-4}$alkyl), or —N(C$_{0-4}$alkyl)(C$_{0-4}$alkyl) substituents; and n, m, j1, j1a, j2a, j3, j3a, j4, j5a, and j6 are each independently 0, 1, or 2.

In an aspect of the present invention, a compound is represented by Formula I, or a pharmaceutically acceptable salt thereof, wherein R$^1$ is cycloC$_{3-10}$alkyl, bicycloC$_{5-10}$alkyl, aryl, heteroaryl, aralkyl, heteroaralkyl, heterocyclyl, or heterobicycloC$_{5-10}$alkyl, any of which is optionally substituted by one or more independent G$^{11}$ substituents and the other variables are described as above for Formula I.

In an embodiment of this aspect, a compound is represented by Formula I, or pharmaceutically acceptable salt thereof, wherein R$^1$ is cycloC$_{3-10}$alkyl, aryl, heteroaryl, aralkyl, heteroaralkyl, or heterocyclyl, any of which is optionally substituted by one or more independent G$^{11}$ substituents and the other variables are described as above for Formula I.

In an embodiment of this aspect, a compound is represented by Formula I, or pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, any of which is optionally substituted by one or more independent G$^{10}$ substituents; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is heteroaryl$^1$, which is optionally substituted by one or more independent G$^{10}$ substituents; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$, which is optionally substituted by one or more independent G$^{10}$ substituents; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent $G^{11}$ substituents; wherein $Q^1$ is aryl$^1$ or heteroaryl$^1$, any of which is optionally substituted by one or more independent $G^{10}$ substituents;

wherein $G^{10}$ is halo, —OR$^2$, —NR$^2$R$^3$, —C(O)R$^2$, —CO$_2$R$^2$, —CONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)OR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$(C=O)NR$^{333}$R$^{222a}$, —NR$^{222}$S(O)$_{j1a}$R$^{333}$, —NR$^{222}$C(=NR$^{333}$)NR$^{222a}$R$^{333a}$, or —O(C=O)NR$^{222}$R$^{333}$ substituents; or $G^{10}$ is —(X$^1$)$_n$—(Y$^1$)$_m$—R$^4$; or $G^{10}$ is aryl-C$_{0-10}$alkyl or hetaryl-C$_{0-10}$alkyl, any of which is optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —NR$^{222}$C(=NR$^{333}$)NR$^{222a}$R$^{333a}$, or —OC(=O)NR$^{222}$R$^{333}$ substituents; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, any of which is optionally substituted by one or more independent G$^{10}$ substituents;

wherein $G^{10}$ is halo, —OR$^2$, —NR$^2$R$^3$, —C(O)R$^2$, —CO$_2$R$^2$, —CONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)OR$^2$, —OC(=O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(O)$_{j1a}$R$^{333}$, —NR$^{222}$C(=NR$^{333}$)NR$^{222a}$R$^{333a}$, or —OC(=O)NR$^{222}$R$^{333}$ substituents; or $G^{10}$ is —(X$^1$)$_n$—(Y$^1$)$_m$—R$^4$; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—; wherein n and m are both 1; j4 is 1 or 2; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—; wherein n and m are both 1; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CH$_2$—; wherein n and m are both 1; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—; wherein n and m are both 1; j4 is 1 or 2; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this aspect, a compound is represented by Formula I, or a pharmaceutically acceptable salt thereof, wherein R$^1$ is cycloC$_{3-10}$alkyl, aryl, heteroaryl, aralkyl, or heterocyclyl, any of which is optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—; wherein n and m are both 1; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this aspect, a compound is represented by Formula I, or a pharmaceutically acceptable salt thereof, wherein $R^1$ is cyclo$C_{3-10}$alkyl, aryl, heteroaryl, aralkyl, or heterocyclyl, any of which is optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O— or —CH$_2$—; wherein n and m are both 1; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this aspect, a compound is represented by Formula I, or a pharmaceutically acceptable salt thereof, wherein $R^1$ is cyclo$C_{3-10}$alkyl, aryl, heteroaryl, aralkyl, or heterocyclyl, any of which is optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $R^4$ is aryl or heteroaryl, any of which is optionally substituted by one or more independent $G^{41}$ substituents; and the other variables are described as above for Formula I.

In an embodiment of this aspect, a compound is represented by Formula I, or a pharmaceutically acceptable salt thereof, wherein $R^1$ is cyclo$C_{3-10}$alkyl, aryl, heteroaryl, aralkyl, or heterocyclyl, any of which is optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O—, —NR$^7$—, —CR$^5$R$^6$—, —S(O)$_{j4}$—, or —C(O)—; wherein n and m are both 1; j4 is 1 or 2; wherein $R^4$ is aryl or heteroaryl, any of which is optionally substituted by one or more independent $G^{41}$ substituents; and the other variables are described as above for Formula I.

In an embodiment of this aspect, a compound is represented by Formula I, or a pharmaceutically acceptable salt thereof, wherein $R^1$ is cyclo$C_{3-10}$alkyl, aryl, heteroaryl, aralkyl, or heterocyclyl, any of which is optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O— or —CR$^5$R$^6$—; wherein n and m are both 1; wherein $R^4$ is aryl or heteroaryl, any of which is optionally substituted by one or more independent $G^{41}$ substituents; and the other variables are described as above for Formula I.

In an embodiment of this aspect, a compound is represented by Formula I, or a pharmaceutically acceptable salt thereof, wherein $R^1$ is cyclo$C_{3-10}$alkyl, aryl, heteroaryl, aralkyl, or heterocyclyl, any of which is optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O— or —CH$_2$—; wherein n and m are both 1; wherein $R^4$ is aryl or heteroaryl, any of which is optionally substituted by one or more independent $G^{41}$ substituents; and the other variables are described as above for Formula I.

In an embodiment of this aspect, a compound is represented by Formula I, or a pharmaceutically acceptable salt thereof, wherein $R^1$ is cyclo$C_{3-10}$alkyl, aryl, heteroaryl, aralkyl, or heterocyclyl, any of which is optionally substituted by one or more independent $G^{11}$ substituents; wherein $Q^1$ is aryl$^1$ substituted by said one to five independent $G^{10}$ substituents wherein at least one of said $G^{10}$ substituents is —$(X^1)_n$—$(Y^1)_m$—$R^4$; n and m are both 1; $R^4$ is aryl optionally substituted by one or more $G^{41}$ substituents; $X^1$ is —O—; $Y^1$ is —CH$_2$—; and the other variables are described as above for Formula I.

In an embodiment of this aspect, a compound is represented by Formula I, or a pharmaceutically acceptable salt thereof, wherein $R^1$ is cyclo$C_{3-10}$alkyl, aryl, heteroaryl, aralkyl, or heterocyclyl, any of which is optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents;

wherein $G^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, —NR$^{21}$S(O)$_{j3}$R$^{31}$, —OC(=O)OR$^{21}$, —OC(=O)NR$^{21}$R$^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, —CF$_3$, —OCF$_3$, —OR$^{2221}$, —NR$^{2221}$R$^{3331}$(R$^{2221a}$)$_{j3a}$, —C(O)R$^{222a}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In a second aspect of the present invention, a compound is represented by Formula I, or a pharmaceutically acceptable salt thereof, wherein $R^1$ is aryl, heteroaryl, aralkyl, or heteroaralkyl, any of which is optionally substituted by one or more independent $G^{11}$ substituents and the other variables are described as above for Formula I.

In an embodiment of this second aspect, a compound is represented by Formula I, or a pharmaceutically acceptable salt thereof, wherein $R^1$ is aryl or heteroaryl, any of which is optionally substituted by one or more independent $G^{11}$ substituents and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is aryl$^1$ or heteroaryl$^1$, any of which is optionally substituted by one or more independent $G^{10}$ substituents; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is heteroaryl$^1$, which is optionally substituted by one or more independent $G^{10}$ substituents; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is aryl$^1$, which is optionally substituted by one or more independent $G^{10}$ substituents; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is heteroaryl$^1$, which is optionally substituted by one or more independent $G^{10}$ substituents;
wherein $G^{10}$ is halo, —OR$^2$, —NR$^2$R$^3$, —C(O)R$^2$, —CO$_2$R$^2$, —CONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)OR$^2$, —OC(=O)NR$^2$R$^3$, $C_{0-10}$alkyl, $C_{2-10}$alkenyl, $C_{1-10}$alkoxyC$_{1-10}$alkyl, $C_{1-10}$-alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$(C=O) NR$^{333}$R$^{222a}$, —NR$^{222}$S(O)$_{j1a}$R$^{333}$, —NR$^{222}$C(=NR$^{333}$) NR$^{222a}$R$^{333a}$, or —OC(=O)NR$^{222}$R$^{333}$ substituents; or $G^{10}$ is —(X$^1$)$_n$—(Y$^1$)$_m$—R$^4$; or $G^{10}$ is aryl-C$_{0-10}$alkyl or hetaryl-C$_{0-10}$alkyl, any of which is optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O) OR$^{333}$, —NR$^{222}$C(=O)NR$^{333}$R$^{222a}$, —NR$^{222}$S(O)$_{j2a}$R$^{333}$, —NR$^{222}$C(=NR$^{333}$)NR$^{222a}$R$^{333a}$, or —OC(=O) NR$^{222}$R$^{333}$ substituents; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is aryl$^1$, which is optionally substituted by one or more independent $G^{10}$ substituents;
wherein $G^{10}$ is halo, —OR$^2$, —NR$^2$R$^3$, —C(O)R$^2$, —CO$_2$R$^2$, —CONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)OR$_2$, —OC(=O)NR$^2$R$^3$, $C_{0-10}$alkyl, $C_{2-10}$alkenyl, $C_{1-10}$alkoxyC$_{1-10}$alkyl, $C_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$(C=O) NR$^{333}$R$^{222a}$, —NR$^{222}$S(O)$_{j1a}$R$^{333}$, —NR$^{222}$C(=NR$^{333}$) NR$^{222a}$R$^{333a}$, or —OC(=O)NR$^{222}$R$^{333}$ substituents; or $G^{10}$ is —(X$^1$)$_n$—(Y$^1$)$_m$—R$^4$; or $G^{10}$ is aryl-C$_{0-10}$alkyl or hetaryl-C$_{0-10}$alkyl, any of which is optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O) OR$^{333}$, —NR$^{222}$C(=O)NR$^{333}$R$^{222a}$, —NR$^{222}$S(O)$_{j2a}$R$^{333}$, —NR$^{222}$C(=NR$^{333}$)NR$^{222a}$R$^{333a}$, or —OC(=O) NR$^{222}$R$^{333}$ substituents; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is heteroaryl$^1$, which is optionally substituted by one or more independent $G^{10}$ substituents;
wherein $G^{10}$ is halo, —OR$^2$, —NR$^2$R$^3$, —C(O)R$^2$, —CO$_2$R$^2$, —CONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)OR$^2$, —OC(=O)NR$^2$R$^3$, $C_{0-10}$alkyl, $C_{2-10}$alkenyl, $C_{1-10}$alkoxyC$_{1-10}$alkyl, $C_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$C(=O) NR$^{333}$R$^{222a}$, —NR$^{222}$S(O)$_{j1a}$R$^{333}$, —NR$^{222}$C(=NR$^{333}$) NR$^{222a}$R$^{333a}$, or —OC(=O)NR$^{222}$R$^{333}$ substituents; or $G^{10}$ is —(X$^1$)$_n$—(Y$^1$)$_m$—R$^4$; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is aryl$^1$, which is optionally substituted by one or more independent $G^{10}$ substituents;
wherein $G^{10}$ is halo, —OR$^2$, —NR$^2$R$^3$, —C(O)R$^2$, —CO$_2$R$^2$, —CONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)OR$^2$, —OC(=O)NR$^2$R$^3$, $C_{0-10}$alkyl, $C_{2-10}$alkenyl, $C_{1-10}$alkoxyC$_{1-10}$alkyl, $C_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$C(=O) NR$^{333}$R$^{222a}$, —NR$^{222}$S(O)$_{j1a}$R$^{333}$, —NR$^{222}$C(=NR$^{333}$) NR$^{222a}$R$^{333a}$, or —OC(=O)NR$^{222}$R$^{333}$ substituents; or $G^{10}$ is —(X$^1$)$_n$—(Y$^1$)$_m$—R$^4$; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is aryl$^1$ or heteroaryl$^1$; wherein $Q^1$ is substituted by said one to five independent $G^{10}$ substituents wherein at least one of said $G^{10}$ substituents is —(X$^1$)$_n$—(Y$^1$)$_m$—R$^4$; wherein n and m are both 1; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—; wherein n and m are both 1; j4 is 1 or 2; and the other variables are described as above for Formula I.

In an embodiment of this second aspect, a compound is represented by Formula I, or a pharmaceutically acceptable salt thereof, wherein $R^1$ is aryl, optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is —(X$^1$)$_n$—(Y$^1$)$_m$—R$^4$; wherein X$^1$ and Y$^1$ are each independently —O— or —CR$^5$R$^6$—; wherein n and m are both 1; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CH$_2$—; wherein n and m are both 1; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$; wherein Q$^1$ is substituted by said one to five independent G$^{10}$ substituents wherein at least one of said G$^{10}$ substituents is —(X$^1$)$_n$—(Y$^1$)$_m$—R$^4$; wherein n and m are both 1; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, CR$^5$R$^6$—, —S(O)$_{j4}$—, or —C(O)—; wherein n and m are both 1; j4 is 1 or 2; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or CR$^5$R$^6$—; wherein n and m are both 1; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$; wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or CH$_2$—; wherein n and m are both 1; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$; wherein Q$^1$ is substituted by said one to five independent G$^{10}$ substituents wherein at least one of said G$^{10}$ substituents is —(X$^1$)$_n$—(Y$^1$)$_m$—R$^4$; wherein n and m are both 1; R$^4$ is aryl or heteroaryl, any of which is optionally substituted by one or more independent G$^{41}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—; wherein n and m are both 1; j4 is 1 or 2; R$^4$ is aryl or heteroaryl, any of which is optionally substituted by one or more independent G$^{41}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—; wherein n and m are both 1; R$^4$ is aryl or heteroaryl, any of which is optionally substituted by one or more independent G$^{41}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CH$_2$—; wherein n and m are both 1; wherein R$^4$ is aryl or heteroaryl, any of which is optionally substituted by one or more independent G$^{41}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$; wherein Q$^1$ is substituted by said one to five independent G$^{10}$ substituents wherein at least one of said G$^{10}$ substituents is —(X$^1$)$_n$—(Y$^1$)$_m$—R$^4$; wherein n and m are both 1; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents;

wherein G$^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, —NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221}$a)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—; wherein n and m are both 1; j4 is 1 or 2; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents;

wherein G$^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221a}$)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, NR$^{2221}$C(=NR$^{3331}$)NR$^{2221a}$R$^{3331a}$, —NR$^{2221}$C(=NR$^{3331}$)OR$^{2221a}$, —NR$^{2221c}$(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—; wherein n and m are both 1; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents;

wherein G$^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{222a}$)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, —NR$^{2221}$OC(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, NR$^{2221}$C(=NR$^{3331}$)NR$^{2221a}$R$^{3331a}$, —NR$^{2221}$C(=NR$^{3331}$)OR$^{2221a}$, NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CH$_2$—; wherein n and m are both 1; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents;

wherein G$^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221a}$)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this second aspect, a compound is represented by Formula I, or a pharmaceutically acceptable salt thereof, wherein R$^1$ is phenyl optionally substituted by one or more independent G$^{11}$ substituents; and the other variables are described as above for Formula I.

In an embodiment of this second aspect, a compound is represented by Formula I, or a pharmaceutically acceptable salt thereof, wherein R$^1$ is aryl, optionally substituted by one or more independent G$^{11}$ substituents; wherein Q$^1$ is aryl$^1$ substituted by said one to five independent G$^{10}$ substituents wherein at least one of said G$^{10}$ substituents is —(X$^1$)$_n$—(Y$^1$)$_m$—R$^4$; n and m are both 1; R$^4$ is aryl optionally substituted by one or more G$^{41}$ substituents; X$^1$ is —O—; Y$^1$ is —CH$_2$—; and the other variables are described as above for Formula I.

In an embodiment of this second aspect, a compound is represented by Formula I, or a pharmaceutically acceptable salt thereof, wherein R$^1$ is phenyl optionally substituted by one or more independent G$^{11}$ substituents; wherein Q$^1$ is aryl$^1$ substituted by said one to five independent G$^{10}$ substituents wherein at least one of said G$^{10}$ substituents is —(X$^1$)$_n$—(Y$^1$)$_m$—R$^4$; n and m are both 1; R$^4$ is aryl optionally substituted by one or more G$^{41}$ substituents; X$^1$ is —O—; Y$^1$ is —CH$_2$—; and the other variables are described as above for Formula I.

In a third aspect of the present invention, a compound is represented by Formula I, or a pharmaceutically acceptable salt thereof, wherein R$^1$ is cycloC$_{3-10}$alkyl or heterocyclyl, any of which is optionally substituted by one or more independent G$^{11}$ substituents and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$ or heteroaryl$^1$, any of which is optionally substituted by one or more independent $G^{10}$ substituents; and the other variables are described as above for Formula I.

In an embodiment of this third aspect, a compound is represented by Formula I, or a pharmaceutically acceptable salt thereof, wherein $R^1$ is heterocyclyl optionally substituted by one or more hindependent $G^{11}$ substituents; wherein $Q^1$ is heteroaryl$^1$, which is optionally substituted by one or more independent $G^{10}$ substituents; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$, which is optionally substituted by one or more independent $G^{10}$ substituents; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is heteroaryl$^1$, which is optionally substituted by one or more independent $G^{10}$ substituents;

wherein $G^{10}$ is halo, $-OR^2$, $-NR^2R^3$, $-C(O)R^2$, $-CO_2R^2$, $-CONR^2R^3$, $-SO_2NR^2R^3$, $-NR^2C(=O)R^3$, $-NR^2C(=O)OR^3$, $-NR^2C(=O)NR^3R^{2a}$, $-NR^2S(O)_{j1}R^3$, $-OC(=O)OR^2$, $-OC(=O)NR^2R^3$, $C_{0-10}$alkyl, $C_{2-10}$alkenyl, $C_{1-10}$alkoxy$C_{1-10}$alkyl, $C_{0-10}$alkylthio$C_{0-10}$alkyl, cyclo$C_{3-8}$alkyl, cyclo$C_{3-8}$alkenyl, heterocyclyl-$C_{0-10}$oalkyl, or heterocyclyl-$C_{2-10}$alkenyl, any of which is optionally substituted with one or more independent oxo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2NR^{222}R^{333}$, $-NR^{222}C(=O)R^{333}$, $-NR^{222}C(=O)OR^{333}$, $-N^{222}(C=O)NR^{333}R^{222a}$, $-N^{222}S(O)_{j1a}R^{333}$, $-NR^{222}C(=NR^{333})NR^{222a}R^{333a}$ or $-O(C=O)NR^{222}R^{333}$ substituents; or $G^{10}$ is $-(X^1)_n-(Y^1)_m-R^4$; or $G^{10}$ is aryl-$C_{0-10}$alkyl or hetaryl-$C_{0-10}$alkyl, any of which is optionally substituted with one or more independent halo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(O)_{j2a}R^{333}$, $-NR^{222}C(=NR^{333})NR^{222a}R^{333a}$, or $-OC(=O)NR^{222}R^{333}$ substituents; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$, which is optionally substituted by one or more independent $G^{10}$ substituents;

wherein $G^{10}$ is halo, $-OR^2$, $-NR^2R^3$, $-C(O)R^2$, $-CO_2R^2$, $-CONR^2R^3$, $-SO_2NR^2R^3$, $-NR^2C(=O)R^3$, $-NR^2C(=O)OR^3$, $-NR^2C(=O)NR^3R^{2a}$, $-NR^2S(O)_{j1}R^3$, $-OC(=O)OR^2$, $-OC(=O)NR^2R^3$, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent oxo, $-CF_3$, $-OCF_3$, $-OR^{222}$ $NR^{222}R^{333}$, $-C(O)R^{222}$, $-CO_2R^{222}$, $-CONR^{222}R^{333}$, $-SO_2NR^{222}R^{333}$, $-NR^{222}C(=O)R^{333}$, $-NR^{222}C(=O)OR^{333}$, $-N^{222}(C=O)NR^{333}R^{222a}$, $-NR^{222}S(O)_{j1a}R^{333}$, $-NR^{222}C(=NR^{333})$ $NR^{222a}R^{333a}$, or $-O(C=O)NR^{222}R^{333}$ substituents; or $G^{11}$ is $-(X^1)_n-(Y^1)_m-R^4$; or $G^{10}$ is aryl-$C_{0-10}$alkyl or hetaryl-$C_{0-10}$alkyl, any of which is optionally substituted with one or more independent halo, $-CF_3$, $-OCF_3$, $-R^{222}$, $-NR^{222}R^{333}$, $-C(O)R^{222}$, $-CO_2R^{222}$, $-CONR^{222}R^{333}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(O)_{j2a}R^{333}$, $-NR^{222}C(=NR^{333})NR^{222}R^{333a}$, or $-OC(=O)NR^{222}R^{333}$ substituents; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is heteroaryl$^1$, which is optionally substituted by one or more independent $G^{10}$ substituents;

wherein $G^{10}$ is halo, $-OR^2$, $-NR^2R^3$, $-C(O)R^2$, $-CO_2R^2$, $-CONR^2R^3$, $-SO_2NR^2R^3$, $-NR^2C(=O)R^3$, $-NR^2C(=O)OR^3$, $-NR^2C(=O)NR^3R^{2a}$, $-NR^2S(O)_{j1}R^3$, $-OC(=O)OR^2$, $-OC(=O)NR^2R^3$, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent oxo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(O)_{j1a}R^{333}$, $-NR^{222}C(=NR^{333})NR^{222a}R^{333a}$, or $-OC(=O)NR^{222}R^{333}$ substituents; or $G^{10}$ is $-(X^1)_n-(Y^1)_m-R^4$; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$, which is optionally substituted by one or more independent $G^{10}$ substituents;

wherein $G^{10}$ is halo, $-OR^2$, $-NR^2R^3$, $-C(O)R^2$, $-CO_2R^2$, $-CONR^2R^3$, $-SO_2NR^2R^3$, $-NR^2C(=O)R^3$, $-NR^2C(=O)OR^3$, $-NR^2C(=O)NR^3R^{2a}$, $-NR^2S(O)_{j1}R^3$, $-OC(=O)OR^2$, $-OC(=O)NR^2R^3$, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent oxo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(O)_{j1a}R^{333}$, $-NR^{222}C(=NR^{333})NR^{222a}R^{333}a$, or $-OC(=O)NR^{222}R^{333}$ substituents; or $G^{10}$ is $-(X^1)_n-(Y^1)_m-R^4$; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently —O—, —NR$^7$—, —CR$^5$R$^6$—, —S(O)$_{j4}$—, or —C(O)—; wherein n and m are both 1; j4 is 1 or 2; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or CR$^5$R$^6$—, —S(O)$_{j4}$—, or —C(O)—; wherein n and m are both 1; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$, and wherein X$^1$ and Y$^1$ are each independently —O— or —CH$_2$—, —S(O)$_{j4}$—, or —C(O)—; and wherein n and m are both 1; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—; wherein n and m are both 1; j4 is 1 or 2; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—, —S(O)$_{j4}$—, or —C(O)—; wherein n and m are both 1; wherein R$^4$ is C$_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$, and wherein X$^1$ and Y$^1$ are each independently —O— or —CH$_2$—, —S(O)$_{j4}$—, or —C(O)—; and wherein n and m are both 1; wherein R$^4$ is C$_{-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent G$^{41}$ substituents; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein R$^4$ is aryl or heteroaryl, any of which is optionally substituted by one or more independent G$^{41}$ substituents; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—; wherein n and m are both 1; j4 is 1 or 2; wherein R$^4$ is aryl or heteroaryl, any of which is optionally substituted by one or more independent G$^{41}$ substituents; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—, —S(O)$_{j4}$—, or —C(O)—; wherein n and m are both 1; wherein R$^4$ is aryl or heteroaryl, any of which is optionally substituted by one or more independent G$^{41}$ substituents; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ or heteroaryl$^1$, wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CH$_2$—, —S(O)$_{j4}$—, or —C(O)—; wherein n and m are both 1; wherein R$^4$ is aryl or heteroaryl, any of which is optionally substituted by one or more independent G$^{41}$ substituents; and the other variables are described as above for Formula I.

In an embodiment of this third aspect, a compound is represented by Formula I, or a pharmaceutically acceptable salt thereof, wherein R$^1$ is heterocyclyl optionally substituted by one or more independent G$^{11}$ substituents; wherein Q$^1$ is aryl$^1$ substituted by said one to five independent G$^{10}$ substituents wherein at least one of said G$^{10}$ substituents is —(X$^1$)$_n$—(Y$^1$)$_m$—R$^4$; n and m are both 1; R$^4$ is aryl optionally substituted by one or more G$^{41}$ substituents; X$^1$ is —O—; and Y$^1$ is —CH$_2$—; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$ or heteroaryl$^1$; wherein $Q^1$ is substituted by said one to five independent $G^{10}$ substituents wherein at least one of said $G^{10}$ substituents is $-(X^1)_n-(Y^1)_m-R^4$; wherein $R^4$ is $C_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent $G^{41}$ substituents;

wherein $G^{11}$ is $-OR^{21}$, $-NR^{21}R^{31}$, $-CO_2R^{21}$, $-C(O)R^{21}$, $-CONR^{21}R^{31}$, $-NR^{21}C(=O)R^{31}$, $-NR^{21}C(=O)OR^{31}$, $-NR^{21}C(=O)NR^{31}R^{21a}$, $-NR^{21}S(O)_{j3}R^{31}$, $-OC(=O)OR^{21}$, $-OC(=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, $-CF_3$, $-OCF_3$, $-OR^{2221}$, $-NR^{2221}R^{3331}(R^{2221a})_{j3a}$, $-C(O)R^{2221}$, $-CO_2R^{2221}$, $-CONR^{2221}R^{3331}$, $-NO_2$, $-CN$, $-S(O)_{j3a}R^{2221}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-C(=S)OR^{2221}$, $-C(=O)SR^{2221}$, $-NR^{2221}C(=NR^{3331})NR^{2221a}R^{3331a}$, $-NR^{2221}C(=NR^{3331})OR^{2221a}$, $-NR^{2221}C(=NR^{3331})SR^{2221a}$, $-OC(=O)OR^{2221}$, $-OC(=O)NR^{2221}R^{3331}$, $-OC(=O)SR^{2221}$, $-SC(=O)OR^{2221}$, or $-SC(=O)NR^{2221}R^{3331}$ substituents; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$, $-NR^7-$, $-CR^5R^6-$, $-S(O)_{j4}-$, or $-C(O)-$; wherein n and m are both 1; j4 is 1 or 2; wherein $R^4$ is $C_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent $G^{41}$ substituents;

wherein $G^{11}$ is $-OR^{21}$, $-NR^{21}R^{31}$, $-CO_2R^{21}$, $-C(O)R^{21}$, $-CONR^{21}R^{31}$, $-NR^{21}C(=O)R^{31}$, $-NR^{21}C(=O)OR^{31}$, $-NR^{21}C(=O)NR^{31}R^{21a}$, $-NR^{21}S(O)_{j3}R^{31}$, $-OC(=O)OR^{21}$, $-OC(=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, $-CF_3$, $-OCF_3$, $-OR^{2221}$, $-NR^{2221}R^{3331}(R^{2221a})_{j3a}$, $-C(O)R^{2221}$, $-CO_2R^{2221}$, $-CONR^{2221}R^{3331}$, $-NO_2$, $-CN$, $-S(O)_{j3a}R^{2221}$, 13 $SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-C(=S)OR^{2221}$, $-C(=O)SR^{2221}$, $-NR^{2221}C(=NR^{3331})NR^{2221a}R^{3331a}$, $-NR^{2221}C(=NR^{3331})OR^{2221a}$, $-NR^{2221}C(=NR^{3331})SR^{2221a}$, $-OC(=O)OR^{2221}$, $-OC(=O)NR^{2221}R^{3331}$, $-OC(=O)SR^{2221}$, $-SC(=O)OR^{2221}$, or $-SC(=O)NR^{2221}R^{3331}$ substituents; and the other variables are described as above for Formula I.

In an embodiment of this third aspect, a compound is represented by Formula I, or a pharmaceutically acceptable salt thereof, wherein $R^1$ is heterocyclyl optionally substituted by one or more independent $G^{11}$ substituents; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$ or $-CR^5R^6-$, $-S(O)_{j4}-$, or $-C(O)-$; wherein n and m are both 1; wherein $R^4$ is $C_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent $G^{41}$ substituents;

wherein $G^{11}$ is $-OR^{21}$, $-NR^{21}R^{31}$, $-CO_2R^{21}$, $-C(O)R^{21}$, $-CONR^{21}R^{31}$, $-NR^{21}C(=O)R^{31}$, $-NR^{21}C(=O)OR^{31}$, $-NR^{21}C(=O)NR^{31}R^{21a}$, $-NR^{21}S(O)_{j3}R^{31}$, $-OC(=O)OR^{21}$, $-OC(=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, $-CF_3$, $-OCF_3$, $-OR^{2221}$, $-NR^{2221}R^{3331}(R^{2221a})_{j3a}$, $-C(O)R^{2221}$, $-CO_2R^{2221}$, $-CONR^{2221}R^{3331}$, $-NO_2$, $-CN$, $-S(O)_{j3a}R^{2221}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-C(=S)OR^{2221}$, $-C(=O)SR^{2221}$, $-NR^{2221}C(=NR^{3331})NR^{2221a}R^{3331a}$, $-NR^{2221}C(=NR^{3331})OR^{2221a}$, $-NR^{2221}C(=NR^{3331})SR^{222a}$, $-OC(=O)OR^{2221}$, $-OC(=O)NR^{2221}R^{3331}$, $-OC(=O)SR^{2221}$, $-SC(=O)OR^{2221}$, or $-SC(=O)NR^{2221}R^{3331}$ substituents; and the other variables are described as above for Formula I.

In an embodiment of this third aspect, a compound is represented by Formula I, or a pharmaceutically acceptable salt thereof, wherein $R^1$ is represented by the structural formula:

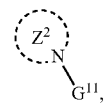

wherein $Z^2$ is a heterocyclyl containing a N substituted by $G^{11}$ and the other variables are described as above for Formula I.

In an embodiment of this third aspect, a compound is represented by Formula I, or a pharmaceutically acceptable salt thereof, wherein $R^1$ is represented by the structural formula:

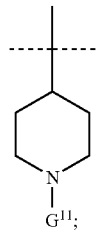

wherein $G^{11}$ is —C(O)$R^{21}$, —CO$_2R^{21}$, —CONR$^{21}R^{31}$, —SO$_2$NR$^{21}R^{31}$, —S(O)$_{j3}R^{31}$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{2221}$, —NR$^{2221}R^{3331}$, —OC(O)R$^{2221}$, —CO$_2R^{2221}$, —CONR$^{2221}R^{3331}$, —SO$_2$NR$^{2221}R^{3331}$, —NR$^{2221}$C(=O)R$^{3331}$, NR$^{2221}$C(=O)OR$^{3331}$, —NR$^{2221}$C(=O)NR$^{3331}R^{2221a}$, —NR$^{2221}$S(O)$_{j3a}R^{3331}$, —NR$^{2221}$C(=NR$^{3331}$)NR$^{2221a}R^{3331a}$, or —OC(=O)NR$^{2221}R^{3331}$ substituents;

or $G^{11}$ is aryl-C$_{0-10}$alkyl or hetaryl-C$_{0-10}$alkyl, any of which is optionally substituted with one or more independent halo, —CF$_3$, —OCF$_3$, —OR$^{2221}$, —NR$^{2221}R^{3331}$, —C(O)R$^{2221}$, —CO$_2R^{2221}$, —CONR$^{2221}R^{3331}$, —SO$_2$NR$^{2221}R^{3331}$, —NR$^{2221}$C(=O)R$^{3331}$, —NR$^{2221}$C(=O)OR$^{3331}$, —NR$^{2221}$C(=O)NR$^{3331}R^{2221a}$, —NR$^{2221}$S(O)$_{j3a}R^{3331}$, —NR$^{2221}$C(=NR$^{3331}$)NR$^{2221a}R^{3331a}$, or —OC(=O)NR$^{2221}R^{3331}$ substituents; and the other variables are described as above for Formula I.

In an embodiment of this third aspect, a compound is represented by Formula I, or a pharmaceutically acceptable salt thereof, wherein $R^1$ is represented by the structural formula:

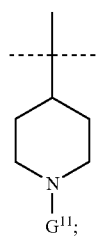

wherein $G^{11}$ is —C(O)$R^{21}$, —CO$_2R^{21}$, —CONR$^{21}R^{31}$, —SO$_2$NR$^{21}R^{31}$, —S(O)$_{j3}R^{31}$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{2221}$, —N$^{2221}R^{3331}$, —C(O)R$^{2221}$, —CO$_2R^{2221}$, —CONR$^{2221}R^{3331}$, —SO$_2$NR$^{2221}R^{3331}$, —NR$^{2221}$C(=O)R$^{3331}$, —NR$^{2221}$C(=O)OR$^{3331}$, —NR$^{2221}$C(=O)NR$^{3331}R^{2221a}$, —NR$^{2221}$S(O)$_{j3a}R^{3331}$, —NR$^{2221}$C (=NR$^{3331}$)NR$^{2221a}R^{3331a}$, or —OC(=O)NR$^{2221}R^{3331}$ substituents; and the other variables are described as above for Formula I.

In an embodiment of this third aspect, a compound is represented by Formula I, or a pharmaceutically acceptable salt thereof, above wherein $R^1$ is represented by the structural formula:

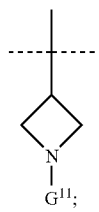

wherein $G^{11}$ is —C(O)$R^{21}$, —CO$_2R^{21}$, —CONR$^{21}R^{31}$, —SO$_2$NR$^{21}R^{31}$, —S(O)$_{j3}R^{31}$, C$_{0-10}$alkyl, C$_{2-1}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{2221}$, —NR$^{2221}R^{3331}$, —C(O)R$^{2221}$, —CO$_2R^{2221}$, —CONR$^{2221}R^{3331}$, —SO$_2$NR$^{2221}R^{3331}$, —NR$^{2221}$C(=O)R$^{3331}$, NR$^{2221}$C(=O)OR$^{3331}$, —NR$^{2221}$C(=O)NR$^{2221}R^{3331}$, —NR$^{2221}$S(O)$_{j3a}R^{3331}$, —NR$^{2221}$C(=NR$^{3331}$)NR$^{2221a}R^{3331a}$, or —OC(=O)NR$^{2221}R^{3331}$ substituents;

or aryl-C$_{0-10}$alkyl or hetaryl-C$_{0-10}$alkyl, any of which is optionally substituted with one or more independent halo, —CF$_3$, —CF$_3$, —OR$^{2221}$, —NR$^{2221}R^{3331}$, —C(O)R$^{2221}$, —CO$_2R^{2221}$, —CONR$^{2221}R^{3331}$, —SO$_2$NR$^{2221}R^{3331}$, —NR$^{2221}$C(=O)R$^{3331}$, —NR$^{2221}$C(=O)OR$^{3331}$, —NR$^{2221}$C(=O)NR$^{2221}R^{3331}$, —NR$^{2221}$S(O)$_{j3a}R^{3331}$, —NR$^{2221}$C(=NR$^{3331}$)NR$^{2221a}R^{3331a}$, or —OC(=O)NR$^{2221}R^{3331}$ substituents; and the other variables are described as above for Formula I.

In an embodiment of this third aspect, a compound is represented by Formula I, or a pharmaceutically acceptable salt thereof, wherein $R^1$ is represented by the structural formula:

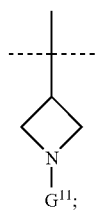

wherein $G^{11}$ is —C(O)$R^{21}$, —CO$_2R^{21}$, —CONR$^{21}R^{31}$, —SO$_2$NR$^{21}R^{31}$, —S(O)$_{j3}R^{31}$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —O$^{2221}$, —NR$^{2221}R^{3331}$, —C(O)R$^{2221}$, —CO$_2R^{2221}$, —CONR$^{2221}R^{3331}$, —SO$_2$NR$^{2221}R^{3331}$, —NR$^{2221}$C(=O)R$^{3331}$, —NR$^{2221}$C(=O)OR$^{3331}$, —NR$^{2221}$C(=O)NR$^{2221}R^{3331}$, —NR$^{2221}$S(O)$_{j3a}R^{3331}$, —NR$^{2221}$C (=NR$^{3331}$)NR$^{2221a}$R$^{3331a}$, or —OC(=O)NR$^{2221}$R$^{3331}$ substituents; and the other variables are described as above for Formula I.

In a fourth aspect of the present invention, a compound is represented by Formula I, or a pharmaceutically acceptable salt thereof, wherein R$^1$ is cycloC$_{3-10}$alkyl optionally substituted by one or more independent G$^{11}$ substituents and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is aryl$^1$ or heteroaryl$^1$, any of which is optionally substituted by one or more independent G$^{10}$ substituents; and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is heteroaryl$^1$, which is optionally substituted by one or more independent G$^{10}$ substituents; and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is aryl$^1$, which is optionally substituted by one or more independent G$^{10}$ substituents; and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is heteroaryl$^1$, which is optionally substituted by one or more independent G$^{10}$ substituents;
wherein G$^{10}$ is halo, —OR$^2$, —NR$^2$R$^3$, —C(O)R$^2$, —CO$_2$R$^2$, —CONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)OR$^2$, —OC(=O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocylylo-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$(C=O)NR$^{333}$R$^{222a}$, —NR$^{222}$S(O)$_{j1a}$R$^{333}$, —NR$^{222}$C(=NR$^{333}$)NR$^{222a}$R$^{333a}$, or —O(C=O)NR$^{222}$R$^{333}$ substituents; or G$^{11}$ is —(X$^1$)$_n$—(Y$^1$)$_m$—R$^4$; or G$^{10}$ is aryl-C$_{0-10}$alkyl or hetaryl-C$_{0-10}$alkyl, any of which is optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$ C(=O)R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —NR$^{222}$C(=NR$^{333}$)NR$^{222a}$R$^{333a}$, or —OC(=O)NR$^{222}$R$^{333}$ substituents; and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is aryl$^1$ optionally substituted by one or more independent G$^{10}$ substituents;
wherein G$^{10}$ is halo, —OR$^2$, —NR$^2$R$^3$, —C(O)R$^2$, —CO$_2$R$^2$, —ONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$(C=O)NR$^{333}$R$^{222a}$, —NR$^{222}$S(O)$_{j1a}$R$^{333}$, —NR$^{222}$C(=NR$^{333}$)NR$^{222a}$R$^{333a}$, or —OC(=O)NR$^{222}$R$^{333}$ substituents; or G$^{10}$ is —(X$^1$)$_n$—(Y$^1$)—R$^4$; or G$^{10}$ is aryl-C$_{0-10}$alkyl or hetaryl-C$_{0-10}$alkyl, any of which is optionally substituted with one or more independent halo, —CF$_3$, —OCF$_3$, —OR$^{222}$, —NR$^{222}$R$^{333}$, —C(O) R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —NR$^{222}$C(=NR$^{333}$)NR$^{222a}$R$^{333a}$, or —OC(=O)NR$^{222}$R$^{333}$ substituents; and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is aryl$^1$, which is optionally substituted by one or more independent G$^{10}$ substituents;
wherein G$^{10}$ is halo, —OR$^2$, —NR$^2$R$^3$, —C(O)R$^2$, —CO$_2$R$^2$, —CONR$^2$R$^3$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —OC(=O)OR$^2$, —OC(=O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more indepndent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, —NR$^{222}$C(=O)R$^{333}$, —NR$^{222}$C(=O)OR$^{333}$, —N$^{222}$C(=O)NR$^{333}$R$^{222a}$, —NR$^{222}$S(O)$_{j1a}$R$^{333}$, —NR$^{222}$C(=NR$^{333}$)NR$^{222a}$R$^{333a}$ or —OC(=O)NR$^{222}$R$^{333}$ substituents; or G$^{11}$ is —(X$^1$)$_n$—(Y$^1$)$_m$—R$^4$; and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is substituted by said one to five independent G$^{10}$ substituents wherein at least one of said G$^{10}$ substituents is —(X$^1$)$_n$—(Y$^1$)$_m$—R$^4$; and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—; and the other variables are described as above for Formula I.

In an embodiment of this fourth aspect, a compound is represented by Formula I, or a pharmaceutically acceptable salt thereof, wherein R$^1$ is cycloC$_{3-10}$alkyl optionally substituted by one or more independent G$^{11}$ substituents; wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is substituted by said one to five independent $G^{10}$ substituents wherein at least one of said $G^{10}$ substituents is —$(X^1)_n$—$(Y^1)_m$—$R^4$, and wherein $X^1$ and $Y^1$ are each independently —O— or —$CH_2$—; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is substituted by said one to five independent $G^{10}$ substituents wherein at least one of said $G^{10}$ substituents is —$(X^1)_n$—$(Y^1)_m$—$R^4$; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O—, —$NR^7$—, —$CR^5R^6$—, —$S(O)_{j4}$—, or —C(O)—; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O— or —$CR^5R^6$—; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O— or —$CH_2$—; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O—, —$NR^7$—, —$CR^5R^6$—, —$S(O)_{j4}$—, or —C(O)—; wherein $R^4$ is aryl or heteroaryl, any of which is optionally substituted by one or more independent $G^{41}$ substituents; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is aryl$^1$ substituted by said one to five independent $G^{10}$ substituents wherein at least one of said $G^{10}$ substituents is —$(X^1)_n$—$(Y^1)_m$—$R^4$; wherein n and m are both 1; wherein $R^4$ is aryl optionally substituted by one or more $G^{41}$ substituents; $X^1$ is —O—; $Y^1$ is —$CH_2$—; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is substituted by said one to five independent $G^{10}$ substituents wherein at least one of said $G^{10}$ substituents is —$(X^1)_n$—$(Y^1)_m$—$R^4$; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents;

wherein $G^{11}$ is —$OR^{21}$, —$NR^{21}R^{31}$, —$CO_2R^{21}$, —$C(O)R^{21}$, —$CONR^{21}R^{31}$, —$NR^{21}C(=O)R^{31}$, —$NR^{21}C(=O)OR^{31}$, —$NR^{21}C(=O)NR^{31}R^{21a}$, —$NR^{21}S(O)_{j3}R^{31}$, —$OC(=O)OR^{21}$, —$OC(=O)NR^{21}R^{31}$, $C_{0-10}$alkyl, cyclo-$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, —$CF_3$, —$OCF_3$, —$OR^{2221}$, $NR^{2221}R^{3331}(R^{2221a})_{j3a}$, —$C(O)R^{2221}$, —$CO_2R^{2221}$, —$CONR^{2221}R^{3331}$, —$NO_2$, —CN, —$S(O)_{j3a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{2221a}$, —$NR^{2221}S(O)_{j3a}R^{3331}$, —$C(=S)OR^{2221}$, —$C(=O)SR^{2221}$, —$NR^{2221}C(=NR^{3331})NR^{2221a}R^{3331a}$, —$NR^{2221}C(=NR^{3331})OR^{2221a}$, —$NR^{2221}C(=NR^{3331})SR^{2221a}$, —$OC(=O)OR^{2221}$, —$OC(=O)NR^{2221}R^{3331}$, —$OC(=O)SR^{2221}$, —$SC(=O)OR^{2221}$, or —$SC(=O)NR^{2221}R^{3331}$ substituents; and the other variables are described as above for Formula I.

In an embodiment of this fourth aspect, a compound is represented by Formula I, or a pharmaceutically acceptable salt thereof, wherein $R^1$ is cyclo$C_{3-10}$alkyl optionally substituted by one or more independent $G^{11}$ substituents; wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O—, —$NR^7$—, —$CR^5R^6$—, —$S(O)_{j4}$—, or —C(O)—; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents;

wherein $G^{11}$ is —$OR^{21}$, —$NR^{21}R^{31}$, —$CO_2R^{21}$, —$C(O)R^{21}$, —$CONR^{21}R^{31}$, —$NR^{21}C(=O)R^{31}$, —$NR^{21}C(=O)OR^{31}$, —$NR^{21}C(=O)NR^{31}R^{21a}$, —$NR^{21}S(O)_{j3}R^{31}$, —$OC(=O)OR^{21}$, —$OC(=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, —$CF_3$, —$OCF_3$, —$OR^{2221}$, $NR^{2221}R^{3331}(R^{2221a})_{j3a}$, —$C(O)R^{2221}$, —$CO_2R^{2221}$, —$CONR^{2221}R^{3331}$, —$NO_2$, —CN, —$S(O)_{j3a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{2221a}$, —$NR^{2221}S(O)_{j3a}R^{3331}$, —$C(=S)OR^{2221}$, —$C(=O)SR^{2221}$, —$NR^{2221}C(=NR^{3331})NR^{2221a}R^{3331a}$, —$NR^{2221}C(=NR^{3331})OR^{2221a}$, —$NR^{2221}C(=NR^{3331})$ $SR^{2221a}$, $-OC(=O)OR^{2221}$, $-OC(=O)NR^{2221}R^{3331}$, $-OC(=O)SR^{2221}$, $-SC(=O)OR^{2221}$, or $-SC(=O)NR^{2221}R^{3331}$ substituents; and the other variables are described as above for Formula I.

In an embodiment of this fourth aspect, a compound is represented by Formula I, or a pharmaceutically acceptable salt thereof, wherein $R^1$ is cycloC$_{3-10}$alkyl optionally substituted by one or more independent $G^{11}$ substituents; wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$ or $-CR^5R^6-$; wherein $R^4$ is $C_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent $G^{41}$ substituents;

wherein $G^{11}$ is $-OR^{21}$, $-NR^{21}R^{31}$, $-CO_2R^{21}$, $-C(O)R^{21}$, $-CONR^{21}R^{31}$, $-NR^{21}C(=O)R^{31}$, $-NR^{21}C(=O)OR^{31}$, $-NR^{21}C(=O)NR^{31}R^{21a}$, $-NR^{21}S(O)_{j3}R^{31}$, $-OC(=O)OR^{21}$, $-OC(=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, $-CF_3$, $-OCF_3$, $-OR^{2221}$, $-NR^{2221}R^{3331}(R^{222a})_{j3a}$, $-C(O)R^{2221}$, $-CO_2R^{2221}$, $-CONR^{2221}R^{3331}$, $-NO_2$, $-CN$, $-S(O)_{j3a}R^{2221}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-C(=S)OR^{2221}$, $-C(=O)SR^{2221}$, $-NR^{2221}C(=NR^{3331})NR^{222a}R^{3331a}$, $-NR^{2221}C(=NR^{3331})OR^{2221a}$, $-NR^{2221}C(=NR^{3331})SR^{2221a}$, $-OC(=O)OR^{2221}$, $-OC(=O)NR^{2221}R^{3331}$, $-OC(=O)SR^{2221}$, $-SC(=O)OR^{2221}$, or $-SC(=O)NR^{2221}R^{3331}$ substituents; and the other variables are described as above for Formula I.

In an embodiment of this fourth aspect, a compound is represented by Formula I, or a pharmaceutically acceptable salt thereof, wherein $R^1$ is cycloC$_{3-10}$alkyl optionally substituted by one or more independent $G^{11}$ substituents; wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$ or $-CH_2-$; wherein $R^4$ is $C_{0-10}$alkyl, aryl, heteroaryl, cycloC$_{3-10}$alkyl, heterocyclyl, cycloC$_{3-10}$alkenyl, or heterocycloalkenyl, any of which is optionally substituted by one or more independent $G^{41}$ substituents;

wherein $G^{11}$ is $-OR^{21}$, $-NR^{21}R^{31}$, $-CO_2R^{21}$, $-C(O)R^{21}$, $-CONR^{21}R^{31}$, $-NR^{21}C(=O)R^{31}$, $-NR^{21}C(=O)OR^{31}$, $-NR^{21}C(=O)NR^{31}R^{21a}$, $-NR^{21}S(O)_{j3}R^{31}$, $-OC(=O)OR^{21}$, $-OC(=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, $-CF_3$, $-OCF_3$, $-OR^{2221}$, $-NR^{2221}R^{3331}(R^{2221a})_{j3a}$, $-C(O)R^{2221}$, $-CO_2R^{2221}$, $-CONR^{2221}R^{3331}$, $-NO_2$, $-CN$, $-S(O)_{j3a}R^{2221}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-C(=S)OR^{2221}$, $-C(=O)SR^{2221}$, $-NR^{2221}C(=NR^{3331})NR^{2221a}R^{3331a}$, $-NR^{2221}C(=NR^{3331})OR^{2221a}$, $-NR^{2221}C(=NR^{3331})SR^{2221a}$, $-OC(=O)OR^{2221}$, $-OC(=O)NR^{2221}R^{3331}$, $-OC(=O)SR^{2221}$, $-SC(=O)OR^{2221}$, or $-SC(=O)NR^{2221}R^{3331}$ substituents; and the other variables are described as above for Formula I.

In a fifth aspect of the present invention, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; any of which is optionally substituted by one or more independent $G^{10}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is heteroaryl$^1$, which is optionally substituted by one or more independent $G^{10}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$, which is optionally substituted by one or more independent $G^{10}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is heteroaryl$^1$, which is optionally substituted by one or more independent $G^{10}$ substituents;

wherein $G^{10}$ is halo, $-OR^2$, $-NR^2R^3$, $-C(O)R^2$, $-CO_2R^2$, $-CONR^2R^3$, $-SO_2NR^2R^3$, $-NR^2C(=O)R^3$, $-NR^2C(=O)OR^3$, $-NR^2C(=O)NR^3R^{2a}$, $-NR^2S(O)_{j1}R^3$, $-OC(=O)OR^2$, $-OC(=O)NR^2R^3$, $C_{0-10}$alkyl, $C_{2-10}$alkenyl, $C_{1-10}$alkoxyC$_{1-10}$alkyl, $C_{1-10}$alkylthioC,-Ioalkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2NR^{222}R^{333}$, $-NR^{22}C(=O)R^{333}$, $-NR^{222}C(=O)OR^{333}$, $-NR^{222}C(=O)NR^{333}R^{222a}$, $-NR^{222}S(O)_{j1a}R^{333}$, $-NR^{222}C(=NR^{333})NR^{222a}R^{333a}$, or $-O(C=O)NR^{222}R^{333}$ substituents; or $G^{11}$ is $-(X^1)_n-(Y^1)_m-R^4$; or $G^{10}$ is aryl-C$_{0-10}$alkyl or hetaryl-C$_{0-10}$alkyl, any of which is optionally substituted with one or more independent halo, $-CF_3$, $-OCF_3$, $-OR^{222}$, $-NR^{222}R^{333}$, $-C(O)R^{222}$, $-O_2R^{222}$, $-CONR^{222}R^{333}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(O)_{j2a}R^{333}$, $-NR^{222}C(=NR^{333})NR^{222a}R^{333a}$, or $-OC(=O)NR^{222}R^{333}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$, which is optionally substituted by one or more independent $G^{10}$ substituents;

wherein $G^{10}$ is halo, $-OR^2$, $-NR^2R^3$, $-C(O)R^2$, $-CO_2R^2$, $-CONR^2R^3$, $-SO_2NR^2R^3$, $-NR^2C(=O)R^3$, $-NR^2C(=O)OR^3$, $-NR^2C(=O)NR^3R^{2a}$, $-NR^2S(O)_{j1}R^3$, $-OC(=O)OR^2$, $-OC(=O)NR^2R^3$, $C_{0-10}$alkyl, $C_{2-10}$alkenyl, $C_{1-10}$alkoxyC$_{1-10}$alkyl, $C_{1-10}$alkylthioC$_{1-10}$alkyl, cycloC$_{3-8}$alkyl, cycloC$_{3-8}$alkenyl, heterocyclyl-$C_{0-10}$alkyl, or heterocyclyl-$C_{2-10}$alkenyl, any of which is optionally substituted with one or more independent oxo, —$CF_3$, —$OCF_3$, —$OR^{222}$, —$NR^{222}R^{333}$, —$C(O)R^{222}$, —$CO_2R^{222}$, —$CONR^{222}R^{333}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(O)_{j1a}R^{333}$, —$NR^{222}C(=NR^{333})NR^{222a}R^{333a}$, or —$O(C=O)NR^{222}R^{333}$ substituents; or $G^{11}$ is —$(X^1)_n$—$(Y^1)_m$—$R^4$; or $G^{10}$ is aryl-$C_{0-10}$alkyl or hetaryl-$C_{0-10}$alkyl, any of which is optionally substituted with one or more independent halo, —$CF_3$, —$OCF_3$, —$OR^{222}$, —$NR^{222}R^{333}$, —$C(O)R^{222}$, —$CO_2R^{222}$, —$CONR^{222}R^{333}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(O)_{j2a}R^{333}$, —$NR^{222}C(=NR^{333})NR^{222a}R^{333a}$, or —$OC(=O)NR^{222}R^{333}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is heteroaryl$^1$, which is optionally substituted by one or more independent $G^{10}$ substituents;
wherein $G^{10}$ is halo, —$OR^2$, —$NR^2R^3$, —$C(O)R^2$, —$CO_2R^2$, —$CONR^2R^3$, —$SO_2NR^2R^3$, —$NR^2C(=O)R^3$, —$NR^2C(O)OR^3$, —$NR^2C(=O)NR^3R^{2a}$, —$NR^2S(O)_{j1}R^3$, —$OC(=O)OR^2$, —$OC(=O)NR^2R^3$, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent oxo, —$CF_3$, —$OCF_3$, —$OR^{222}$, —$NR^{222}R^{333}$, —$C(O)R^{222}$, —$CO_2R^{222}$, —$CONR^{222}R^{333}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(O)_{j1a}R^{333}$, —$NR^{222}C(=NR^{333})NR^{222a}R^{333a}$, or —$OC(=O)NR^{222}R^{333}$ substituents; or $G^{10}$ is —$(X^1)_n$—$(Y^1)_m$—R4; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$, which is optionally substituted by one or more independent $G^{10}$ substituents;
wherein $G^{10}$ is halo, —$OR^2$, —$NR^2R^3$, —$C(O)R^2$, —$CO_2R^2$, —$CONR^2R^3$, —$SO_2NR^2R^3$, —$NR^2C(=O)R^3$, —$NR^2C(=O)OR^3$, —$NR^2C(=O)NR^3R^{2a}$, —$NR^2S(O)_{j1}R^3$, —$OC(=O)OR^2$, —$OC(=O)NR^2R^3$, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent oxo, —$CF_3$, —$OCF_3$, —$OR^{222}$, —$NR^{222}R^{333}$, —$C(O)R^{222}$, —$CO_2R^{222}$, —$CONR^{222R333}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(O)_{j1a}R^{333}$, —$NR^{222}C(=NR^{333})NR^{222a}R^{333a}$, or —$OC(=O)NR^{222}R^{333}$ substituents; or $G^{11}$ is —$(X^1)_n$—$(Y^1)_m$—$R^4$; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein n and m are both 1; and the other variables are described as above for Formula I.

In an embodiment of this fifth aspect, a compound is represented by Formnula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O—, —$NR^7$—, —$CR^5R^6$—, —$S(O)_{j4}$—, or —C(O)—; wherein n and m are both 1; j4 is 1 or 2; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O— or —$CR^5R^6$—; wherein n and m are both 1; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O— or —$CH_2$—; wherein n and m are both 1; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein n and m are both 1; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is —$(X^1)_n$—$(Y^1)_m$—$R^4$; wherein $X^1$ and $Y^1$ are each independently —O—, —NR—, —$CR^5R^6$—, —$S(O)_{j4}$—, or —C(O)—; wherein n and m are both 1; j4 is 1 or 2; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$ or $-CR^5R^6-$; wherein n and m are both 1; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$ or $-CH_2-$; wherein n and m are both 1; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein n and m are both 1; wherein $R^4$ is aryl or heteroaryl, any of which is optionally substituted by one or more independent $G^{41}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$, $-NR^7-$, $-CR^5R^6-$, $-S(O)_{j4}-$, or $-C(O)-$; wherein n and m are both 1; j4 is 1 or 2; wherein $R^4$ is aryl or heteroaryl, any of which is optionally substituted by one or more independent $G^{41}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_m-(Y^1)_m-R^4$; wherein $X^1$ and $Y^1$ are each independently $-O-$ or $-CR^5R^6-$; wherein n and m are both 1; wherein $R^4$ is aryl or heteroaryl, any of which is optionally substituted by one or more independent $G^{41}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$ or $-CH_2-$; wherein n and m are both 1; wherein $R^4$ is aryl or heteroaryl, any of which is optionally substituted by one or more independent $G^{41}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ substituted by said one to five independent $G^{10}$ substituents wherein at least one of said $G^{10}$ substituents is $-(X^1)_n-(Y^1)_m-R^4$; n and m are both 1; $R^4$ is aryl optionally substituted by one or more $G^{41}$ substituents; $X^1$ is $-O-$; $Y^1$ is $-CH_2-$; and the other variables are described as above for Formula I.

In an embodiment of this fifth aspect, a compound is represented by Formula I, or a pharmaceutically acceptable salt thereof, wherein $R^1$ is cis- or trans-cyclobutyl which is substituted at the 3-position by $G^{11}$; wherein $Q^1$ is aryl$^1$ substituted by said one to five independent $G^{10}$ substituents wherein at least one of said $G^{10}$ substituents is $-(X^1)_n-(Y^1)_m-R^4$; n and m are both 1; $R^4$ is aryl optionally substituted by one or more $G^{41}$ substituents; $X^1$ is $-O-$; and $Y^1$ is $-CH_2-$; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is aryl$^1$ or heteroaryl$^1$, wherein $Q^1$ is substituted by said one to five independent $G^{10}$ substituents wherein at least one of said $G^{10}$ substituents is $-(X^1)_n-(Y^1)_m-R^4$; wherein n and m are both 1; wherein $R^4$ is $C_{0-10}$alkyl, aryl, heteroaryl, cyclo$C_{3-10}$alkyl, heterocyclyl, cyclo$C_{3-10}$alkenyl, or heterocycloalkenyl, any of which is optionally substituted by one or more independent $G^{41}$ substituents;

wherein $G^{11}$ is $-OR^{21}$, $-NR^{21}R^{31}$, $-CO_2R^{21}$, $-C(O)R^{21}$, $-CONR^{21}R^{31}$, $-NR^{21}C(=O)R^{31}$, $-NR^{21}C(=O)OR^{31}$, $NR^{21}C(=O)NR^{31}R^{21a}$, $-NR^{21}S(O)_{j3}R^{31}$, $-OC(=O)OR^{21}$, $-OC(=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $-CF_3$, $-OCF_3$, $-OR^{2221}$, $-NR^{2221}R^{3331}(R^{222a})_{j3a}$, $-(O)R^{2221}$, $-CO_2R^{2221}$, $-CONR^{2221}R^{3331}$, $-NO_2$, $-CN$, $-S(O)_{j3a}R^{2221}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-C(=S)OR^{2221}$, $-C(=O)SR^{2221}$, $-NR^{2221}C(=NR^{3331})NR^{2221a}R^{3331a}$, $-NR^{2221}C(=NR^{3331})OR^{2221a}$, $-NR^{2221}C(=NR^{3331})SR^{2221a}$, $-OC(=O)OR^{2221}$, $-OC(=O)NR^{2221}R^{3331}$, $-OC(=O)SR^{2221}$, $-SC(=O)OR^{2221}$, or $-SC(=O)NR^{2221}R^{3331}$ substituents; and the other variables are described as above for Formula I.

In an embodiment of this fifth aspect, a compound is represented by Formula I, or a pharmaceutically acceptable salt thereof, wherein $R^1$ is cis- or trans-cyclobutyl substituted at the 3-position by $G^{11}$ or $R^1$ is cis- or trans-cyclohexyl substituted at the 4-position by $G^{11}$; wherein $Q^1$ is substituted by said one to five independent $G^{10}$ substituents wherein at least one of said $G^{10}$ substituents is $-(X^1)_n-(Y^1)_m-R^4$; wherein $X^1$ and $Y^1$ are each independently $-O-$, $-NR^7-$, —CR$^5$R$^6$—, —S(O)$_{j4}$—, or —C(O)—; wherein n and m are both 1; j4 is 1 or 2; and the other variables are described as above for Formula I.

In an embodiment of this fifth aspect, a compound is represented by Formula I, or a pharmaceutically acceptable salt thereof, wherein R$^1$ is cis- or trans-cyclobutyl substituted at the 3-position by G$^{11}$ or R$^1$ is cis- or trans-cyclohexyl substituted at the 4-position by G$^{11}$; wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—; wherein n and m are both 1; and the other variables are described as above for Formula I.

In an embodiment of this fifth aspect, a compound is represented by Formula I, or a pharmaceutically acceptable salt thereof, wherein R$^1$ is cis- or trans-cyclobutyl substituted at the 3-position by G$^{11}$ or R$^1$ is cis- or trans-cyclohexyl substituted at the 4-position by G$^{11}$; wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O—, —NR$^7$—, —CR$^5$R$^6$—, —S(O)$_{j4}$—, or —C(O)—;

wherein G$^{11}$ is —OR$^{21}$, NR$^{21}$R$^{31}$(R$^{21a}$)$_3$, —C(O)R$^{21}$, —CO$_2$R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{21}$R$^{31}$, —NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{333a}$)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{2221}$R$^{3331}$, —NR$^{2221}$S(O)$_{j3a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{3331a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents;

or G$^{11}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{2221a}$)$_{j3a}$, —C(O)R$^{2221}$, —CO$_2$R$^{2221}$R$^{33331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, —NR$^{2221}$C(=NR$^{3331}$)N$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this fifth aspect, a compound is represented by Formula I, or a pharmaceutically acceptable salt thereof, wherein R$^1$ is cis- or trans-cyclobutyl substituted at the 3-position by G$^{11}$ or R$^1$ is cis- or trans-cyclohexyl substituted at the 4-position by G$^{11}$; wherein Q$^1$ is substituted by said one to five independent G$^{10}$ substituents wherein at least one of said G$^{10}$ substituents is —(X$^1$)$_n$—(Y$^1$)$_m$—R$^4$; wherein X$^1$ and Y$^1$ are each independently —O— or —CR$^5$R$^6$—; and wherein n and m are both 1; j4 is 1 or 2;

wherein G$^{11}$ is —OR$^{21}$, —NR$^{21}$R$^{31}$(R$^{21a}$)$_{j3}$, —C(O)R$^{21}$, —CO$_2$R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{21}$R$^{31}$, NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with-one or more independent halo, oxo, —CF$_3$, —OCF$_3$, —OR$^{2221}$, —NR$^{2221}$R$^{3331}$(R$^{333a}$)$_{j3a}$, —C(O)R$^{2221}$, —CO$_2$R$^{2221}$, CONR$^{2221}$R$^{3331}$, —NO$_2$, —CN, —S(O)$_{j3a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{2221}$R$^{3331}$, —NR$^{2221}$S(O)$_{j3a}$R$^{3331}$, —C(=S)OR$^{2221}$, —C(=O)SR$^{2221}$, —N$^{2221}$C(=NR$^{3331}$)NR$^{2221a}$R$^{3331a}$, —N$^{2221}$C(=NR$^{3331}$)OR$^{2221a}$, —NR$^{2221}$C(=NR$^{3331}$)SR$^{3331a}$, —OC(=O)OR$^{2221}$, —OC(=O)NR$^{2221}$R$^{3331}$, —OC(=O)SR$^{2221}$, —SC(=O)OR$^{2221}$, or —SC(=O)NRR$^{222}$R$^{3331}$ substituents;

or G$^{11}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{2221a}$)$_{j3a}$, —C(O)R$^{2221}$, —CONR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{222}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In a sixth aspect of the present invention, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—) or 4-(—O—); m is 1; Y$^1$ is (—CH$_2$—); R$^4$ is aryl optionally substituted by one or more independent G$^{41}$ substituents; and the other variables are described as above for Formula I.

In an embodiment of this sixth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—) or 4-(—O—); m is 1; Y$^1$ is (—CH$_2$—); and R$^4$ is aryl optionally substituted by one or more independent G$^{41}$ substituents; wherein R$^1$ is aryl, heteroaryl, cycloC$_{3-10}$alkyl or heterocyclyl, any of which is optionally substituted by one or more independent G$^{11}$ substituents; and the other variables are described as above for Formula I.

In an embodiment of this sixth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3 —(—O—) or 4 —(—O—); m is 1; Y$^1$ is (—CH$_2$—); R$^4$ is aryl optionally substituted by one or more independent G$^{41}$ substituents; wherein R$^1$ is cycloC$_{3-10}$alkyl or heterocyclyl, any of which is optionally substituted by one or more independent G$^{11}$ substituents; and the other variables are described as above for Formula I.

In an embodiment of this sixth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3 —(—O—) or 4 —(—O—); m is 1; Y$^1$ is (—CH$_2$—); R$^4$ is aryl optionally substituted by one or more independent G$^{41}$ substituents; wherein R$^1$ is cycloC$_{3-10}$alkyl, optionally substituted by one or more independent G$^{11}$ substituents; and the other variables are described as above for Formula I.

In an embodiment of this sixth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—) or 4(—O—); m is 1; $Y^1$ is (—CH$_2$—); and $R^4$ is aryl optionally substituted by one or more independent $G^{41}$ substituents; wherein $R^1$ is cyclobutyl, cyclopentyl, or cyclohexyl, any of which is optionally substituted by one or more independent $G^{11}$ substituents; and the other variables are described as above for Formula I.

In an embodiment of this sixth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—) or 4-(—O—); m is 1; $Y^1$ is (—CH$_2$—); and $R^4$ is aryl optionally substituted by one or more independent $G^{41}$ substituents; wherein $R^1$ is cycloC$_{3-10}$alkyl, optionally substituted by one or more independent $G^{11}$ substituents;

wherein $G^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, —NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221}$)$_{j3a}$, —C(O)R$^{2221}$, —CO$_2$R$^{2221}$, —CONR$^{2221}$R$^{3331}$, —NO$_2$, —CN, S(O)$_{j3a}$R$^{2221}$, —SO$_2$NR$^{2221}$R$^{3331}$, NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this sixth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—) or 4-(—O—); m is 1; $Y^1$ is (—CH$_2$—); $R^4$ is aryl optionally substituted by one or more independent $G^{41}$ substituents; wherein $R^1$ is cyclobutyl, cyclopentyl, or cyclohexyl, any of which is optionally substituted by one or more independent $G^{11}$ substituents;

wherein $G^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, —NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{222a}$)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=C)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In a seventh aspect of the present invention, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—); m is 0; $R^4$ is C$_{0-8}$alkyl or cycloC$_{3-10}$alkyl, any of which is optionally substituted by one or more independent $G^{41}$ substituents; and the other variables are described as above for Formula I.

In an embodiment of this seventh aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—); m is 0; $R^4$ is C$_{0-8}$alkyl or cycloC$_{3-10}$alkyl, any of which is optionally substituted by one or more independent $G^{41}$ substituents; wherein $R^1$ is aryl, heteroaryl, cycloC$_{3-10}$alkyl, or heterocyclyl, any of which is optionally substituted by one or more independent $G^{11}$ substituents; and the other variables are described as above for Formula I.

In an embodiment of this seventh aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—); m is 0; $R^4$ is C$_{0-8}$alkyl or cycloC$_{3-10}$alkyl, any of which is optionally substituted by one or more independent $G^{41}$ substituents; wherein $R^1$ is cycloC$_{3-10}$alkyl or heterocyclyl, any of which is optionally substituted by one or more independent $G^{11}$ substituents; and the other variables are described as above for Formula I.

In an embodiment of this seventh aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—); m is 0; $R^4$ is C$_{0-8}$alkyl or cycloC$_{3-10}$alkyl, any of which is optionally substituted by one or more independent $G^{41}$ substituents; wherein $R^1$ is cycloC$_{3-10}$alkyl, optionally substituted by one or more independent $G^{11}$ substituents; and the other variables are described as above for Formula I.

In an embodiment of this seventh aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—); m is 0; $R^4$ is C$_{0-8}$alkyl or cycloC$_{3-10}$alkyl, any of which is optionally substituted by one or more independent $G^{41}$ substituents; wherein $R^1$ is cyclobutyl, cyclopentyl, or cyclohexyl, any of which is optionally substituted by one or more independent $G^{11}$ substituents; and the other variables are described as above for Formula I.

In an embodiment of this seventh aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is $-(X^1)_n-(Y^1)_m-R^4$; n is 1; $X^1$ is 3-(—O—); m is 0; $R^4$ is C$_{0-8}$alkyl or cycloC$_{3-10}$alkyl, any of which is optionally substituted by one or more independent $G^{41}$ substituents; wherein $R^1$ is cycloC$_{3-10}$alkyl, optionally substituted by one or more independent $G^{11}$ substituents;

wherein $G^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, —NR$^{21}$S(O)$_{j4}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221a}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)R$^{3331}$, —NR$_{2221}$C(=O)OR$^{3331}$, —NR$^{2221}$C(=O)NR$^{3331}$R$^{2221a}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this seventh aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—); m is 0; R$^4$ is C$_{0-8}$alkyl or cycloC$_{3-10}$alkyl, any of which is optionally substituted by one or more independent G$^{41}$ substituents; wherein R$^1$ is cyclobutyl, cyclopentyl, or cyclohexyl, any of which is optionally substituted by one or more independent G$^{11}$ substituents;

wherein G$^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, —NR$^{21}$S(O)$_{j4}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221a}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an eighth aspect of the present invention, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—); m is 0; R$^4$ is C$_{0-6}$alkyl; and the other variables are described as above for Formula I.

In an embodiment of this eighth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—); m is 0; R$^4$ is C$_{0-6}$alkyl; wherein R$^1$ is aryl, heteroaryl, cycloC$_{3-10}$alkyl, or heterocyclyl, any of which is optionally substituted by one or more independent G$^{11}$ substituents; and the other variables are described as above for Formula I.

In an embodiment of this eighth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—); m is 0; R$^4$ is C$_{0-6}$alkyl; wherein R$^1$ is cycloC$_{3-10}$alkyl or heterocyclyl, any of which is optionally substituted by one or more independent G$^{11}$ substituents; and the other variables are described as above for Formula I.

In an embodiment of this eighth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—); m is 0; R$^4$ is C$^{0-6}$alkyl; wherein R$^1$ is cycloC$_{3-10}$alkyl, optionally substituted by one or more independent G$^{11}$ substituents; and the other variables are described as above for Formula I.

In an embodiment of this eighth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—); m is 0; R$^4$ is C$_{0-6}$alkyl; wherein R$^1$ is cyclobutyl, cyclopentyl, or cyclohexyl, any of which is optionally substituted by one or more independent G$^{11}$ substituents; and the other variables are described as above for Formula I.

In an embodiment of this eighth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—); m is 0; R$^4$ is C$_{0-6}$alkyl; wherein R$^1$ is cycloC$_{3-10}$alkyl, optionally substituted by one or more independent G$^{11}$ substituents;

wherein G$^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, —NR$^{21}$S(O)$_{j4}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221a}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this eighth aspect, a compound is represented by Formula I, or a pharmaceutically acceptable salt thereof, wherein Q$^1$ is phenyl substituted by said one to five independent G$^{10}$ substituents wherein at least one of said G$^{10}$ substituents is —(X$^1$)$_n$—(Y$^1$)$_m$—R$^4$; n is 1; X$^1$ is 3-(—O—); m is 0; R$^4$ is C$_{0-6}$alkyl; wherein R$^1$ is cyclobutyl, cyclopentyl, or cyclohexyl, any of which is optionally substituted by one or more independent G$^{11}$ substituents;

wherein G$^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, NR$^{21}$C(=O)NR$^{31}$R$^{21a}$, —NR$^{21}$S(O)$_{j4}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221a}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)R$^{3331}$, —NR$^{2221}$C(=O)OR$^{3331}$, R$^{2221a}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In a ninth aspect of the present invention, a compound is represented by Formula I, or a pharmaceutically acceptable salt thereof, wherein Q$^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; wherein $R^4$ is H or methyl; and the other variables are described as above for Formula I.

In an embodiment of this ninth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; wherein $R^4$ is H or methyl; wherein $R^1$ is aryl, heteroaryl, cyclo$C_{3-10}$alkyl, or heterocyclyl, any of which is optionally substituted by one or more independent $G^{11}$ substituents; and the other variables are described as above for Formula I.

In an embodiment of this ninth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; wherein $R^4$ is H or methyl; wherein $R^1$ is cyclo$C_{3-10}$alkyl or heterocyclyl, any of which is optionally substituted by one or more independent $G^{11}$ substituents; and the other variables are described as above for Formula I.

In an embodiment of this ninth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; wherein $R^4$ is H or methyl; wherein $R^1$ is cyclo$C_{3-10}$alkyl, optionally substituted by one or more independent $G^{11}$ substituents; and the other variables are described as above for Formula I.

In an embodiment of this ninth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; wherein $R^4$ is H or methyl; wherein $R^1$ is cyclobutyl, cyclopentyl, or cyclohexyl, any of which is optionally substituted by one or more independent $G^{11}$ substituents; and the other variables are described as above for Formula I.

In an embodiment of this ninth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; wherein $R^4$ is H or methyl; wherein $R^1$ is cyclo$C_{3-10}$alkyl, optionally substituted by one or more independent $G^{11}$ substituents;

wherein $G^{11}$ is —$OR^2$, —$NR^{21}R^{31}$, —$CO_2R^{21}$, —$C(O)R^{21}$, —$CONR^{21}R^{31}$, —$NR^{21}C(=O)R^{31}$, —$NR^{21}C(=O)OR^{31}$, —$NR^{21}C(=O)NR^{31}R^{21a}$, —$NR^{21}S(O)_{j4}R^{31}$, —$OC(=O)OR^{21}R^{31}$, $C_{0-10}$alkyl, cyclo$C_{3-8}$alkyl, cyclo$C_{3-8}$alkenyl, heterocyclyl-$C_{0-10}$-oalkyl, or heterocyclyl-$C_{2-10}$alkenyl, any of which is optionally substituted with one or more independent halo, oxo, —$CF_3$, —$OCF_3$, —$OR^{2221}$, —$NR^{2221}R^{3331}(R^{2221a})_{j4a}$, —$C(O)R^{2221}$, —$CO_2R^{2221}$, —$CONR^{2221}R^{3331}$, —$NO_2$, —$CN$, —$S(O)_{j4a}R^{2221}$, —$SO_2NR^{2221}R^{3331}$, —$NR^{2221}C(=O)R^{3331}$, —$NR^{2221}C(=O)OR^{3331}$, —$N^{2221}C(=O)NR^{3331}R^{2221a}$, —$NR^{2221}S(O)_{j4a}R^{3331}$, —$C(=S)OR^{2221}$, —$C(=O)SR^{2221}$, —$NR^{2221}C(=NR^{3331})R^{2221a}R^{3331a}$, —$NR^{2221}C(=NR^{3331})OR^{2221a}$, —$NR^{2221}C(=NR^{3331})SR^{2221a}$, —$OC(=O)OR^{2221}$, —$OC(=O)NR^{2221}R^{3331}$, —$OC(=O)SR^{2221}$, —$SC(=O)OR^{2221}$, or —$SC(=O)NR^{2221}R^{3331}$ substituents; and the other variables are described as above for Formula I.

In an embodiment of this ninth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; wherein $R^4$ is H or methyl; wherein $R^1$ is cyclobutyl, cyclopentyl, or cyclohexyl, any of which is optionally substituted by one or more independent $G^{11}$ substituents;

wherein $G^{11}$ is —$OR^{21}$, —$NR^{21}R^{31}$, —$CO_2R^{21}$, —$C(O)R^{21}$, —$CONR^{21}R^{31}$, —$NR^{21}C(=O)R^{31}$, —$NR^{21}C(=O)OR^{31}$, —$NR^{21}C(=O)NR^{31}R^{21a}$, —$NR^{21}S(O)_{j4}R^{31}$, —$OC(=O)OR^{21}$, —$OC(=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, —$CF_3$, —$OCF_3$, —$OR^{2221}$, —$NR^{2221}R^{3331}(R^{2221a})_{j4a}$, —$C(O)R^{2221}$, —$CO_2R^{2221}$, —$CONR^{2221}R^{3331}$, —$NO_2$, —$CN$, —$S(O)_{j4a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{2221a}$, —$NR^{2221}S(O)_{j4a}R^{3331}$, —$C(=S)OR^{2221}$, —$C(=O)SR^{2221}$, —$NR^{2221}C(=NR^{3331})NR^{2221a}R^{3331a}$, —$NR^{2221}C(=NR^{3331})OR^{2221a}$, —$NR^{2221}C(=NR^{3331})SR^{2221a}$, —$OC(=O)OR^{2221}$, —$OC(=O)NR^{2221}R^{3331}$, —$OC(=O)SR^{2221}$, —$SC(=O)OR^{2221}$, or —$SC(=O)NR^{2221}R^{3331}$ substituents; and the other variables are described as above for Formula I.

In an tenth aspect of the present invention, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is aryl optionally substituted by one or more independent $G^{41}$ substituents; and the other variables are described as above for Formula I.

In an embodiment of this tenth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is aryl optionally substituted by one or more independent $G^{41}$ substituents; wherein $R^1$ is aryl, heteroaryl, cyclo$C_{3-10}$alkyl, or heterocyclyl, any of which is optionally substituted by one or more independent $G^{11}$ substituents; and the other variables are described as above for Formula I.

In an embodiment of this tenth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is aryl optionally substituted by one or more independent $G^{41}$ substituents; wherein $R^1$ is cyclo$C_{3-10}$alkyl or heterocyclyl, any of which is optionally substituted by one or more independent $G^{11}$ substituents; and the other variables are described as above for Formula I.

In an embodiment of this tenth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is aryl optionally substituted by one or more independent $G^{41}$ substituents; wherein $R^1$ is cyclobutyl, cyclopentyl, or cyclohexyl, any of which is optionally substituted by one or more independent $G^{11}$ substituents; and the other variables are described as above for Formula I.

In an embodiment of this tenth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is aryl optionally substituted by one or more independent $G^{41}$ substituents; wherein $R^1$ is cycloC$_{3-10}$alkyl or heterocyclyl, any of which is optionally substituted by one or more independent $G^{11}$ substituents;

wherein $G^{11}$ is —$OR^{21}$, —$NR^{21}R^{31}$, —$CO_2R^{21}$, —$C(O)R^{21}$, —$CONR^{21}R^{31}$, —$NR^{21}C(=O)R^{31}$, —$NR^{21}C(=O)OR^{31}$, —$NR^{21}C(=O)NR^{31}R^{21a}$, —$NR^{21}S(O)_{j3}R^{31}$, —$OC(=O)OR^{21}$, —$OC(=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —$CF_3$, —$OCF_3$, —$OR^{2221}$, —$NR^{2221}R^{3331}(R^{2221a})_{j3a}$, —$C(O)R^{2221}$, —$CO_2R^{2221}$, —$CONR^{2221}R^{3331}$, —$NO_2$, —CN, —$S(O)_{j3a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{2221a}$, —$NR^{2221}S(O)_{j3a}R^{3331}$, —$C(=S)OR^{2221}$, —$C(=O)SR^{2221}$, —$N^{2221}C(=NR^{3331})NR^{2221a}R^{3331a}$, —$NR^{2221}C(=NR^{3331})OR^{2221a}$, —$NR^{2221}C(=NR^{3331})SR^{2221a}$, —$OC(=O)OR^{2221}$, —$OC(=O)NR^{2221}R^{3331}$, —$OC(=O)SR^{2221}$, —$SC(=O)OR^{2221}$, or —$SC(=O)NR^{2221}R^{3331}$ substituents; and the other variables are described as above for Formula I.

In an embodiment of this tenth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is aryl optionally substituted by one or more independent $G^{41}$ substituents; wherein $R^1$ is cyclobutyl, cyclopentyl, or cyclohexyl, any of which is optionally substituted by one or more independent $G^{11}$ substituents;

wherein $G^{11}$ is —$OR^{21}$, —$NR^{21}R^{31}$, —$CO_2R^{21}$, —$C(O)R^{21}$, —$CONR^{21}R^{31}$, —$NR^{21}C(=O)R^{31}$, —$NR^{21}C(=O)OR^{31}$, —$NR^{21}C(=O)NR^{31}R^{21a}$, —$NR^{21}S(O)_{j3}R^{31}$, —$OC(=O)OR^{21}$, —$OC(=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —$CF_3$, —$OCF_3$, —$OR^{222}$, —$NR^{2221}R^{3331}(R^{2221a})_{j3a}$, —$C(O)R^{2221}$, —$CO_2R^{2221}$, —$CONR^{2221}R^{3331}$, —$NO_2$, —CN, —$S(O)_{j3a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{2221a}$, —$NR^{2221}S(O)_{j3a}R^{3331}$, —$C(=S)OR^{2221}$, —$C(=O)SR^{2221}$, —$NR^{2221}C(=NR^{3331})NR^{2221a}R^{3331a}$, —$NR^{2221}C(=NR^{3331})OR^{2221a}$, —$NR^{2221}C(=NR^{3331})SR^{2221a}$, —$OC(=O)OR^{2221}$, —$OC(=O)NR^{2221}R^{3331}$, —$OC(=O)SR^{2221}$, —$SC(=O)OR^{2221}$, or —$SC(=O)NR^{2221}R^{3331}$ substituents; and the other variables are described as above for Formula I.

In an eleventh aspect of the present invention, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is phenyl optionally substituted by one or more independent $G^{41}$ substituents; and the other variables are described as above for Formula I.

In an embodiment of this eleventh aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is phenyl optionally substituted by one or more independent $G^{41}$ substituents; wherein $R^1$ is aryl, heteroaryl, cycloC$_{3-10}$alkyl, or heterocyclyl, any of which is optionally substituted by one or more independent $G^{11}$ substituents; and the other variables are described as above for Formula I.

In an embodiment of this eleventh aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is phenyl optionally substituted by one or more independent $G^{41}$ substituents; wherein $R^1$ is cycloC$_{3-10}$alkyl or heterocyclyl, any of which is optionally substituted by one or more independent $G^{11}$ substituents; and the other variables are described as above for Formula I.

In an embodiment of this eleventh aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3-(—O—); m is 0; $R^4$ is phenyl optionally substituted by one or more independent $G^{41}$ substituents; wherein $R^1$ is cyclobutyl, cyclopentyl, or cyclohexyl, any of which is optionally substituted by one or more independent $G^{11}$ substituents; and the other variables are described as above for Formula I.

In a twelfth aspect of the present invention, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3- or 4-(—NH—); m is 1; $Y^1$ is —(—$SO_2$—); $R^4$ is aryl optionally substituted by one or more independent $G^{41}$ substituents; and the other variables are described as above for Formula I.

In an embodiment of this twelfth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3- or 4-(—NH—); m is 1 $Y^1$ is —(—$SO_2$—); $R^4$ is aryl optionally substituted by one or more independent $G^{41}$ substituents; wherein $R^1$ is aryl, heteroaryl, cycloC$_{3-10}$alkyl, or heterocyclyl, any of which is optionally substituted by one or more independent $G^{11}$ substituents; and the other variables are described as above for Formula I.

In an embodiment of this twelfth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3- or 4-(—NH—); m is 1; $Y^1$ is —(—$SO_2$—); $R^4$ is aryl optionally substituted by one or more independent $G^{41}$ substituents; wherein $R^1$ is cycloC$_{3-10}$alkyl or heterocyclyl, any of which is optionally substituted by one or more independent $G^{11}$ substituents; and the other variables are described as above for Formula I.

In an embodiment of this twelfth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3- or 4-(—NH—); m is 1; $Y^1$ is —(—$SO_2$—); $R^4$ is aryl optionally substituted by one or more independent $G^{41}$ substituents; wherein $R^1$ is cyclobutyl, cyclopentyl, or cyclohexyl, any of which is optionally substituted by one or more independent $G^{11}$ substituents; and the other variables are described as above for Formula I.

In an embodiment of this twelfth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3- or 4-(—NH—); m is 1; $Y^1$ is —(—$SO_2$—); $R^4$ is aryl optionally substituted by one or more independent $G^{41}$ substituents; wherein $R^1$ is cycloC$_{3-10}$alkyl or heterocyclyl, any of which is optionally substituted by one or more independent $G^{11}$ substituents;

wherein $G^{11}$ is —$OR^{21}$, —$NR^{21}R^{31}$, —$CO_2R^{21}$, —$C(O)R^{21}$, —$CONR^{21}R^{31}$, —$NR^{21}C(=O)R^{31}$, —$NR^{21}C(=O)OR^{31}$, —$NR^{21}C(=O)NR^{31}R^{21a}$, —$NR^{21}S(O)_{j3}R^{31}$, —$OC(=O)OR^{21}$, —$OC(=O)NR^{21}R^{31}$, $C_{0-10}$alkyl, cycloC$_{3-8}$alkyl, cycloC$_{3-8}$alkenyl, heterocyclyl-$C_{0-10}$alkyl, or heterocyclyl-$C_{2-10}$alkenyl, any of which is optionally substituted with one or more independent halo, oxo, —$CF_3$, —$OCF_3$, —$OR^{2221}$, —$NR^{2221}R^{3331}(R^{2221})_{j3a}$, —$C(O)R^{2221}$, —$CO_2R^{2221}$, —$CONR^{2221}R^{3331}$, —$NO_2$, —$CN$, —$S(O)_{j3a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{2221a}$, —$NR^{2221}S(O)_{j3a}R^{3331}$, —$C(=S)OR^{2221}$, —$C(=O)SR^{2221}$, —$NR^{2221}C(=NR^{3331})NR^{2221a}R^{3331a}$, —$NR^{2221}C(=NR^{3331})OR^{2221a}$, —$NR^{2221}C(=N^{3331})SR^{2221a}$, —$OC(=O)OR^{2221}$, —$OC(=O)NR^{2221}R^{3331}$, —$OC(=O)SR^{2221}$, —$SC(=O)OR^{2221}$, or —$SC(=O)NR^{2221}R^{3331}$ substituents; and the other variables are described as above for Formula I.

In an embodiment of this twelfth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3- or 4-(—NH—); m is 1; $Y^1$ is —(—$SO_2$—); $R^4$ is aryl optionally substituted by one or more independent $G^{41}$ substituents; wherein $R^1$ is cyclobutyl, cyclopentyl, or cyclohexyl, any of which is optionally substituted by one or more independent $G^{11}$ substituents;

wherein $G^{11}$ is —$OR^{21}$, —$NR^{21}R^{31}$, —$CO_2R^{21}$, —$C(O)R^{21}$, —$CONR^{21}R^{31}$, —$NR^{21}C(=O)R^{31}$, —$NR^{21}C(=O)OR^{31}$, —$NR^{21}C(=O)NR^{31}R^{21a}$, —$NR^{21}S(O)_{j3}R^{31}$, —$OC(=O)OR^{21}$, —$OC(=O)NR^{21}R^{31}$, $C_{0-10}$alkyl, cycloC$_{3-8}$alkyl, cycloC$_{3-8}$alkenyl, heterocyclyl-$C_{0-10}$alkyl, or heterocyclyl-$C_{2-10}$alkenyl, any of which is optionally substituted with one or more independent halo, oxo, —$CF_3$, —$OCF_3$, —$OR^{2221}$, —$NR^{2221}R^{3331}(R^{2221a})_{j3a}$, —$C(O)R^{2221}$, —$CO_2R^{2221}$, —$CONR^{2221}R^{3331}$, —$NO_2$, —$CN$, —$S(O)_{j3a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{2221a}$, —$NR^{2221}S(O)_{j3a}R^{3331}$, —$C(=S)OR^{2221}$, —$C(=O)SR^{2221}$, —$NR^{2221}C(=NR^{3331})NR^{2221a}R^{3331a}$, —$NR^{2221}C(=NR^{3331})OR^{2221a}$, —$NR^{2221}C(=NR^{3331})SR^{2221a}$, —$OC(=O)OR^{2221}$, —$OC(=O)NR^{2221}R^{3331}$, —$OC(=O)SR^{2221}$, —$SC(=O)OR^{2221}$, or —$SC(=O)NR^{2221}R^{3331}$ substituents; and the other variables are described as above for Formula I.

In an embodiment of this twelfth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3- or 4-(—NH—); m is 1; $Y^1$ is —(—$SO_2$—); $R^4$ is aryl optionally substituted by one or more independent $G^{41}$ substituents; wherein $R^1$ is cis- or trans- cyclobutyl substituted at the 3-position by $G^{11}$ wherein $G^{11}$ is —OH, —$NH_2$, —$N(CH_3)_2$, —NHAc, —NH(CO)NHCH$_3$, —NH(CO)OCH$_3$, —CH$_2$OH, —CH$_2$NH$_2$, —CH$_2$NHAc, CONH$_2$, —CH$_2$N(CH$_3$)$_2$, —CH$_2$NH(CO)NHMe, —CH$_2$NH(CO)OCH$_3$, CO$_2$CH$_3$, or CONHCH$_3$,; and the other variables are described as above for Formula I.

In an embodiment of this twelfth aspect, a compound is represented by Formula I, or a pharmaceutically acceptable salt thereof, wherein $Q^1$ is phenyl substituted by said one to five independent $G^{10}$ substituents wherein at least one of said $G^{10}$ substituents is —$(X^1)_n$—$(Y^1)_m$—$R^4$; n is 1; $X^1$ is 3- or 4-(—NH—); m is 1; $Y^1$ is —(—$SO_2$—); $R^4$ is aryl optionally substituted by one or more independent $G^{41}$ substituents; wherein $R^1$ is cis- or trans- cyclohexyl substituted at the 4-position by $G^{11}$ wherein $G^{11}$ is —OH, —$NH_2$, —$N(CH_3)_2$, —NHAc, —NH(CO)NHCH$_3$, —NH(CO)OCH$_3$, —CH$_2$OH, —CH$_2$NH$_2$, —CH$_2$NHAc, CONH$_2$, —CH$_2$N(CH$_3$)$_2$, —CH$_2$NH(CO)NHMe, —CH$_2$NH(CO)OCH$_3$, CO$_2$CH$_3$, or CONHCH$_3$; and the other variables are described as above for Formula I.

In a thirteenth aspect of the present invention, a compound is represented by Formula I, or a pharmaceutically acceptable salt thereof, wherein $Q^1$ is aryl$^1$ substituted by one or more independent $G^{10}$ substituents and the other variables are described as above for Formula I.

In an embodiment of this thirteenth aspect, a compound is represented by Formula I, or a pharmaceutically acceptable salt thereof, wherein $Q^1$ is phenyl substituted by one or more independent by $G^{10}$ substituents and the other variables are described as above for Formula I.

In a fourteenth aspect of the present invention, a compound is represented by Formula I, or a pharmaceutically acceptable salt thereof, wherein $Q^1$ is aryl$^1$ substituted by one or more independent $G^{10}$ substituents, wherein the at least one $G^{10}$ substituent is —$(X^1)_n$—$(Y^1)_m$—$R^4$, and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents, wherein the at least one $G^{10}$ substituent is —$(X^1)_n$—$(Y^1)_m$—$R^4$, and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is —$(X^1)_n$—$(Y^1)_m$—$R^4$; wherein $X^1$ is 3-(O)—, 4-(O)—, 3-(NH)—, or 4-(NH)—; wherein $Y^1$ is —CH$_2$— or —(SO$_2$)—; wherein n and m are independently 0 or 1; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is —$(X^1)_n$—$(Y^1)_m$—$R^4$; wherein $X^1$ is 3-(O)— or 4-(O)—; wherein $Y^1$ is —CH$_2$—; n and m are each 1; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is —$(X^1)_n$—$(Y^1)_m$—$R^4$; wherein $X^1$ is 3-(O)— or 4-(O)—; wherein $Y^1$ is —CH$_2$—; wherein n and m are each 1; wherein $R^4$ is aryl, $C_{0-10}$alkyl, or cycloC$_{3-10}$alkyl, any of which is optionally substituted by one or more independent $G^{41}$ substituents; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is —$(X^1)_n$—$(Y^1)_m$—$R^4$; wherein $X^1$ is 3-(O)— or 4-(O)—; wherein $Y^1$ is —CH$_2$—; wherein n and m are each 1;

wherein $R^4$ is phenyl optionally substituted by one or more independent $G^{41}$ substituents; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; wherein $Y^1$ is —CH$_2$—; wherein n and m are each 1; wherein $R^4$ is aryl, C$_{0-10}$alkyl, or cycloC$_{3-10}$alkyl, any of which is optionally substituted by one or more independent $G^{41}$ substituents; wherein $R^1$ is aryl, heteroaryl, cycloC$_{3-10}$alkyl, or heterocyclyl, any of which is optionally substituted by $G^{11}$; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; $Y^1$ is —CH$_2$—; n and m are each 1; wherein $R^4$ is aryl, C$_{0-10}$alkyl, or cycloC$_{3-10}$alkyl, any of which is optionally substituted by one or more independent $G^{41}$ substituents; wherein $R^1$ is cycloC$_{3-10}$alkyl which is optionally substituted by $G^{11}$; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)—or 4-(O)—; wherein $Y^1$ is —CH$_2$—; wherein n and m are each 1; wherein $R^4$ is phenyl optionally substituted by one or more independent $G^{41}$ substituents; wherein $R^1$ is aryl, heteroaryl, cycloC$_{3-10}$alkyl, or heterocyclyl, any of which is optionally substituted by $G^{11}$; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; wherein $Y^1$ is —CH$_2$—; wherein n and m are each 1; wherein $R^4$ is phenyl optionally substituted by one or more independent $G^{41}$ substituents; wherein $R^1$ is cycloC$_{3-10}$alkyl which is optionally substituted by $G^{11}$; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; wherein $Y^1$ is —CH$_2$—; n and m are each 1; wherein $R^4$ is phenyl optionally substituted by one or more independent $G^{41}$ substituents; wherein $R^1$ is cyclobutyl, cyclopentyl, or cyclohexyl, any of which is optionally substituted by $G^{11}$; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; wherein $Y^1$ is —CH$_2$—; wherein n and m are each 1; wherein $R^4$ is phenyl optionally substituted by one or more independent $G^{41}$ substituents; wherein $R^1$ is cis- or trans-cyclobutyl substituted at the 3-position by $G^{11}$ or $R^1$ is cis- or trans-cyclohexyl substituted at the 4-position by $G^{11}$; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; wherein $Y^1$ is —CH$_2$—; n and m are each 1; wherein $R^4$ is phenyl optionally substituted by one or more independent $G^{41}$ substituents; wherein $R^1$ is cis- or trans-cyclobutyl substituted at the 3-position by $G^{11}$ wherein $G^{11}$ is —OH, —NH$_2$, —N(CH$_3$)$_2$, —NHAc, —NH(CO)NHCH$_3$, —NH(CO)OCH$_3$, —CH$_2$OH, —CH$_2$NH$_2$, —CH$_2$NHAc, CONH$_2$, —CH$_2$N(CH$_3$)$_2$, —CH$_2$NH(CO)NHMe, —CH$_2$NH(CO)OCH$_3$, CO$_2$CH$_3$, or CONHCH$_3$; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; wherein $Y^1$ is —CH$_2$—; wherein n and m are each 1; wherein $R^4$ is phenyl optionally substituted by one or more independent $G^{41}$ substituents; wherein $R^1$ is cis- or trans-cyclohexyl substituted at the 4-position by $G^{11}$ wherein $G^{11}$ is —OH, —NH$_2$, —N(CH$_3$)$_2$, —NHAc, —NH(CO)NHCH$_3$, —NH(CO)OCH$_3$, —CH$_2$OH, —CH$_2$NH$_2$, —CH$_2$NHAc, CONH$_2$, —CH$_2$N(CH$_3$)$_2$, —CH$_2$NH(CO)NHMe, —CH$_2$NH(CO)OCH$_3$, CO$_2$CH$_3$, or CONHCH$_3$; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; wherein $Y^1$ is —CH$_2$—; wherein n and m are each 1; wherein $R^4$ is aryl, C$_{0-10}$alkyl, or cycloC$_{3-10}$alkyl, any of which is optionally substituted by one or more independent $G^{41}$ substituents; wherein $R^1$ is cycloC$_{3-10}$alkyl which is optionally substituted by $G^{11}$;

wherein $G^{11}$ is —OR$^{21}$, —NR$^{21}$R$^{31}$, —CO$_2$R$^{21}$, —C(O)R$^{21}$, —CONR$^{21}$R$^{31}$, —NR$^{21}$C(=O)R$^{31}$, —NR$^{21}$C(=O)OR$^{31}$, —NR$^{21}$C(=O)NR$^{31}$R$^{21a}$, —NR$^{21}$S(O)$_{j3}$R$^{31}$, —OC(=O)OR$^{21}$, —OC(=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{2221a}$)$_{j3a}$, —C(O)R$^{2221}$, —CO$_2$R$^{2221}$, —CONR$^{2221}$R$^{3331}$, —NO$_2$, —CN, —S(O)$_{j3a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{2221a}$, —NR$^{2221}$S(O)$_{j3a}$R$^{3331}$, —C(=S)OR$^{2221}$, —C(=O)SR$^{2221}$, —NR$^{2221}$C(=NR$^{3331}$)NR$^{2221a}$R$^{3331a}$, —NR$^{2221}$C(=NR$^{3331}$)OR$^{2221a}$, —NR$^{2221}$C(=NR$^{3331}$)SR$^{2221a}$, —OC(=O)OR$^{2221}$, —OC(=O)NR$^{2221}$R$^{3331}$, —OC(=O)SR$^{2221}$, —SC(=O)OR$^{2221}$, or —SC(=O)NR$^{2221}$R$^{3331}$ substituents; and the other variables are described as above for Formula I.

In an embodiment of this fourteenth aspect, a compound is represented by Formula I, or a pharmaceutically acceptable salt thereof, wherein $Q^1$ is phenyl substituted by one or more independent $G^{10}$ substituents wherein at least one $G^{10}$ substituent is $—(X^1)_n—(Y^1)_m—R^4$; wherein $X^1$ is 3-(O)— or 4-(O)—; wherein $Y^1$ is —CH$_2$—; wherein n and m are each 1; wherein $R^4$ is phenyl optionally substituted by one or more independent G⁴¹ substituents; wherein R¹ is aryl, heteroaryl, cycloC$_{3-10}$alkyl, or heterocyclyl, any of which is optionally substituted by G¹¹;

wherein G¹¹ is —OR², —NR²¹R³¹, —CO$_2$R²¹, —C(O)R²¹, —CONR²¹R³¹, —NR²¹C(=O)R³¹, —NR²¹C(=O)OR³¹, —NR²¹C(=O)NR³¹R²¹ᵃ, —NR²¹S(O)$_{j3}$R³¹, —OC(=O)OR²¹, —OC(=O)NR²¹R³¹, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR²²²¹, —NR²²²¹R³³³¹(R²²²ᵃ)$_{j3a}$, —C(O)R²²²¹, —CO$_2$R²²²¹, —CONR²²²¹R³³³¹, —NO$_2$, —CN, —S(O)$_{j3a}$R²²²¹, —SO$_2$NR²²²¹R³³³¹, —NR²²²¹C(=O)R³³³¹, —NR²²²¹C(=O)OR³³³¹, —NR²²²¹C(=O)NR³³³¹R²²²¹ᵃ, —NR²²²¹S(O)$_{j3a}$R³³³¹, —C(=S)OR²²²¹, —C(=O)SR²²²¹, —NR²²²¹C(=NR³³³¹)NR²²²¹ᵃR³³³¹ᵃ, —NR²²²¹C(=NR³³³¹)OR²²²¹ᵃ, —NR²²²¹C(=NR³³³¹)SR²²²¹ᵃ, —OC(=O)OR²²²¹, —OC(=O)NR²²²¹R³³³¹, —OC(=O)SR²²²¹, —SC(=O)OR²²²¹, or —SC(=O)NR²²²¹R³³³¹ substituents; and the other variables are described as above for Formula I.

In an embodiment of this fourteenth aspect, a compound is represented by Formula I, or a pharmaceutically acceptable salt thereof, wherein Q¹ is phenyl substituted by one or more independent G¹⁰ substituents wherein at least one G¹⁰ substituent is —(X¹)$_n$—(Y¹)$_m$—R⁴; wherein R¹ is represented by the structural formula:

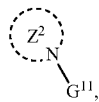

wherein Z² is a heterocyclyl containing a N substituted by G¹¹; and the other variables are described as above for Formula I.

In an embodiment of this fourteenth aspect, a compound is represented by Formula I, or a pharmaceutically acceptable salt thereof, wherein Q¹ is phenyl substituted by one or more independent G¹⁰ substituents wherein at least one G¹⁰ substituent is —(X¹)$_n$—(Y¹)$_m$—R⁴; wherein R¹ is represented by the structural formula:

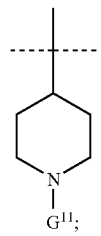

wherein G¹¹ is —C(O)R²¹, —CO$_2$R²¹, —ONR²¹R³¹, —SO$_2$NR²¹R³¹, —S(O)$_{j3}$R³¹, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR²²²¹, —NR²²²¹R³³³¹, —(O)R²²²¹, —CO$_2$R²²²¹, —CONR²²²¹R³³³¹, —SO$_2$NR²²²¹R³³³¹, —NR²²²¹C(=O)R³³³¹, —NR²²²¹C(=O)OR³³³¹, —NR²²²¹C(=O)NR³³³¹R²²²¹ᵃ, —NR²²²¹S(O)$_{j3a}$R³³³¹, —NR²²²¹C(=NR³³³¹)NR²²²¹ᵃR³³³¹ᵃ, or —OC(=O)NR²²²¹R³³³¹ substituents;

or G¹¹ is aryl-C$_{0-10}$alkyl or hetaryl-C$_{0-10}$alkyl, any of which is optionally substituted with one or more independent halo, —CF$_3$, —OCF$_3$, —OR²²²¹, —NR²²²¹R³³³¹, —C(O)R²²²¹, —CO$_2$R²²²¹, —CONR²²²¹R³³³¹, —SO$_2$NR²²²¹R³³³¹, —NR²²²¹C(=O)R³³³¹, —NR²²²¹C(=O)OR³³³¹, —NR²²²¹C(=O)NR³³³¹R²²²¹ᵃ, —NR²²²¹S(O)$_{j3a}$R³³³¹, —NR²²²¹C(=NR³³³¹)NR²²²¹ᵃR³³³¹ᵃ, or —OC(=O)NR²²²¹R³³³¹ substituents; and the other variables are described as above for Formula I.

In an embodiment of this fourteenth aspect, a compound is represented by Formula I, or a pharmaceutically acceptable salt thereof, wherein Q¹ is phenyl substituted by one or more independent G¹⁰ substituents wherein at least one G¹⁰ substituent is —(X¹)$_n$—(Y¹)$_m$—R⁴;

wherein R¹ is represented by the structural formula:

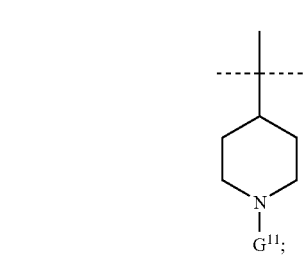

wherein G¹¹ is —C(O)R²¹, —CO$_2$R²¹, —CONR²¹R³¹, —SO$_2$NR²¹R³¹, —S(O)$_{j3}$R³¹, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR²²²¹, —NR²²²¹R³³³¹, —C(O)R²²²¹, —CO$_2$R²²²¹, —CONR²²²¹R³³³¹, —SO$_2$NR²²²¹R³³³¹, —NR²²²¹C(=O)R³³³¹, —NR²²²¹C(=O)OR³³³¹, —NR²²²¹C(=O)NR³³³¹R²²²¹ᵃ, —NR²²²¹S(O)$_{j3a}$R³³³¹, —NR²²²¹C(=NR³³³¹)NR²²²¹ᵃR³³³¹ᵃ, or —OC(=O)NR²²²¹R³³³¹ substituents; and the other variables are described as above for Formula I.

In an embodiment of this fourteenth aspect, a compound is represented by Formula I, or a pharmaceutically acceptable salt thereof, wherein Q¹ is phenyl substituted by one or more independent G¹⁰ substituents wherein at least one G¹⁰ substituent is —(X¹)$_n$—(Y¹)$_m$—R⁴;

wherein R¹ is represented by the structural formula:

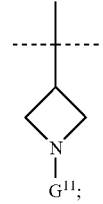

wherein G¹¹ is —C(O)R²¹, —CO$_2$R²¹, —CONR²¹R³¹, —SO$_2$NR²¹R³¹, —S(O)$_{j3}$R³¹, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{2221}$, —NR$^{2221}$R$^{3331}$, —C(O)R$^{2221}$, —CO$_2$R$^{2221}$, —CONR$^{2221}$R$^{3331}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{2221}$R$^{3331}$, —NR$^{2221}$S(O)$_{j3a}$R$^{3331}$, —NR$^{2221}$C(=NR$^{3331}$)NR$^{2221a}$R$^{3331a}$, or —OC(=O)NR$^{2221}$R$^{3331}$ substituents;

or G$^{11}$ aryl-C$_{0-10}$alkyl or hetaryl-C$_{0-10}$alkyl, any of which is optionally substituted with one or more independent halo, —CF$_3$, —OCF$_3$, —OR$^{2221}$, —NR$^{2221}$R$^{3331}$, —C(O)R$^{2221}$, —CO$_2$R$^{2221}$, —CONR$^{2221}$R$^{3331}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{2221}$R$^{3331}$, —NR$^{2221}$S(O)$_{j3a}$R$^{3331}$, —NR$^{2221}$C(=NR$^{3331}$)NR$^{2221a}$R$^{3331a}$, or —OC(=O)NR$^{2221}$R$^{3331}$ substituents; and the other variables are described as above for Formula I.

In an embodiment of this fourteenth aspect, a compound is represented by Formula I, or a pharmaceutically acceptable salt thereof, wherein Q$^1$ is phenyl substituted by one or more independent G$^{10}$ substituents; wherein at least one G$^{10}$ substituent is —(X$^1$)$_n$—(Y$^1$)$_m$—R$^4$;

wherein R$^1$ is represented by the structural formula:

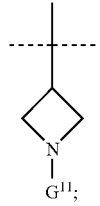

wherein G$^{11}$ is —C(O)R$^{21}$, —CO$_2$R$^{21}$, —CONR$^{21}$R$^{31}$, —SO$_2$NR$^{21}$R$^{31}$, —S(O)$_{j3}$R$^{31}$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent oxo, —CF$_3$, —OCF$_3$, —OR$^{2221}$, —NR$^{2221}$R$^{3331}$, —C(O)R$^{2221}$, —CO$_2$R$^{2221}$, —CONR$^{2221}$R$^{3331}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{2221}$R$^{3331}$, —NR$^{2221}$S(O)$_{j3a}$R$^{3331}$, —NR$^{2221}$C(=NR$^{3331}$)NR$^{2221a}$R$^{3331a}$, or —OC(=O)NR$^{2221}$R$^{3331}$ substituents; and the other variable are described as above for Formula I.

The present invention includes the following compounds:
5-(3-benzyloxy-2-fluoro-phenyl)-7-cyclobutyl-imidazo[5,1-f][1,2,4]triazin-4-ylamine,
5-(3-Benzyloxy-phenyl)-7-cyclobutyl-imidazo[5,1-f][1,2,4]triazin-4-ylamine
3-[4-Amino-5-(3-benzyloxy-phenyl)-imidazo[5,1-f][1,2,4]triazin-7-yl]-cyclobutanone,
3-[4-Amino-5-(3-benzyloxy-phenyl)-imidazo[5,1-f][1,2,4]triazin-7-yl]-cyclobutanol,
3-[4-Amino-5-(3-benzyloxy-phenyl)-imidazo[5,1-f][1,2,4]triazin-7-yl-]1-methyl-cyclobutanol,
3-[4-Amino-5-(3-benzyloxy-phenyl)-imidazo[5,1-f][1,2,4]triazin-7-yl]-1-ethyl-cyclobutanol,
5-(3-Benzyloxy-phenyl)-7-(3-methylamino-cyclobutyl)-imidazo[5,1-f][1,2,4]triazin-4-ylamine,
5-(3-Benzyloxy-phenyl)-7-(3-dimethylamino-cyclobutyl)-imidazo[5,1-f][1,2,4]triazin-4-ylamine,
7-(3-Azetidin-1-yl-cyclobutyl)-5-(3-benzyloxy-phenyl)-imidazo[5,1-f][1,2,4]triazin-4-ylamine,
5-(3-Benzyloxy-phenyl)-7-(3-piperidin-1-yl-cyclobutyl)-imidazo[5,1-f][1,2,4]triazin-4-ylamine,
N-{3-[4-Amino-5-(3-benzyloxy-phenyl)-imidazo[5,1-f][1,2,4]triazin-7-yl]-cyclobutyl}-acetamide,
{3-[4-Amino-5-(3-benzyloxy-phenyl)-imidazo[5,1-f][1,2,4]triazin-7-yl]-cyclobutyl}-carbamic acid methyl ester,
1-{3-[4-Amino-5-(3-benzyloxy-phenyl)-imidazo[5,1-f][1,2,4]triazin-7-yl]-cyclobutyl}-3methyl-urea,
N-{3-[4-Amino-5-(3-benzyloxy-phenyl)-imidazo[5,1-f][1,2,4]triazin-7-yl]-cyclobutyl}-methanesulfonamide,
7-Azetidin-3-yl-5-(3-benzyloxy-phenyl)-imidazo[5,1-f][1,2,4]triazin-4-ylamine,
1-{3-[4-Amino-5-(3-benzyloxy-phenyl)-imidazo[5,1-f][1,2,4]triazin-7-yl]-azetidin-1-yl}-ethanone,
{3-[4-Amino-5-(3-benzyloxy-phenyl)-imidazo[5,1-f][1,2,4]triazin-7-yl]-cyclobutyl}-methanol,
5-(3-Benzyloxy-phenyl)-7-(3-dimethylaminomethyl-cyclobutyl)-imidazo[5,1-f][1,2,4]triazin-4-ylamine,
5-(3-Benzyloxy-phenyl)-7-(3-diethylaminomethyl-cyclobutyl)-imidazo[5,1-f][1,2,4]triazin-4-ylamine,
7-(3-Azetidin-1-ylmethyl-cyclobutyl)-5-(3-benzyloxy-phenyl)-imidazo[5,1-f][1,2,4]triazin-4-ylamine,
5-(3-Benzyloxy-phenyl)-7-(3-piperidin-1-ylmethyl-cyclobutyl)-imidazo[5,1-f][1,2,4]triazin-4-ylamine,
3-[4-Amino-5-(3-benzyloxy-phenyl)-imidazo[5,1-f][1,2,4]triazin-7-yl]-cyclobutanecarboxylic acid amide,
5-(3-Benzyloxy-phenyl)-7-cyclohexyl-imidazo[5,1-f][1,2,4]triazin-4-ylamine,
4-[4-Amino-5-(3-benzyloxy-phenyl)-imidazo[5,1-f][1,2,4]triazin-7-yl]-cyclohexanone,
4-[4-Amino-5-(3-benzyloxy-phenyl)-imidazo[5,1-f][1,2,4]triazin-7-yl]-cyclohexanol,
4-[4-Amino-5-(3-benzyloxy-phenyl)-imidazo[5,1-f][1,2,4]triazin-7-yl]-1-methyl-cyclohexanol,
4-[4-Amino-5-(3-benzyloxy-phenyl)-imidazo[5,1-f][1,2,4]triazin-7-yl]-1-ethyl-cyclohexanol,
4-[4-Amino-5-(3-benzyloxy-phenyl)-imidazo[5,1-f][1,2,4]triazin-7-yl]-cyclohexanecarboxylic acid methyl ester,
4-[4-Amino-5-(3-benzyloxy-phenyl)-imidazo[5,1-f][1,2,4]triazin-7-yl]-cyclohexanecarboxylic acid amide,
4-[4-Amino-5-(3-benzyloxy-phenyl)-imidazo[5,1-f][1,2,4]triazin-7-yl]-cyclohexanecarboxylic acid methylamide,
{4-[4-Amino-5-(3 -benzyloxy-phenyl)-imidazo[5,1-f][1,2,4]triazin-7-yl]-cyclohexyl}-methanol,
7-(4-Aminomethyl-cyclohexyl)-5-(3-benzyloxy-phenyl)-imidazo[5,1-f][1,2,4]triazin-4-ylamine,
5-(3-Benzyloxy-phenyl)-7-(4-dimethylaminomethyl-cyclohexyl)-imidazo[5,1-f][1,2,4]triazin-4-ylamine,
7-(4-Azetidin-1-ylmethyl-cyclohexyl)-5-(3-benzyloxy-phenyl)-imidazo[5,1-f][1,2,4]triazin-4-ylamine,
5-(3-Benzyloxy-phenyl)-7-(4-pyrrolidin-1-ylmethyl-cyclohexyl)-imidazo[5,1-f][1,2,4]triazin-4-ylamine,
5-(3-Benzyloxy-phenyl)-7-(4-piperidin-1-ylmethyl-cyclohexyl)-imidazo[5,1-f][1,2,4]triazin-4-ylamine,
5-(3-Benzyloxy-phenyl)-7-piperidin-4-yl-imidazo[5,1-f][1,2,4]triazin-4-ylamine,
1-{4-[4-Amino-5-(3-benzyloxy-phenyl)-imidazo[5,1-f][1,2,4]triazin-7-yl]-piperidin-1-yl}-ethanone,
5-(3-Benzyloxy-phenyl)-7-cyclopentyl-imidazo[5,1-f][1,2,4]triazin-4-ylamine,
3-[4-Amino-5-(3-benzyloxy-phenyl)-imidazo[5,1-f][1,2,4]triazin-7-yl]-cyclopentanecarboxylic acid methyl ester,
3-[4-Amino-5-(3-benzyloxy-phenyl)-imidazo[5,1-f][1,2,4]triazin-7-yl]-cyclopentanecarboxylic acid amide,
3-[4-Amino-5-(3-benzyloxy-phenyl)-imidazo[5,1-f][1,2,4]triazin-7-yl]-cyclopentanecarboxylic acid methylamide,
{3-[4-Amino-5-(3-benzyloxy-phenyl)-imidazo[5,1-f][1,2,4]triazin-7-yl]-cyclopentyl}-methanol, 7-(3-Aminomethyl-cyclopentyl)-5-(3-benzyloxy-phenyl)-imidazo[5,1-f][1,2,4]triazin-4-ylamine,
5-(3-Benzyloxy-phenyl)-7-(3-ethylaminomethyl-cyclopentyl)-imidazo[5,1-f][1,2,4]triazin-4-ylamine,
7-(3-Azetidin-1-ylmethyl-cyclopentyl)-5-(3-benzyloxy-phenyl)-imidazo[5,1-f][1,2,4]triazin-4-ylamine,
5-(3-Benzyloxy-phenyl)-7-(3-pyrrolidin-1-ylmethyl-cyclopentyl)-imidazo[5,1-f][1,2,4]triazin-4-ylamine,
5-(3-Benzyloxy-phenyl)-7-(3-piperidin-1-ylmethyl-cyclopentyl)-imidazo[5,1-f][1,2,4]triazin-4-ylamine,
N-{3-[4-Amino-5-(3-benzyloxy-phenyl)-imidazo[5,1-f][1,2,4]triazin-7-yl]-cyclopentylmethyl}-acetamide,
{3-[4-Amino-5-(3-benzyloxy-phenyl)-imidazo[5,1-f][1,2,4]triazin-7-yl]-cyclopentylmethyl}-carbamic acid methyl ester,
1-{3-[4-Amino-5-(3-benzyloxy-phenyl)-imidazo[5,1-f][1,2,4]triazin-7-yl]-cyclopentylmethyl}-3-methyl-urea,
3-[4-Amino-5-(3-benzyloxy-phenyl)-imidazo[5,1-f][1,2,4]triazin-7-yl]-cyclopentanone,
3-[4-Amino-5-(3-benzyloxy-phenyl)-imidazo[5,1-f][1,2,4]triazin-7-yl]-cyclopentanol,
7-(3-Amino-cyclopentyl)-5-(3-benzyloxy-phenyl)-imidazo[5,1-f][1,2,4]triazin-4-ylamine,
5-(3-Benzyloxy-phenyl)-7-(3-dimethylamino-cyclopentyl)-imidazo[5,1-f][1,2,4]triazin-4-ylamine,
7-(3-Azetidin-1-yl-cyclopentyl)-5-(3-benzyloxy-phenyl)-imidazo[5,1-f][1,2,4]triazin-4-ylamine,
5-(3-Benzyloxy-phenyl)-7-(3-pyrrolidin-1-yl-cyclopentyl)-imidazo[5,1-f][1,2,4]triazin-4-ylamine,
5-(3-Benzyloxy-phenyl)-7-(3-piperidin-1-yl-cyclopentyl)-imidazo[5,1-f][1,2,4]triazin-4-ylamine,
5-(3-Benzyloxy-phenyl)-7-phenyl-imidazo[5,1-f][1,2,4]triazin-4-ylamine,
4-[4-Amino-5-(3-benzyloxy-phenyl)-imidazo[5,1-f][1,2,4]triazin-7-yl]-benzoic acid methyl ester,
4-[4-Amino-5-(3-benzyloxy-phenyl)-imidazo[5,1-f][1,2,4]triazin-7-yl]-benzamide,
4-[4-Amino-5-(3-benzyloxy-phenyl)-imidazo[5,1-f][1,2,4]triazin-7-yl]-N-methyl-benzamide,
{4-[4-Amino-5-(3-benzyloxy-phenyl)-imidazo[5,1-f][1,2,4]triazin-7-yl-]phenyl}-methanol,
7-(4-Aminomethyl-phenyl)-5-(3-benzyloxy-phenyl)-imidazo[5,1-f][1,2,4]triazin-4-ylamine,
5-(3-Benzyloxy-phenyl)-7-(4-dimethylaminomethyl-phenyl)-imidazo[5,1-f][1,2,4]triazin-4-ylamine,
N-{4-[4-Amino-5-(3-benzyloxy-phenyl)-imidazo[5,1-f][1,2,4]triazin-7-yl]-benzyl}-acetamide,
{4-[4-Amino-5-(3-benzyloxy-phenyl)-imidazo[5,1-f][1,2,4]triazin-7-yl]-benzyl}-carbamic acid methyl ester,
1-{4-[4-Amino-5-(3-benzyloxy-phenyl)-imidazo[5,1-f][1,2,4]triazin-7-yl]-benzyl}-3-methyl-urea,
5-(3-Benzyloxy-phenyl)-7-(4-dimethylaminomethyl-phenyl)-imidazo[5,1-f][1,2,4]triazin-4-ylamine,
7-(4-Azetidin-1-ylmethyl-phenyl)-5-(3-benzyloxy-phenyl)-imidazo[5,1-f][1,2,4]triazin-4-ylamine,
5-(3-Benzyloxy-phenyl)-7-(4-pyrrolidin-1-ylmethyl-phenyl)-imidazo[5,1-f][1,2,4]triazin-4-ylamine,
5-(3-Benzyloxy-phenyl)-7-(4-piperidin-1-ylmethyl-phenyl)-imidazo[5,1-f][1,2,4]triazin-4-ylamine,
3-[4-Amino-5-(3-benzyloxy-phenyl)-imidazo[5,1-f][1,2,4]triazin-7-yl]-benzoic acid methyl ester,
3-[4-Amino-5-(3-benzyloxy-phenyl)-imidazo[5,1-f][1,2,4]triazin-7-yl]-benzamide,
3-[4-Amino-5-(3-benzyloxy-phenyl)-imidazo[5,1-f][1,2,4]triazin-7-yl]-N-methyl-benzamide,
{3-[4-Amino-5-(3-benzyloxy-phenyl)-imidazo[5,1-f][1,2,4]triazin-7-yl]-phenyl}-methanol,
7-(3-Aminomethyl-phenyl)-5-(3-benzyloxy-phenyl)-imidazo[5,1-f][1,2,4]triazin-4-ylamine,
N-{3-[4-Amino-5-(3-benzyloxy-phenyl)-imidazo[5,1-f][1,2,4]triazin-7-yl]-benzyl}-acetamide,
{3-[4-Amino-5-(3-benzyloxy-phenyl)-imidazo[5,1-f][1,2,4]triazin-7-yl]-benzyl}-carbamic acid methyl ester,
1-{3-[4-Amino-5-(3-benzyloxy-phenyl)-imidazo[5,1-f][1,2,4]triazin-7yl]-benzyl}-3-methyl-urea,
N-{3-[4-Amino-5-(3-benzyloxy-phenyl)-imidazo[5,1-f][1,2,4]triazin-7-yl]-benzyl}-methanesulfonamide,
5-(3-Benzyloxy-phenyl)-7-(3-dimethylaminomethyl-phenyl)-imidazo[5,1-f][1,2,4]triazin-4-ylamine,
5-(3-Benzyloxy-phenyl)-7-(3-diethylaminomethyl-phenyl)-imidazo[5,1-f][1,2,4]triazin-4-ylamine,
7-(3-Azetidin-1-ylmethyl-phenyl)-5-(3-benzyloxy-phenyl)-imidazo[5,1-f][1,2,4triazin-4-ylamine,
5-(3-Benzyloxy-phenyl)-7-(3-pyrrolidin-1-ylmethyl-phenyl)-imidazo[5,1-f][1,2,4triazin-4-ylamine,
5-(3-Benzyloxy-phenyl)-7-(3-piperidin-1-ylmethyl-phenyl)-imidazo[5,1-f][1,2,4triazin-4-ylamine,
5-(3-Benzyloxy-phenyl)-7-pyridin-4-yl-imidazo[5,1-f][1,2,4]triazin-4-ylamine,
5-(3-Benzyloxy-phenyl)-7-oxazol-2-yl-imidazo[5,1-f][1,2,4]triazin-4-ylamine,
5-(3-Benzyloxy-phenyl)-7-thiophen-3-yl-imidazo[5,1-f][1,2,4]triazin-4-ylamine,
5-(3-Benzyloxy-phenyl)-7-thiophen-2-yl-imidazo[5,1-f][1,2,4]triazin-4-ylamine,
5-(3-Benzyloxy-phenyl)-7-thiazol-5-yl-imidazo[5,1-f][1,2,4]triazin-4-ylamine,
5-(3-Benzyloxy-phenyl)-7-thiazol-2-yl-imidazo[5,1-f][1,2,4]triazin-4-ylamine,
5-(3-Benzyloxy-phenyl)-7-(1H-imidazol-2-yl)-imidazo[5,1-f][1,2,4]triazin-4-ylamine,
5-(3-Benzyloxy-phenyl)-7-(1H-imidazol-4-yl)-imidazo[5,1-f][1,2,4]triazin-4-ylamine, or a pharmaceutically acceptable salt thereof.

The present invention includes a method of inhibiting protein kinase activity comprising administering a compound of Formula I or a pharmaceutically acceptable salt thereof.

The present invention includes the method of inhibiting protein kinase activity comprising administering a compound of Formula I or a pharmaceutically acceptable salt thereof wherein said protein kinase is IGF-1R.

The present invention includes the method of inhibiting protein kinase activity comprising administering a compound of Formula I or a pharmaceutically acceptable salt thereof wherein the activity of said protein kinase affects hyperproliferative disorders.

The present invention includes the method of inhibiting protein kinase activity comprising administering a compound of Formula I or a pharmaceutically acceptable salt thereof wherein the activity of said protein kinase influences angiogenesis, vascular permeability, immune response, cellular apoptosis, tumor growth, or inflammation.

The present invention includes a method of treating a patient having a condition which is mediated by protein kinase activity, said method comprising administering to the patient a therapeutically effective amount of a compound of Formula I or a pharmaceutically acceptable salt thereof.

The present invention includes a method of treating a patient having a condition which is mediated by protein kinase activity, said method comprising administering to the patient a therapeutically effective amount of a compound of Formula I or a pharmaceutically acceptable salt thereof wherein said protein kinase is IGF-1R.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is a hyperproliferative disorder.

The present invention includes a method of treating a patient having a condition which is mediated by protein kinase activity, said method comprising administering to the patient a therapeutically effective amount of a compound of Formula I or a pharmaceutically acceptable salt thereof wherein the activity of said protein kinase influences angiogenesis, vascular permeability, immune response, cellular apoptosis, tumor growth, or inflammation.

The present invention includes a method of treating a patient having a condition which is mediated by protein kinase activity, said method comprising administering to the patient a therapeutically effective amount of a compound of Formula I or a pharmaceutically acceptable salt thereof wherein the protein kinase is a protein serine/threonine kinase or a protein tyrosine kinase.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is one or more ulcers.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is one or more ulcers wherein the ulcer or ulcers are caused by a bacterial or fungal infection; or the ulcer or ulcers are Mooren ulcers; or the ulcer or ulcers are a symptom of ulcerative colitis.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is Lyme disease, sepsis or infection by Herpes simplex, Herpes Zoster, human immunodeficiency virus, parapoxvirus, protozoa, or toxoplasmosis.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is von Hippel Lindau disease, pemphigoid, psoriasis, Paget's disease, or polycystic kidney disease.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is fibrosis, sarcoidosis, cirrhosis, thyroiditis, hyperviscosity syndrome, Osler-Weber-Rendu disease, chronic occlusive pulmonary disease, asthma, exudtaes, ascites, pleural effusions, pulmonary edema, cerebral edema or edema following burns, trauma, radiation, stroke, hypoxia, or ischemia.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is ovarian hyperstimulation syndrome, preeclainpsia, menometrorrhagia, or endometriosis.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase-activity is chronic inflammation, systemic lupus, glomerulonephritis, synovitis, inflammatory bowel disease, Crohn's disease, glomerulonephritis, rheumatoid arthritis and osteoarthritis, multiple sclerosis, or graft rejection.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is sickle cell anemia.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is an ocular condition.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is an ocular condition wherein the ocular condition is ocular or macular edema, ocular neovascular disease, seleritis, radial keratotomy, uveitis, vitritis, myopia, optic pits, chronic retinal detachment, post-laser treatment complications, conjunctivitis, Stargardt's disease, Eales disease, retinopathy, or macular degeneration.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is a cardiovascular condition.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is atherosclerosis, restenosis, ischemia/reperfusion injury, vascular occlusion, venous malformation, or carotid obstructive disease.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is cancer.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is cancer wherein the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, or malignant ascites.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is cancer wherein the cancer is Kaposi's sarcoma, Hodgkin's disease, lymphoma, myeloma, or leukemia.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is Crow-Fukase (POEMS) syndrome or a diabetic condition.

The present invention includes a method of treating a patient having a condition which is mediated by protein kinase activity, said method comprising administering to the patient a therapeutically effective amount of a compound of Formula I or a pharmaceutically acceptable salt thereof wherein the condition mediated by protein kinase activity is Crow-Fukase (POEMS) syndrome or a diabetic condition wherein the diabetic condition is insulin-dependent diabetes mellitus glaucoma, diabetic retinopathy, or microangiopathy.

The present invention includes a method of treating a patient having a condition which is mediated by protein kinase activity, said method comprising administering to the patient a therapeutically effective amount of a compound of Formula I or a pharmaceutically acceptable salt thereof wherein the protein kinase activity is involved in T cell activation, B cell activation, mast cell degranulation, monocyte activation, signal transduction, apoptosis, the potentiation of an inflammatory response or a combination thereof.

The present invention includes the use of a compound of Formula I, or a pharmaceutically acceptable salt thereof, for the preparation of a pharmaceutical composition for the treatment of a disease which responds to an inhibition of the IGF-1R-dependent cell proliferation.

The present invention includes the use of a compound of Formula I, or a pharmaceutically acceptable salt thereof, for the preparation of a pharmaceutical composition for the treatment of a disease which responds to an inhibition of the IGF-1R tyrosine kinase.

The present invention includes the a method of inhibiting protein kinase activity comprising administering a pharmaceutical composition comprising a therapeutically effective amount of a compound of Formula I, or a pharmaceutically acceptable salt thereof, and a pharmaceutically acceptable carrier.

The present invention includes a method of treating a patient having a condition which is mediated by protein kinase activity, said method comprising administering to the patient a therapeutically effective amount of a pharmaceutical composition comprising a therapeutically effective amount of a compound of Formula I, or a pharmaceutically acceptable salt thereof, and a pharmaceutically acceptable carrier.

Unless otherwise stated, the connections of compound name moieties are at the rightmost recited moiety. That is, the substituent name starts with a terminal moiety, continues with any bridging moieties, and ends with the connecting moiety. For example, hetarylthio$C_{1-4}$alkyl has a heteroaryl group connected through a thio sulfur to a $C_{1-4}$ alkyl that connects to the chemical species bearing the substituent.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl and the like.

The term "acyl" refers to an alkylketo or arylketo group, for example, formyl, acetyl, butyryl, benzoyl, and the like.

The term "halo" refers to fluoro, chloro, bromo, or iodo.

The term "haloalkyl" refers to an alkyl group substituted with one or more halo groups, for example, chloromethyl, 2-bromoethyl, 3-iodopropyl, trifluoromethyl, perfluoropropyl, 8-chlorononyl, and the like.

The term "cycloalkyl" refers to a cyclic aliphatic ring structure, optionally substituted with alkyl, hydroxy and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "alkylcarbonyloxyalkyl" refers to an ester moiety, for example, acetoxymethyl, n-butyryloxyethyl, and the like.

The term "alkynylcarbonyl" refers to an alkynylketo functionality, for example, propynoyl and the like.

The term "hydroxyalkyl" refers to an alkyl group substituted with one or more hydroxy groups, for example, hydroxymethyl, 2,3-dihydroxybutyl, and the like.

The term "alkylsulfonylalkyl" refers to an alkyl group substituted with an alkylsulfonyl moiety, for example, mesylmethyl, isopropylsulfonylethyl, and the like.

The term "alkylsulfonyl" refers to a sulfonyl moiety substituted with an alkyl group, for example, mesyl, n-propylsulfonyl, and the like.

The term "monoalkylaminoalkyl" refers to an alkyl group substituted with an amine moiety which is itself substituted with one alkyl group, for example, N-methylaminoethyl and the like.

The term "dialkylaminoalkyl" refers to an alkyl group substituted with an amine moiety which is itself substituted with two alkyl groups, for example, N,N-dimethylaminoethyl, N-ethyl-N-methylaminomethyl, and the like.

The term "monoarylaminoalkyl" refers to an alkyl group substituted with an amine moiety which is itself substituted with one aryl group, for example, N-phenylaminoethyl and the like.

The term "diarylaminoalkyl" refers to an alkyl group substituted with an amine moiety which is itself substituted with two aryl groups, for example, N,N-diphenylaminoethyl and the like.

The term "monohetarylaminoalkyl" or "monoheteroarylaminoalkyl" refers to an alkyl group substituted with an amine moiety which is itself substituted with one hetaryl group.

The term "dihetarylaminoalkyl" or "diheteroarylaminoalkyl" refers to an alkyl group substituted with an amine moiety which is itself substituted with two hetaryl groups.

The term "monoalkylaminocarbonyl" refers to an amide group substituted with one alkyl group, for example, N-methylamido and the like.

The term "dialkylaminocarbonyl" refers to an amide group substituted with two alkyl groups, for example, N,N-dimethylamido, N-methyl-N-ethylamido and the like.

The term "monoarylaminocarbonyl" refers to an amide group substituted with one aryl group, for example, N-phenylamido and the like.

The term "diarylaminocarbonyl" refers to an amide group substituted with two aryl groups, for example, N,N-diphenylamido and the like.

The term "alkylarylaminocarbonyl" refers to an amide group substituted with one alkyl and one aryl group, for example, N-methyl-N-phenylamido and the like.

The term "monohetarylaminocarbonyl" or "monoheteroarylaminocarbonyl" refers to an amide group substituted with one hetaryl group.

The term "dihetarylaminocarbonyl" or "diheteroarylaminocarbonyl" refers to an amide group substituted with two hetaryl groups.

The term "alkylhetarylaminocarbonyl" or "alkylheteroarylaminocarbonyl" refers to an amide group substituted with one alkyl and one hetaryl group.

The term "acetylaminoalkyl" refers to an alkyl group substituted with an amide moiety, for example, acetylaminomethyl and the like.

The term "acetylaminoalkenyl" refers to an alkenyl group substituted with an amide moiety, for example, 2-(acetylamino)vinyl and the like.

The term "alkenyl" refers to an ethylenically unsaturated hydrocarbon group, straight or branched chain, having at least one ethylenic bond, for example, vinyl, allyl, 1-butenyl, 2-butenyl, isopropenyl, 2-pentenyl, and the like.

The term "haloalkenyl" refers to an alkenyl group substituted with one or more halo groups.

The term "cycloalkenyl" refers to a cyclic aliphatic ring structure having at least one endocyclic ethylenic bond, optionally substituted with one or more independent substituents such as alkyl, hydroxy, or halo. Examples of cycloalkenyls include, but are not limited to, methylcyclopropenyl, trifluoromethylcyclopropenyl, cyclopentenyl, cyclohexenyl, 1,4-cyclohexadienyl, and the like.

The term "alkynyl" refers to an unsaturated hydrocarbon group, straight or branched, having at least one acetylenic bond, for example, ethynyl, propargyl, and the like.

The term "haloalkynyl" refers to an alkynyl group substituted with one or more halo groups.

The term "alkylcarbonyl" refers to an alkylketo functionality, for example, acetyl, n-butyryl, and the like.

The term "alkenylcarbonyl" refers to an alkenylketo functionality, for example, propenoyl and the like.

The term "aryl" refers to phenyl or naphthyl which may be optionally substituted by one or more independent substituents. Typical aryl substituents include, but are not limited to, phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

The term "aryl$^1$" refers to phenyl which may be optionally substituted by one or more independent substituents. Typical aryl$^1$ substituents include, but are not limited to, phenyl, 4-chlorophenyl, 4-fluorophenyl, 4-bromophenyl, 2-methoxyphenyl, 2-methylphenyl, 4-methylphenyl, 4-ethylphenyl, 2,4-dibromophenyl, 2,4,6-trichlorophenyl, 4-methoxyphenyl, 2,4-dimethoxyphenyl, 4-(trifluoromethyl)phenyl, and 2-iodo-4-methylphenyl.

The terms "heteroaryl" or "hetaryl" refer to a substituted or unsubstituted 5- or 6-membered unsaturated ring containing one, two, three, or four heteroatoms, preferably one or two heteroatoms independently selected from oxygen, nitrogen, and sulfur or to a substituted or unsubstituted bicyclic unsaturated ring system containing up to 10 atoms including at least one heteroatom selected from oxygen, nitrogen, and sulfur. Examples of hetaryls include, but are not limited to, 2-, 3-, or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl.

The terms "heteroaryl$^1$" or "hetaryl$^1$" refer to a substituted or unsubstituted 5- or 6-membered unsaturated ring containing one, two, three, or four heteroatoms, preferably one or two heteroatoms independently selected from oxygen, nitrogen and sulfur. Examples of hetaryl's include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, and thiadiazolyl. The heterocyclic ring may be optionally substituted with up to two substituents.

The terms "aryl-alkyl" or "arylalkyl" or "aralkyl" are used to describe a group wherein the alkyl chain can be branched or straight chain with the aryl portion, as defined hereinbefore, forming a bridging portion of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl, and 10-phenyldecyl.

The terms "aryl-Cycloalkyl" or "arylcycloalkyl" are used to describe a group wherein the aryl group is attached to a cycloalkyl group, for example, phenylcyclopentyl and the like.

The terms "aryl-alkenyl" or "arylalkenyl" are used to describe a group wherein the alkenyl chain can be branched or straight chain with the aryl portion, as defined hereinbefore, forming a bridging portion of the aralkenyl moiety, for example, styryl (2-phenylvinyl), phenpropenyl, and the like.

The terms "aryl-alkynyl" or "arylalkynyl" are used to describe a group wherein the alkynyl chain can be branched or straight chain with the aryl portion, as defined hereinbefore, forming a bridging portion of the aryl-alkynyl moiety, for example, 3-phenyl-1-propynyl and the like.

The terms "aryl-oxy" or "aryloxy" are used to describe a terminal aryl group attached to a bridging oxygen atom. Typical aryl-oxy groups include phenoxy, 3,4-dichlorophenoxy, and the like.

The terms "aryl-oxyalkyl" or "aryloxyalkyl" are used to describe a group wherein an alkyl group is substituted with an aryl-oxy group, for example, pentafluorophenoxymethyl and the like.

The terms "hetaryl-oxy" or "heteroaryl-oxy" or "hetaryloxy" or "heteroaryloxy" are used to describe a terminal hetaryl group attached to a bridging oxygen atom. Typical hetaryl-oxy groups include 4,6-dimethoxypyrimidin-2-yloxy and the like.

The terms "hetarylalkyl" or "heteroarylalkyl" or "heteroaralkyl" or "hetaryl-alkyl" or "heteroaryl-alkyl" are used to describe a group wherein the alkyl chain can be branched or straight chain with the heteroaryl portion, as defined hereinbefore, forming a bridging portion of the heteroaralkyl moiety, for example, 3-furylmethyl, thenyl, furfuryl, and the like.

The terms "hetarylalkenyl" or "heteroarylalkenyl" or "hetaryl-alkenyl" or "heteroaryl-alkenyl" are used to describe a group wherein the alkenyl chain can be branched or straight chain with the heteroaryl portion, as defined hereinbefore, forming a bridging portion of the heteroaralkenyl moiety, for example, 3-(4-pyridyl)-1-propenyl.

The terms "hetarylalkynyl" or "heteroarylalkynyl" or "hetaryl-alkynyl" or "heteroaryl-alkynyl" are used to describe a group wherein the alkynyl chain can be branched or straight chain with the heteroaryl portion, as defined hereinbefore, forming a bridging portion of the heteroaralkynyl moiety, for example, 4-(2-thienyl)-1-butynyl.

The term "heterocyclyl" refers to a substituted or unsubstituted 3-10 membered saturated ring containing one, two, or three heteroatoms, preferably one or two heteroatoms independently selected from oxygen, nitrogen, and sulfur or to a substituted or unsubstituted bicyclic ring system containing up to 10 atoms including at least one heteroatom selected from oxygen, nitrogen, and sulfur wherein the ring containing the heteroatom is saturated. The heterocyclyl may be optionally substituted by one or more independent substituents. Examples of heterocyclyls include, but are not limited to, oxetane, azetidine, aziridene, tetrahydrofuranyl, tetrahydrofuryl, azetidinyl, pyrrolidinyl, piperidinyl, pyranyl, tetrahydropyranyl, thiolanyl, morpholinyl, piperazinyl, dioxolanyl, dioxanyl, indolinyl, 5-methyl-6-chromanyl, and

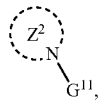

wherein $Z^2$ is a heterocyclyl containing a N substituted by $G^{11}$.

The terms "heterocyclylalkyl" or "heterocyclyl-alkyl" are used to describe a group wherein the alkyl chain can be branched or straight chain with the heterocyclyl portion, as defined hereinabove, forming a bridging portion of the heterocyclylalkyl moiety, for example, 3-piperidinylmethyl and the like.

The terms "heterocyclylalkenyl" or "heterocyclyl-alkenyl" or "heterocycloalkenyl" or "heterocyclo-alkenyl" are used to describe a group wherein the alkenyl chain can be branched or straight chain with the heterocyclyl portion, as defined hereinbefore, forming a bridging portion of the heterocyclylalkenyl moiety, for example, 2-morpholinyl-1-propenyl.

The terms "heterocyclylalkynyl" or "heterocyclyl-alkynyl" are used to describe a group wherein the alkynyl chain can be branched or straight chain with the heterocyclyl portion, as defined hereinbefore, forming a bridging portion of the heterocyclylalkynyl moiety, for example, 2-pyrrolidinyl-1-butynyl.

The term "carboxylalkyl" includes both branched and straight chain alkyl groups as defined hereinbefore attached to a carboxyl (—COOH) group.

The term "carboxylalkenyl" includes both branched and straight chain alkenyl groups as defined hereinbefore attached to a carboxyl (—COOH) group.

The term "carboxylalkynyl" includes both branched and straight chain alkynyl groups as defined hereinbefore attached to a carboxyl (—COOH) group.

The term "carboxylcycloalkyl" refers to a carboxyl (—COOH) group attached to a cyclic aliphatic ring structure as defined hereinbefore.

The term "carboxylcycloalkenyl" refers to a carboxyl (—COOH) group attached to a cyclic aliphatic ring structure having 1 or 2 ethylenic bonds as defined hereinbefore.

The terms "cycloalkylalkyl" or "cycloalkyl-alkyl" refer to a cycloalkyl group as defined hereinbefore attached to an alkyl group, for example, cyclopropylmethyl, cyclohexylethyl, and the like.

The terms "cycloalkylalkenyl" or "cycloalkyl-alkenyl" refer to a cycloalkyl group as defined hereinbefore attached to an alkenyl group, for example, cyclohexylvinyl, cycloheptylallyl, and the like.

The terms "cycloalkylalkynyl" or "cycloalkyl-alkynyl" refer to a cycloalkyl group as defined hereinbefore attached to an alkynyl group, for example, cyclopropylpropargyl, 4-cyclopentyl-2-butynyl, and the like.

The terms "cycloalkenylalkyl" or "cycloalkenyl-alkyl" refer to a cycloalkenyl group as defined hereinbefore attached to an alkyl group, for example, 2-(cyclopenten-1-yl)ethyl and the like.

The terms "cycloalkenylalkenyl" or "cycloalkenyl-alkenyl" refer to a cycloalkenyl group as defined hereinbefore attached to an alkenyl group, for example, 1-(cyclohexen-3-yl)allyl and the like.

The terms "cycloalkenylalkynyl" or "cycloalkenyl-alkynyl" refer to a cycloalkenyl group as defined hereinbefore attached to an alkynyl group, for example, 1-(cyclohexen-3-yl)propargyl and the like.

The term "carboxylcycloalkylalkyl" refers to a carboxyl (—COOH) group attached to the cycloalkyl ring portion of a cycloalkylalkyl group as defined hereinbefore.

The term "carboxylcycloalkylalkenyl" refers to a carboxyl (—COOH) group attached to the cycloalkyl ring portion of a cycloalkylalkenyl group as defined hereinbefore.

The term "carboxylcycloalkylalkynyl" refers to a carboxyl (—COOH) group attached to the cycloalkyl ring portion of a cycloalkylalkynyl group as defined hereinbefore.

The term "carboxylcycloalkenylalkyl" refers to a carboxyl (—COOH) group attached to the cycloalkenyl ring portion of a cycloalkenylalkyl group as defined hereinbefore.

The term "carboxylcycloalkenylalkenyl" refers to a carboxyl (—COOH) group attached to the cycloalkenyl ring portion of a cycloalkenylalkenyl group as defined hereinbefore.

The term "carboxylcycloalkenylalkynyl" refers to a carboxyl (—COOH) group attached to the cycloalkenyl ring portion of a cycloalkenylalkynyl group as defined hereinbefore.

The term "bicycloalkyl" refers to a cyclic aliphatic group having two rings, wherein said rings share one or two carbon atoms, which may be optionally substituted by one or more independent substituents. Examples of bicycloalkyls include, but are not limited to, spiropentane, norbornyl, bicyclo[3.1.0] hexyl, spiro[4.4]nonyl, and the like.

The term "heterobicycloalkyl" refers to a cyclic aliphatic group having two rings, wherein said rings share one or two atoms, and wherein at least one of the rings contains at least one heteroatom and which may be optionally substituted by one or more independent substituents. Examples of heterobicycloalkyls include, but are not limited to, 3-aza-bicyclo[4.1.0]heptanyl, 1,4-dioxaspiro[4.4]nonyl, and the like.

The term "alkoxy" includes both branched and straight chain terminal alkyl groups attached to a bridging oxygen atom. Typical alkoxy groups include methoxy, ethoxy, n-propoxy, isopropoxy, tert-butoxy, and the like.

The term "haloalkoxy" refers to an alkoxy group substituted with one or more halo groups, for example, chloromethoxy, trifluoromethoxy, difluoromethoxy, perfluoroisobutoxy, and the like.

The term "alkoxyalkoxyalkyl" refers to an alkyl group substituted with an alkoxy moiety which is in turn substituted with a second alkoxy moiety, for example, methoxymethoxymethyl, isopropoxymethoxyethyl, and the like.

The term "alkylthio" includes both branched and straight chain alkyl groups attached to a bridging sulfur atom, for example, methylthio and the like.

The term "haloalkylthio" refers to an alkylthio group substituted with one or more halo groups, for example, trifluoromethylthio and the like.

The term "alkoxyalkyl" refers to an alkyl group substituted with an alkoxy group, for example, isopropoxymethyl.

The term "alkoxyalkenyl" refers to an alkenyl group substituted with an alkoxy group, for example, 3-methoxyallyl.

The term "alkoxyalkynyl" refers to an alkynyl group substituted with an alkoxy group, for example, 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined hereinbefore substituted with an alkoxycarbonyl, for example, 4-(ethoxycarbonyl)-2-butenyl and the like.

The term "alkoxycarbonylalkynyl" refers to a straight chain or branched alkynyl as defined hereinbefore substituted with an alkoxycarbonyl, for example, 4-(ethoxycarbonyl)-2-butynyl and the like.

The term "haloalkoxyalkyl" refers to a straight chain or branched alkyl as defined hereinbefore substituted with a haloalkoxy, for example, 2-chloroethoxymethyl, trifluoromethoxymethyl, and the like.

The term "haloalkoxyalkenyl" refers to a straight chain or branched alkenyl as defined hereinbefore substituted with a haloalkoxy, for example, 4-(chloromethoxy)-2-butenyl and the like.

The term "haloalkoxyalkynyl" refers to a straight chain or branched alkynyl as defined hereinbefore substituted with a haloalkoxy, for example, 4-(2-fluoroethoxy)-2-butynyl and the like.

The term "alkylthioalkyl" or "alkylthio-alkyl" refers to a straight chain or branched alkyl as defined hereinbefore substituted with an alkylthio group, for example, methylthiomethyl, 3-(isobutylthio)heptyl, and the like.

The term "alkylthioalkenyl" refers to a straight chain or branched alkenyl as defined hereinbefore substituted with an alkylthio group, for example, 4-(methylthio)-2-butenyl and the like.

The term "alkylthioalkynyl" refers to a straight chain or branched alkynyl as defined hereinbefore substituted with an alkylthio group, for example, 4-(ethylthio)-2-butynyl and the like.

The term "haloalkylthioalkyl" refers to a straight chain or branched alkyl as defined hereinbefore substituted with an haloalkylthio group, for example, 2-chloroethylthiomethyl, trifluoromethylthiomethyl, and the like.

The term "haloalkylthioalkenyl" refers to a straight chain or branched alkenyl as defined hereinbefore substituted with an haloalkylthio group, for example, 4-(chloromethylthio)-2-butenyl and the like.

The term "haloalkylthioalkynyl" refers to a straight chain or branched alkynyl as defined hereinbefore substituted with a haloalkylthio group, for example, 4-(2-fluoroethylthio)-2-butynyl and the like.

The term "dialkoxyphosphorylalkyl" refers to two straight chain or branched alkoxy groups as defined hereinbefore attached to a pentavalent phosphorous atom, containing an oxo substituent, which is in turn attached to an alkyl, for example, diethoxyphosphorylmethyl.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably the composition is comprised of a pharmaceutically acceptable carrier and a non-toxic therapeutically effective amount of a compound of Formula I as described above (or a pharmaceutically acceptable salt thereof).

Moreover, within this preferred embodiment, the invention encompasses a pharmaceutical composition for the treatment of disease by inhibiting kinases, comprising a pharmaceutically acceptable carrier and a non-toxic therapeutically effective amount of compound of Formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or a pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I.

The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, allergy/asthma, disease and conditions of the immune system, disease and conditions of the central nervous system (CNS), cardiovascular disease, dermatology, and angiogenesis may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompassses a pharmaceutical composition that is comprised of a compound of Formula I in combination with a pharmaceutically acceptable carrier.

Preferably the composition is comprised of a pharmaceutically acceptable carrier and a non-toxic therapeutically effective amount of a compound of Formula I as described above, or a pharmaceutically acceptable salt thereof Moreover, within this preferred embodiment, the invention encompasses a pharmaceutical composition for the treatment of disease by inhibiting tyrosine kinase enzymes, resulting in cell proliferation, growth, differentiation, metabolism, cell cycle events, apoptosis, motility, transcription, phosphorylation, translation and other signaling processes, comprising a pharmaceutically acceptable carrier and a non-toxic therapeutically effective amount of compound of formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise a compound represented by formula I, or a pharmaceutically acceptable salt thereof, as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. E.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, allergy/asthma, disease and conditions of the immune system, disease and conditions of the central nervous system (CNS), cardiovascular disease, dermatology, and angiogenesis may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Biological Assays

The efficacy of the Examples of the invention, compounds of Formula I, as inhibitors of insulin-like growth factor-I receptor (IGF-1R) were demonstrated and confirmed by a number of pharmacological in vitro assays. The following assays and their respective methods have been carried out with the compounds according to the invention. Activity possessed by compounds of Formula I may be demonstrated in vivo.

In vitro Tyrosine Kinase Assay

The IGF-1R inhibitory of a compound of formula I can be shown in a tyrosine kinase assay using purified GST fusion protein containing the cytoplasmic kinase domain of human IGF-1R expressed in Sf9 cells. This assay is carried out in a final volume of 90 µL containing 1-100 nM (depending on the specific activity) in an Immulon-4 96-well plate (Thermo Labsystems) pre-coated with 1 µg/well of substrate poly-glutyr (4:1 ratio) in kinase buffer (50 mM Hepes, pH 7.4, 125 mM NaCl, 24 mM $MgCl_2$, 1 mM $MnCl_2$, 1% glycerol, 200 µM $Na_3VO_4$, and 2 mM DTT). The enzymatic reaction was initiated by addition of ATP at a final concentration of 100 µM. After incubation at room temperature for 30 minutes, the plates were washed with 2 mM Imidazole buffered saline with 0.02% Tween-20. Then the plate was incubated with anti-phosphotyrosine mouse monoclonal antibody pY-20 conjugated with horse radish peroxidase (HRP) (Calbiochem) at 167 ng/mL diluted in phosphate buffered saline (PBS) containing 3% bovine serum albumin (BSA), 0.5% Tween-20 and 200 µM $Na_3VO_4$ for 2 hours at room temperature. Following 3×250 µL was the bound anti-phosphotyrosine antibody was detected by incubation with 100 µl/well ABTS (Kirkegaard & Perry Labs, Inc.) for 30 minutes at room temperature. The reaction was stopped by the addition of 100 µl/well 1% SDS, and the phosphotyrosine dependent signal was measured by a plate reader at 405/490 nm.

All Examples showed inhibition of IGF-1R. The following Examples showed efficacy and activity by inhibiting IGF-1R in the biochemical assay with $IC_{50}$ values less than 15 µM. Preferably the $IC_{50}$ value is less than 5 µM. More advantageously, the $IC_{50}$ value is less than 1 µM. Even more advantageously, the $IC_{50}$ value is less than 200 nM.

The most preferred Examples are selective towards IGF-1R.

Cell-Based Autophosphotyrosine Assay

NIH 3T3 cells stably expressing full-length human IGF-1R were seeded at $1 \times 10^4$ cells/well in 0.1 ml Dulbecco's minimal essential medium (DMEM) supplemented with 10% fetal calf serum (FCS) per well in 96-well plates. On Day 2, the medium is replaced with starvation medium (DMEM containing 0.5% FCS) for 2 hours and a compound was diluted in 100% dimethyl sulfoxide (DMSO), added to the cells at six final concentrations in duplicates (20, 6.6, 2.2, 0.74, 0.25 and 0.082 µM, and incubated at 37° C. for additional 2 hours. Following addition of recombinant human IGF-1 (100 ng/mL) at 37° C. for 15 minutes, the media was then removed and the cells were washed once with PBS (phosphate-buffered saline), then lysed with cold TGH buffer (1% Triton-100, 10% glycerol, 50 mM Hepes [pH 7.4]) supplemented with 150 mM NaCl, 1.5 mM MgCl, 1 mM EDTA and fresh protease and phosphatase inhibitors [10 µg/ml leupeptin, 25 µg/ml aprotinin, 1 mM phenyl methyl sulphonyl fluoride (PMSF), and 200 µM $Na_3VO_4$]. Cell lysates were transferred to a 96-well microlite2 plate (Corning CoStar #3922) coated with 10 ng/well of IGF-1R antibody (Calbiochem, Cat#GR31L) and incubated at 4° C. overnight. Following washing with TGH buffer, the plate was incubated with anti-phosphotyrosine mouse monoclonal antibody pY-20 conjugated with horse radish peroxidase (HRP) for 2 hours at room temperature. The autophosphotyrosine was then detected by addition of Super Signal ELISA Femto Maximum Sensitivity Substrate (Pierce) and chemiluminescence was read on a Wallac Victor$^2$ 1420 Multilabel Counter. The $IC_{50}$ curves of the compounds were plotted using an ExcelFit program.

All Examples showed inhibition of IGF-1R in the cell-based assay. The following Examples showed efficacy and activity by inhibiting IGF-1R with $IC_{50}$ values less than 15 µM, with selectivity over insulin receptor expected to be in a range from 1-15 fold. Preferably the $IC_{50}$ value is less than 5 µM. More advantageously, the $IC_{50}$ value is less than 1 µM. Even more advantageously, the $IC_{50}$ value is less than 200 nM. Insulin receptor autophosphotyrosine assays are performed essentially as described above for IGF-1R cell-based assays, but use insulin (10 nM) as activating ligand and an insulin receptor antibody as capture antibody with HepG2 cells expressing endogenous human insulin receptor.

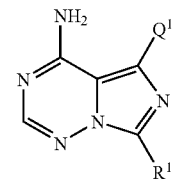

I

Experimental

Schemes 1-13 describe the synthesis of the compounds of this invention. Abbreviations used in this experimental description are: Me for methyl, Et for ethyl, $^i$Pr or $^i$Pr for isopropyl, Ph for phenyl, Bn for benzyl, EtOH for ethanol, MeOH for methanol, i-PrOH for isopropanol, THF for tetrahydrofuran, $CH_3CN$ for acetonitrile, EtOAc for ethyl acetate, NaOEt for sodium ethoxide, DMAP for 4-(dimethylamino)pyridine, DCC for 1,3-dicyclohexylcarbodiimide, EDC for 1-(3-dimethylaminopropyl)-3-ethylcarbodiimide hydrochloride, HOBt for 1-hydroxybenzotriazole, HOAt for 1-hydroxy-7-azabenzotriazole, $POCl_3$ for phosphorous oxychloride, $Pd(PPh_3)_4$ (0) for tetrakis(triphenylphosphine)palladium (0), DIEA for N,N'-diisopropylethylamine, HCl for hydrochloric acid, $H_2SO_4$ for sulfuric acid, $NaNO_2$ for sodium nitrite, $Na_2SO_4$ for sodium sulfate, Ts for tosyl, Ms for mesyl, TMS for trimethylsilyl, rt for room temperature, min for minute, h for hour, and MDP for mass directed purification.

Accordingly, the following are compounds which are useful as intermediates in the formation of IGF-1R inhibiting examples.

The compounds of Formula I of this invention and the intermediates used in the synthesis of the compounds of this invention were prepared according to the following methods.

Method A:

Scheme 1

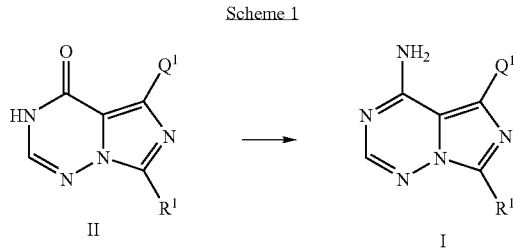

where $Q^1$ and $R^1$ are as defined previously for compound of Formula I.

In a typical preparation of compounds of Formula I, compound of Formula II was reacted with phosphorous oxychloride ($POCl_3$), triazole, and pyridine followed by ammonia in a suitable solvent. Suitable solvents for use in the above process included, but were not limited to, ethers such as tetrahydrofuran (THF), glyme, and the like; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about 0° C. and about 50° C. Preferably, the reaction was carried out at between 0° C. and about 22° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula II of Scheme I were prepared as shown below in Scheme 2.

Scheme 2

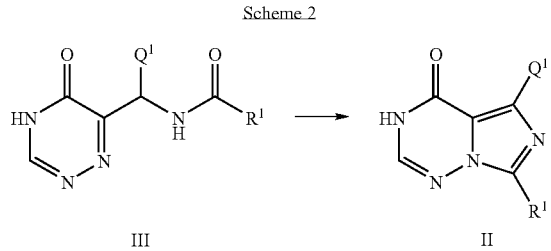

where $Q^1$ and $R^1$ are as defined previously for compound of Formula I.

In a typical preparation of a compound of Formula II, an intermediate of Formula III was treated with phosphorous oxychloride ($POCl_3$) in a suitable solvent at a suitable reaction temperature. Suitable solvents for use in the above process included, but were not limited to, ethers such as tetrahydrofuran (THF), glyme, and the like; and chlorinated solvents such as methylene chloride ($CH_2Cl_2$) or chloroform ($CHCl_3$) and acetonitrile ($CH_3CN$). If desired, mixtures of these solvents were used. The preferred solvent was methylene chloride. The above process was carried out at temperatures between about −78° C. and about 120° C. Preferably, the reaction was carried out between 40° C. and about 70° C. process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III of Scheme 2 were prepared as shown below in Scheme 3:

Scheme 3

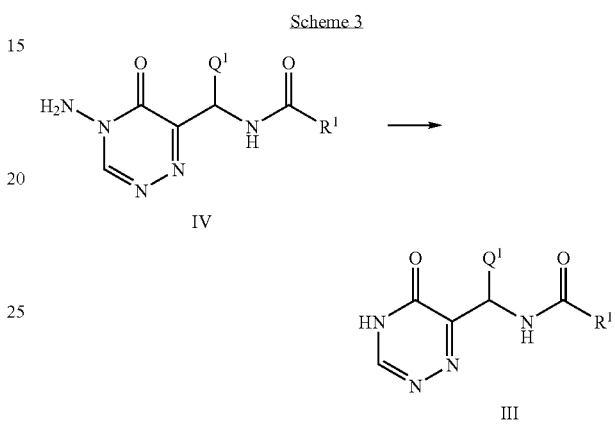

where $Q^1$ and $R^1$ are as defined previously for compound of Formula I.

In a typical preparation, of a compound of Formula III, a compound of Formula IV was treated with sodium nitrite ($NaNO_2$), a suitable acid in a suitable solvent, and suitable reaction temperatures. Suitable acids for use in the above process included, but were not limited to, HCl and $H_2SO_4$. The preferred acid was HCl. Suitable solvents for use in the above process included, but were not limited to, dimethylformamide (DMF); alcohols such as methanol, ethanol, isopropanol, trifluoroethanol, and the like; and $H_2O$. If desired, mixtures of these solvents were used, however, the preferred solvent was EtOH. The above process was carried out at temperatures between about −20° C. and about 50° C. Preferably, the reaction was carried out between 0° C. and 22° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula IV of Scheme 3 were prepared as shown below in Scheme 4:

Scheme 4

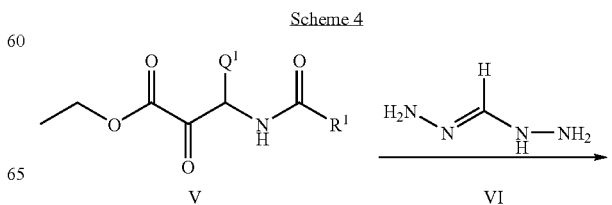

-continued

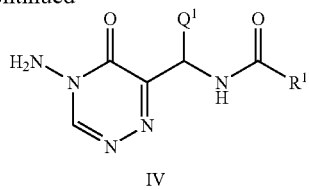

IV where $Q^1$ and $R^1$ are as defined previously for compound of Formula I.

In a typical preparation, of a compound of Formula IV, a compound of Formula V was reacted with amidrazone VI in a suitable solvent under suitable reaction temperatures. Suitable solvents for use in the above process included, but were not limited to, ethers such as tetrahydrofuran (THF), glyme, and the like; alcoholic solvents such as methanol, ethanol isopropanol, trifluoroethanol and the like. If desired, mixtures of these solvents may be used, however the preferred solvent was ethanol. The above process was carried out at temperatures between about −78° C. and about 80° C. Preferably, the reaction was carried out between −20° C. and 22° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula V of Scheme 4 were prepared as shown below in Scheme 5:

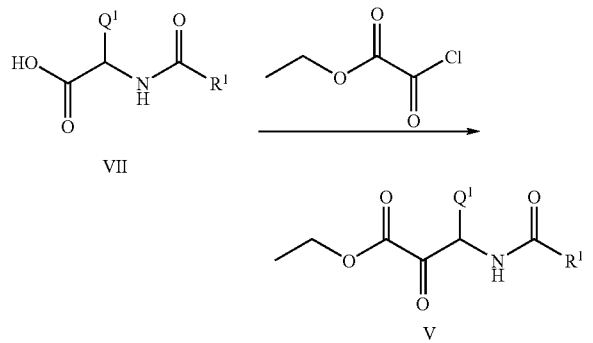

where $Q^1$ and $R^1$ are as defined previously for compound of Formula I.

In a typical preparation of a compound of Formula V, a compound of Formula VII was reacted ethyl oxalyl chloride, pyridine, and catalytic DMAP using suitable solvents under suitable reaction temperatures. Suitable solvents for use in the above process included, but were not limited to, ethers such as tetrahydrofuran (THF), glyme, and the like; acetonitrile ($CH_3CN$); chlorinated solvents such as methylene chloride ($CH_2Cl_2$) or chloroform ($CHCl_3$). If desired, mixtures of these solvents were used, however, the preferred solvent was THF. The above process may be carried out at temperatures between about 0° C. and about 100° C. Preferably, the reaction was carried out at 70° C. The above process to produce compounds of the present invention was preferably carried out at about atmospheric pressure although higher or lower pressures were used if desired. Substantially, equimolar amounts of reactants were preferably used although higher or lower amounts were used if desired. One skilled in the art would recognize that N-acylated amino acids, compounds of Formula VII, are generally commercially available or can be generally synthesized via treatment of the amino acid precursor with a suitable acylating agent (other suitable reaction conditions for the acylation of an amine can be found in (Larock, R. C. *Comprehensive Organic Transformations*, 2$^{nd}$ ed.; Wiley and Sons: New York, 1999, pp 1941-1949). One skilled in the art would also recognize that the amino acid precursors are generally commercially available or can be prepared according to conventional methods such as the known Strecker synthesis for amino acids (March. *Advanced Organic Chemistry: Reactions, Mechanisms, and Structure*, 4$^{th}$ ed.; Wiley and Sons: New York, 1992, pp 965). One skilled in the art would recognize that either racemic or enantiomerically enriched amino acids and/or derivatives of Formula VII may be used.

The compounds of Formula III of Scheme 2 may be prepared as shown below in Scheme 6:

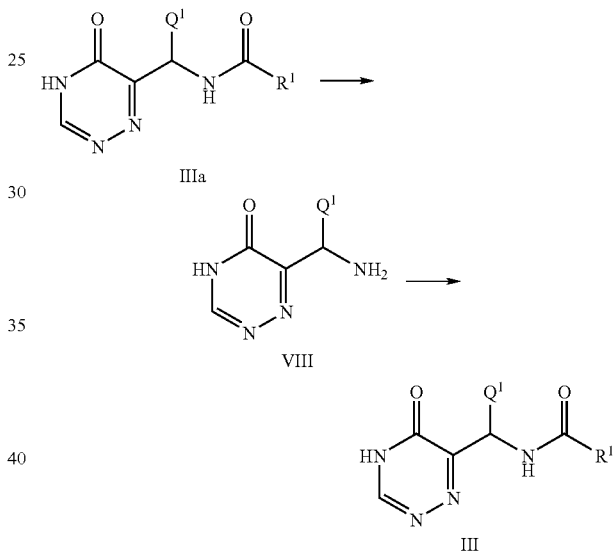

where $Q^1$ and $R^1$ are as defined previously for compound of Formula I and $A^1$-C=O is defined as an acyl group which is removable under suitable reaction conditions.

In a typical preparation, of a compound of Formula III, a compound of Formula III, can be treated under suitable conditions to afford the removal of $A^1$-C=O in a suitable solvent at a suitable temperature to afford compound of Formula VIII. Suitable conditions for use in the above process include, but are not limited to, treatment of compounds of Formula IIIa under hydrolytic conditions such as HCl in water or basic conditions such NaOH and the like in water. Suitable solvents for use in the above process include, but were not limited to, dimethylformamide (DMF); alcohols such as methanol, ethanol, isopropanol, trifluoroethanol, and the like; ethers such as tetrahydrofuran (THF), glyme, and the like; acetonitrile ($CH_3CN$); and $H_2O$. If desired, mixtures of these solvents were used. The above process can be carried out at temperatures between about −20° C. and about 100° C. Preferably, the reaction can be carried out between 22° C. and 80° C. The above process to produce compounds of the present invention can be preferably carried out at about atmospheric pressure although higher or lower pressures can be used if desired.

Substantially, equimolar amounts of reactants can be preferably used although higher or lower amounts can be used if desired. In a typical preparation, of a compound of Formula III, a compound of Formula VIII and a suitable acylating agent ($R^1CO_2H$ or $R^1COCl$) can be reacted under suitable amide coupling conditions. Suitable conditions include but are not limited to treating compounds of Formula VIII and $R^1CO_2H$ with coupling reagents such as DCC or EDC in conjunction with DMAP, HOBt, HOAt and the like or treating compounds of Formula VIII and $R^1COCl$ with base such as DIEA and the like. In either case suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used. The above process can be carried out at temperatures between about 0° C. and about 80° C. The above process to produce compounds of the present invention can be preferably carried out at about atmospheric pressure although higher or lower pressures can be used if desired. Substantially, equimolar amounts of reactants can be preferably used although higher or lower amounts can be used if desired. Additionally, other suitable reaction conditions for the conversion of $RNH_2$ to $R^1CONHR$ can be found in Larock, R. C. *Comprehensive Organic Transformations*, 2$^{nd}$ ed.; Wiley and Sons: New York, 1999, pp 1941-1949.

Method B was also used when preparing compounds of Formula I as shown below in Scheme 7:

Method B:

Scheme 7

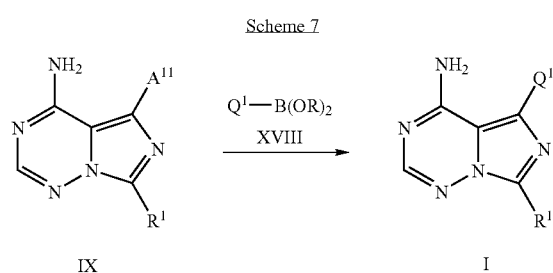

IX          I where $Q^1$ and $R^1$ are as defined previously for compound of Formula I; $A^{11}$=halogen such as Cl, Br, or I; and $B(OR)_2$=suitable boronic acid/ester wherein each R is independently $C_{0-6}$alkyl or each R is independently $C_{1-6}$alkyl taken together with the respective oxygen atom to which they are attached to form a 5-15 membered saturated or partially unsaturated ring wherein said ring is optionally substituted with 1-4 independent $C_{0-10}$alkyl substituents.

In a typical preparation of compounds of Formula I, compound of Formula IX was reacted with a suitable boronic acid/ester ($Q^1$-$B(OR)_2$) of Formula XVIII in a suitable solvent via typical Suzuki coupling procedures. A compound of Formula XVIII can be commercially available or made by literature procedures from a suitable reagent such as an aryl halide and a diborane see 2-fluoro-3-benzyloxyphenylboronic acid pinacol ester as an example. Suitable solvents for use in the above process included, but were not limited to, water, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was glyme/water. The above process was carried out at temperatures between about −78° C. and about 120° C. Preferably, the reaction was carried out between 80° C and about 100° C. The above process to produce compounds of the present invention was preferably carried out at about atmospheric pressure although higher or lower pressures were used if desired. Substantially, equimolar amounts of reactants were preferably used although higher or lower amounts were used if desired. One skilled in the art will appreciate that alternative methods may be applicable for preparing compounds of Formula I from IX. For example, compound of Formula IX could be reacted with a suitable organotin reagent $Q^1$-$SnBu_3$ or the like in a suitable solvent via typical Stille coupling procedures.

The compounds of Formula IX of Scheme 7 were prepared as shown below in Scheme 8.

Scheme 8

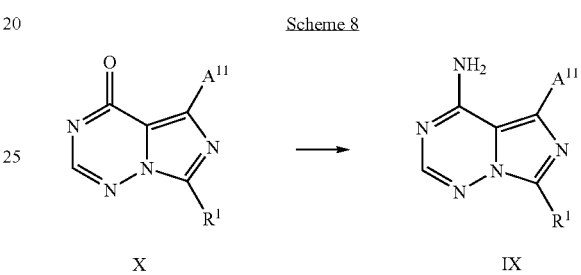

X          IX where $R^1$ is as defined previously for compound of Formula I and $A^{11}$=halogen such as Cl, Br, or I.

In a typical preparation of compounds of Formula IX, compound of Formula X was reacted with phosphorus oxychloride ($POCl_3$) and triazole, and pyridine followed by ammonia ($NH_3$) in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −20° C. and about 50° C. Preferably, the reaction was carried out between 0° C. and about 25° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula X of Scheme 8 were prepared as shown below in Scheme 9.

Scheme 9

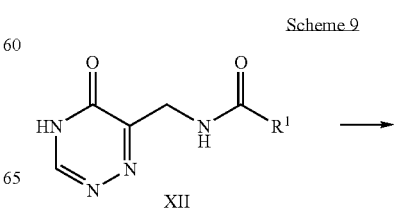

XII

-continued

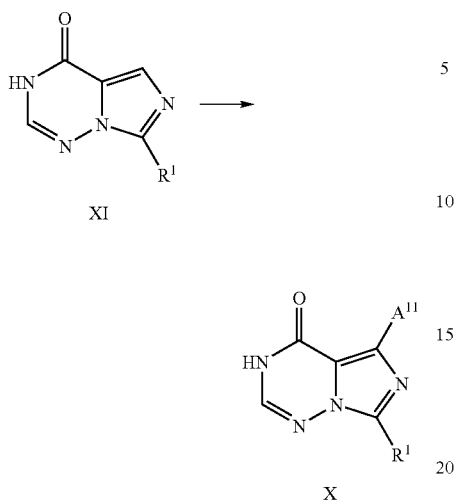

XI

X

The compounds of Formula XII of Scheme 9 were prepared as shown below in Scheme 10:

Scheme 10

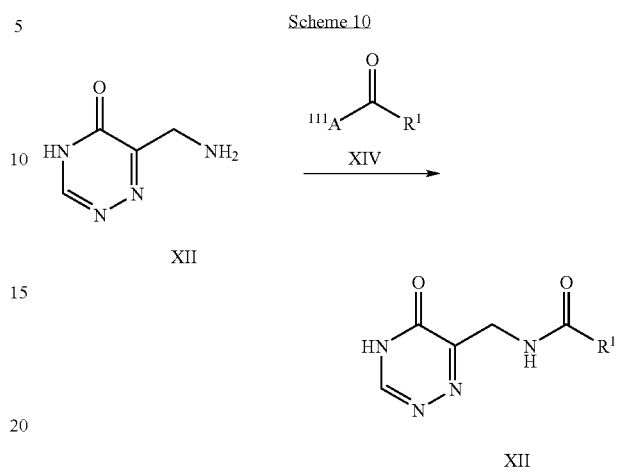

XII

XII where $R^1$ is as defined previously for compound of Formula I and $A^{11}$=halogen such as Cl, Br, or I.

In a typical preparation of a compound of Formula X, compound XII was converted to compound of Formula XI. Compound of Formula XII was treated with phosphorus oxychloride ($POCl_3$) in a suitable solvent at a suitable reaction temperature. Suitable solvents for use in the above process included, but were not limited to, ethers such as tetrahydrofuran (THF), glyme, and the like, chlorinated solvents such as methylene chloride ($CH_2Cl_2$) or chloroform ($CHCl_3$), and acetonitrile ($CH_3CN$). If desired, mixtures of these solvents were used. The preferred solvent was acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Compounds for Formula X was prepared by reacting compound of Formula XI with a suitable halogenating agent. Suitable halogenating agents included, but were not limited to, $Br_2$, $I_2$, $Cl_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially, equimolar amounts of reactants were preferably used although higher or lower amounts were used if desired.

where $R^1$ is as defined previously for compound of Formula I and $A^{111}$=OH, alkoxy, or a leaving group such as chloro or imidazole.

In a typical preparation, of a compound of Formula XII, a compound of Formula XIII and compound of Formula XIV were reacted under suitable amide coupling conditions. Suitable conditions include but are not limited to treating compounds of Formula XIII and XIV (when $A^{111}$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. Alternatively, compounds of Formula XIII and XIV (where $A^{111}$=Cl, Br) were reacted with bases such as triethylamine (TEA) or N,N'-diisopropylethylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; pyridine; halogenated solvents such as chloroform or methylene chloride. If desired, mixtures of these solvents were used, however the preferred solvent was DMF. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially, equimolar amounts of compounds of Formula XIII and XIV (where $A^{111}$=Cl, Br) and base and substochiometric amounts of DMAP were preferably used although higher or lower amounts were used if desired. Additionally, other suitable reaction conditions for the conversion of an amine (compound of Formula XIII) to an amide (compound of Formula XII) can be found in Larock, R. C. *Comprehensive Organic Transformations*, 2$^{nd}$ ed.; Wiley and Sons: New York, 1999, pp 1941-1949.

The compounds of Formula XIII of Scheme 10 were prepared as shown below in Scheme 11:

Scheme 11

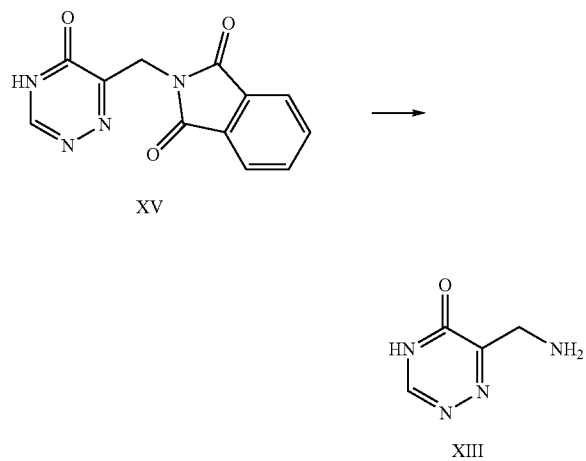

XV

XIII

In a typical preparation, of a compound of Formula XIII, a compound of Formula XV is reacted under suitable reaction conditions in a suitable solvent. Suitable conditions include treatment of compound of Formula XV with hydrazine or alkyl hydrazine derivatives in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcohol solvents such as methanol and ethanol. If desired, mixtures of these solvents may be used, however the preferred solvents were ethanol and methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula XV of Scheme 11 were prepared as shown below in Scheme 12:

Scheme 12

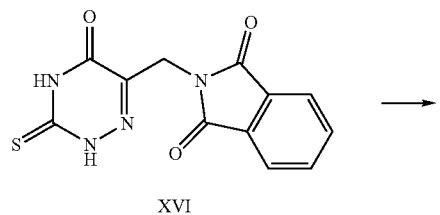

XVI

-continued

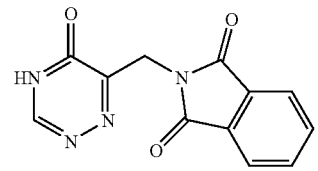

XV

In a typical preparation of a compound of Formula XV, a compound of Formula XVI was reacted with Raney Nickel in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); alcohols such as methanol, ethanol, isopropanol, trifluoroethanol, and the like; chlorinated solvents such as methylene chloride (CH$_2$Cl$_2$) or chloroform (CHCl$_3$). If desired, mixtures of these solvents were used, however, the preferred solvent was ethanol. The above process may be carried out at temperatures between about rt and about 100° C. Preferably, the reaction was carried out at about 80° C. The above process to produce compounds of the present invention was preferably carried out at about atmospheric pressure although higher or lower pressures were used if desired. Substantially, equimolar amounts of reactants were preferably used although higher or lower amounts were used if desired. Additionally a compound of Formula XV can be prepared by reacting a compound of Formula XVI with a suitable oxidizing agent in a suitable solvent. A suitable oxidizing agent includes, but is not limited to hydrogen peroxide (H$_2$O$_2$), 3-chloroperoxybenzoic acid (mCPBA) and the like. Suitable solvents for use in the above process included, but were not limited to, ethers such as THF, glyme, and the like; DMF; DMSO; CH$_3$CN; and dimethylacetamide (DMA); chlorinated solvents such as CH$_2$Cl$_2$ or CHCl$_3$. If desired, mixtures of these solvents were used, however, the preferred solvent was DMA. The above process may be carried out at temperatures between about 0° C. and 100° C. Preferably, the reaction was carried out at about rt to 70° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula XVI of Scheme 12 were prepared as shown below in Scheme 13:

Scheme 13

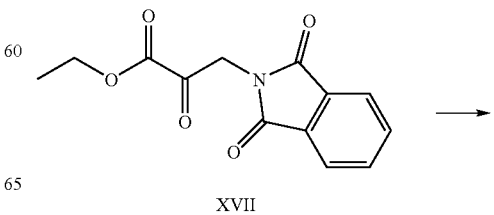

XVII

-continued

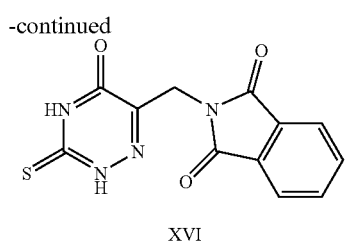

XVI

In a typical preparation of a compound of Formula XVI, a compound of Formula XVII was reacted with thiosemicarbazide and a suitable base in a suitable solvent. Suitable bases include, but were not limited to triethylamine, N,N'-diisopropylethylamine (DIEA) and the like. Suitable solvents for use in the above process included, but were not limited to, ethers such as tetrahydrofuran (THF), glyme, and the like; dimethylformamide (DMF); dimethylacetamide (DMA); dimethyl sulfoxide (DMSO); acetonitrile ($CH_3CN$); alcohols such as methanol (MeOH), ethanol (EtOH, isopropanol (i-PrOH), trifluoroethanol, and the like; chlorinated solvents such as methylene chloride ($CH_2Cl_2$) or chloroform ($CHCl_3$). If desired, mixtures of these solvents were used, however, the preferred solvent was ethanol. The above process may be carried out at temperatures between about rt and about 100° C. Preferably, the reaction was carried out between about 40° C. and 80° C. The above process to produce compounds of the present invention was preferably carried out at about atmospheric pressure although higher or lower pressures were used if desired. Substantially, equimolar amounts of reactants were preferably used although higher or lower amounts were used if desired. Compound of Formula XVII can be prepared according to literature procedures Knutsen, Lars J. S. et. al., *J. Chem. Soc. Perkin Trans* 1: *Organic and Bio-Organic Chemistry* (1972-1999), 1984, 229-238.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Throughout Scheme 1-13, $R^1$ can be optionally substituted with a suitable functional group that can be further modified. For example, $R^1$ in compound of Formula I, can equal cyclohexyl-4-$CO_2$Me. The 4-$CO_2$Me functional group can be subsequently converted into $CH_2OH$ via treatment with a suitable reducing agent such as lithium aluminum hydride. The alcohol, $CH_2OH$, can be further converted into a suitable leaving group such as a tosylate ($CH_2OTs$) or mesylate ($CH_2OMs$) followed by displacement with a suitable nucleophile such as dimethylamine to afford $CH_2N(CH_3)_2$.

The following examples are intended to illustrate and not to limit the scope of the present invention.

General Experimental Information:

All melting points were determined with a Mel-Temp II apparatus and are uncorrected. Commercially available anhydrous solvents and HPLC-grade solvents were used without further purification.

$^1$H NMR and $^{13}$C NMR spectra were recorded with Varian or Bruker instruments (400 MHz for $^1$H, 100.6 MHz for $^{13}$C) at ambient temperature with TMS or the residual solvent peak as internal standards. The line positions or multiplets are given in ppm (δ) and the coupling constants (J) are given as absolute values in Hertz, while the multiplicities in $^1$H NMR spectra are abbreviated as follows: s (singlet), d (doublet), t (triplet), q (quartet), quint (quintet), m (multiplet), $m_c$ (centered multiplet), br (broadened), AA'BB'. The signal multiplicities in $^{13}$C NMR spectra were determined using the DEPT135 pulse sequence and are abbreviated as follows: +(CH or $CH_3$), -($CH_2$), $C_{quart}$ (C). LC/MS analysis was performed using a Gilson 215 autosampler and Gilson 819 autoinjector attached to a Hewlett Packard HP1100 and a MicromassZQ mass spectrometer, or a Hewlett Packard HP1050 and a Micromass Platform II mass spectrometer. Both setups used XTERRA MS C18 5 μ 4.6×50 mm columns with detection at 254 nm and electrospray ionization in positive mode. For mass-directed purification (MDP), a Waters/Micromass system was used.

The tables below list the mobile phase gradients (solvent A: acetonitrile; solvent B: 0.01% formic acid in HPLC water) and flow rates for the analytical HPLC programs.

Polar_5 Min

| Time | A % | B % | Flow Rate (mL/min) MicromassZQ | Flow Rate (mL/min) Platform II |
|---|---|---|---|---|
| 0.00 | 5 | 95 | 1.3 | 1.3 |
| 3.00 | 90 | 10 | 1.3 | 1.3 |
| 3.50 | 90 | 10 | 1.3 | 1.3 |
| 4.00 | 5 | 95 | 1.3 | 1.3 |
| 5.00 | 5 | 95 | 1.3 | 1.3 |

Nonpolar_5 min

| Time | A % | B % | Flow Rate (mL/min) MicromassZQ | Flow Rate (mL/min) Platform II |
|---|---|---|---|---|
| 0.00 | 25 | 75 | 1.3 | 1.3 |
| 3.00 | 99 | 1 | 1.3 | 1.3 |
| 3.50 | 99 | 1 | 1.3 | 1.3 |
| 4.00 | 25 | 75 | 1.3 | 1.3 |
| 5.00 | 25 | 75 | 1.3 | 1.3 |

EXAMPLE 1

5-(3-benzyloxy-phenyl)-7-cyclobutyl-imidazo[5,1-f][1,2,4]triazin-4-ylamine (Compound of Formula I where R¹=cyclobutyl and Q¹=Ph-(3-OBn)) was prepared as follows:

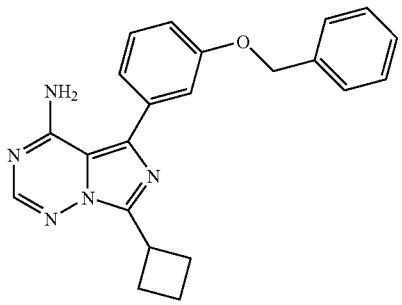

To a solution of 1,2,4-triazole (167 mg, 2.417 mmol) in anhydrous pyridine (1.5 mL) was added phosphorous oxychloride (POCl₃) (75 µL, 0.806 mmol) and stirred at rt for 15 min. To this mixture was added dropwise a solution of 5-(3-benzyloxy-phenyl)-7-cyclobutyl-3H-imidazo[5,1-f][1,2,4]triazin-4-one (100 mg, 0.269 mmol) in anhydrous pyridine (2.5 mL) over a 3.5 min period and stirred at rt for an additional 3 h. The reaction was cooled to 0° C. and quenched with 2M NH₃ in i-PrOH (10 mL) and stirred for an additional 30 min at rt. The mixture was filtered through a fritted funnel and the filtrate was concentrated in vacuo, partitioned between CHCl₃ and H₂O and separated. The aqueous layer was re-extracted with CHCl₃ (3×) and the combined CHCl₃ fractions were washed with brine (1×), dried over Na₂SO₄, filtered and concentrated in vacuo and the crude material was chromatographed on silica gel [eluting with 2% MEOH in CHCl₃] resulting in a dark brown oil which was crystallized from EtOAc/hexanes to obtain the title compound as a light tan solid. ¹H NMR (CDCl₃, 400 MHz) δ 1.95-2.08 (m, 1H), 2.09-2.22 (m, 1H), 2.39-2.50 (m, 2H), 2.59-2.72 (m, 2H), 4.14 (quint, J=8.4 Hz, 1H), 5.16 (s, 2H), 5.57 (brs, 2H), 7.02-7.09 (m, 1H), 7.22-7.28 (m, 3H), 7.31-7.50 (m, 5H), 7.85 (s, 1H); MS (ES+): m/z 372.1 (100) [MH⁺]; HPLC: $t_R$=3.05 min (MicromassZQ, nonpolar_5 min).

5-(3-benzyloxy-phenyl)-7-cyclobutyl-3H-imidazo[5,1-f][1,2,4]triazin-4-one (Compound of Formula II where R¹=cyclobutyl and Q¹=Ph-(3-OBn)) was prepared as follows:

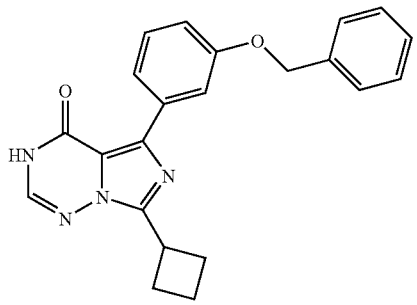

A solution of cyclobutanecarboxylic acid [(3-benzyloxy-phenyl)-(5-oxo-4,5-dihydro-[1,2,4]triazin-6-yl)-methyl]-amide (216 mg, 0.553 mmol) in POCl₃ (5 mL) was heated to 55° C. in an oil bath for 3 h. The reaction mixture was concentrated in vacuo and cooled to 0° C. and charged with 2M NH₃ in i-PrOH until slightly basic. The solution was concentrated in vacuo and the reaction mixture was partitioned between EtOAc and H₂O and separated. The aqueous layer was re-extracted with EtOAc (3×) and the combined EtOAc fractions were dried over Na₂SO₄, filtered and concentrated in vacuo to obtain the title compound as an off-white foam solid with no further purification. ¹H NMR (CDCl₃, 400 MHz) δ 1.98-2.07 (m, 1H), 2.08-2.21 (m, 1H), 2.36-2.48 (m, 2H), 2.62-2.77 (m, 2H), 4.09 (quint, J=8.8 Hz, 1H), 5.13 (s, 2H), 6.98 (dd, J=2.0, 7.2 Hz, 1H), 7.27-7.7.40 (m, 4H), 7.42-7.49 (m, 3H), 7.88 (d, J=8.0 Hz, 1H), 7.99 (brs, 1H); MS(ES+): m/z 373.1 (100) [MH⁺]; HPLC: $t_R$=3.25 min (MicromassZQ, nonpolar_5 min).

Cyclobutanecarboxylic acid [(3-benzyloxy-phenyl)-(5-oxo-4,5-dihydro-[1,2,4]triazin-6-yl)-methyl]-amide (Compound of Formula III where R¹=cyclobutyl and Q¹=Ph-(3-OBn)) was prepared as follows:

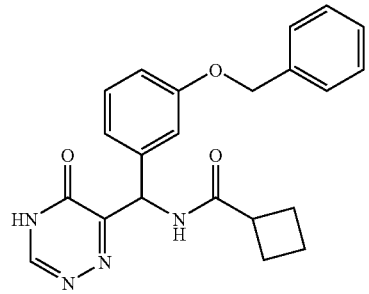

To a solution of cyclobutanecarboxylic acid [(4-amino-5-oxo-4,5-dihydro-[1,2,4]triazin-6-yl)-(3-benzyloxy-phenyl)-methyl]-amide (315 mg, 0.777 mmol) and concentrated HCl (344 µL) in anhydrous EtOH (16 mL) was dropwise added a solution of sodium nitrite (120 mg, 1.72 mmol) in H₂O (4 mL) at 0° C. and stirred for 30 min and warmed to rt for an additional 1.5 h. The reaction mixture was concentrated in vacuo and the crude material was chromatographed on silica gel [eluting with 3% MeOH in CHCl₃] to obtain the title compound as an off-white foam solid. ¹H NMR (CDCl₃, 400 MHz) δ 1.78-1.93 (m, 1H), 1.93-2.04 (m, 1H), 2.12-2.2.36 (m, 4H), 3.13 (quint, J=8.4 Hz, 1H), 4.97 (s, 2H), 6.35 (d, J=8.8 Hz, 1H), 6.85 (dd, J=2.4, 8.4 Hz, 1H), 6.96-7.05 (m, 2H), 7.20 (t, J=8.0 Hz, 1H), 7.27-7.41 (m, 4H), 7.61 (brs, 1H), 8.46 (s, 1H); MS (ES+): m/z 391.04 (100) [MH⁺]; HPLC: $t_R$=2.87 min (MicromassZQ, polar_5 min).

Cyclobutanecarboxylic acid [(4-amino-5-oxo-4,5-dihydro-[1,2,4]triazin-6-yl)-(3-benzyloxy-phenyl)-methyl]-amide (Compound of Formula IV where R$^1$=cyclobutyl and Q$^1$=Ph-(3-OBn)) was prepared as follows:

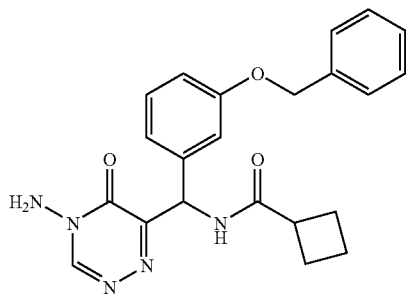

A solution of formamidine HCl (163 mg, 2.02 mmol) in anhydrous EtOH (8 mL) was cooled to 0° C. and was charged with a 1M solution of hydrazine in THF (4.05 mL, 4.05 mmol) over a 4 min period and stirred at rt for 8 min. The reaction mixture was cooled to −20° C. and charged with a solution of 3-(3-benzyloxy-phenyl)-3-(cyclobutanecarbonyl-amino)-2-oxo-propionic acid ethyl ester (800 mg, 2.02 mmol) in anhydrous EtOH (16 mL) over a 15 min period and stirred at −20° C. for an additional 15 min and allowed to warm to rt for 4 h. The reaction mixture was concentrated in vacuo and the crude material was chromatographed on silica gel [eluting with 3% MeOH in CHCl$_3$], yielding the title compound as a light yellow foam solid. $^1$H NMR (CDCl$_3$, 400 MHz) δ 1.78-2.04 (m, 2H), 2.08-2.34 (m, 4H), 3.07 (quint, J=8.4 Hz, 1H), 4.92 (s, 2H), 5.03 (s, 1H), 6.49 (d, J=8.0 Hz, 1H), 6.84-6.92 (m, 1H), 6.95-7.10 (m, 3H), 7.23 (t, J=8.0 Hz, 1H), 7.28-7.46 (m, 4H), 8.42 (s, 1H); MS (ES+): m/z 406.08 (100) [MH$^+$]; HPLC: t$_R$=3.04 min (MicromassZQ, polar_5 min).

3-(3-benzyloxy-phenyl)-3-(cyclobutanecarbonyl-amino)-2-oxo-propionic acid ethyl ester (Compound of Formula V where R$^1$=cyclobutyl and Q$^1$=Ph-(3-OBn)) was prepared as follows:

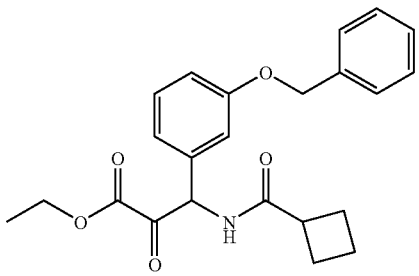

A slurry of (3-benzyloxy-phenyl)-(cyclobutanecarbonyl-amino)-acetic acid (4.77 g, 14.1 mmol), pyridine (3.4 mL, 42.2 mmol) and DMAP (cat.) in anhydrous THF (26 mL) was charged dropwise with chloro-oxo-acetic acid ethyl ester (3.13 mL, 28.1 mmol) and heated to reflux for 1.5 h. The white precipitate was filtered through a fritted glass Buchner funnel into a flask containing H$_2$O and EtOAc and the aqueous phase was separated from the organic phase. The aqueous was washed with EtOAc (3×) and the combined EtOAc layers were washed with brine (1×), dried over Na$_2$SO$_4$, filtered and concentrated in vacuo resulting in a yellow/orange oil. The oil was dissolved in anhydrous EtOH (28 mL) and a solution of 21 wt % of sodium ethoxide (NaOEt) in EtOH (2.0 mnL) was added at 0° C. and warmed to rt. The reaction mixture was concentrated in vacuo and the crude material was chromatographed on silica gel [eluting with 2% EtOAc in CHCl$_3$], yielding the title compound as a pale yellow oil. $^1$H NMR (CDCl$_3$, 400 MHz) δ 1.26 (t, J=7.2 Hz, 3H), 1.80-2.04 (m, 2H), 2.09 (m, 4H), 3.06 (quint, J=8.4 Hz, 1H) 4.17-4.30 (m, 2H), 5.04 (s, 2H), 6.18-6.32 (m, 2H), 6.86-7.00 (m, 3H), 7.22-7.48 (m, 5H); MS (ES+): m/z 396.03 (100) [MH$^+$]; HPLC: t$_R$=3.09 min (MicromassZQ, nonpolar_5 min).

EXAMPLE 2

5-(3-benzyloxy-2-fluoro-phenyl)-7-cyclobutyl-imidazo[5,1-f][1,2,4]triazin-4-ylamine (compound of Formula I where R$^1$=cyclobutyl and Q$^1$=2-fluoro-Ph-(3-OBn)) was prepared as follows:

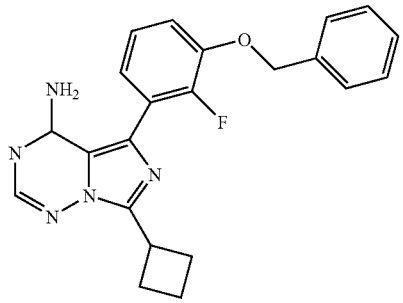

A flask was charged with 7-cyclobutyl-5-iodo-imidazo[5,1-f][1,2,4]triazin-4-ylamine (30 mg, 0.095 mmol), 2-(3-benzyloxy-2-fluoro-phenyl)-4,4,5,5- tetramethyl [1,3,2]dioxaborolane (62.5 mg, 0.158 mmol), and sodium carbonate (30 mg, 0.286 mmol) and was evacuated and charged with N$_2$ (3×). This mixture was charged with tetrakis(triphenylphosphine palladium (0) (Pd(PPh$_3$)$_4$ (0)) (36 mg, 0.0318 mmol) and the tube was re-evacuated and charged with N$_2$ (2×). This mixture was then charged with a previously degassed solvent DME/H$_2$O (5:1)(3 mL) and heated to 75° C. for 16 h. The reaction mixture was concentrated in vacuo and dissolved in MeOH/CH$_3$CN (1:1) (5 mL), filtered though a 0.45 μM fritted autovial and submitted for mass directed purification (MDP) resulting in the title compound as a white solid.

$^1$H NMR (DMSO-d$_6$, 400 MHz) δ 1.86-1.98 (m, 1H), 2.00-2.14 (m, 1H), 2.30-2.41 (m, 2H), 2.41-2.48 (m, 2H), 3.98-4.09 (m, 1H), 5.24 (s, 2H), 6.27 (brs, 1H), 7.05-7.12 (m, 1H), 7.22 (t, J=8.27 Hz, 1H), 7.29-7.52 (m, 6H), 7.88 (s, 1H), 8.15 (brs, 1H); MS (ES+): m/z 389.98 (100), [MH$^+$], HPLC: t$_R$=3.44 min (MicromassZQ, polar_5 min).

7-cyclobutyl-5-iodo-imidazo[5,1-f][1,2,4]triazin-4-ylamine (Compound of Formula IX where R¹=cyclobutyl and A¹¹=iodine) was prepared as follows:

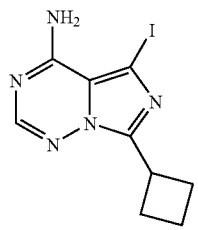

To a solution of 1,2,4-triazole (1.28 g, 18.59 mmol) in anhydrous pyridine (10 mL) was added phosphorus oxychloride (POCl₃) (0.578 mL, 6.20 mmol) and stirred at rt for 15 min. This mixture was dropwise charged (3.5 min) with a solution of 7-cyclobutyl-5-iodo-3H imidazo[5,1f][1,2,4]triazin-4-one (0.653 mg, 2.07 mmol) in anhydrous pyridine (14 mL) and stirred for 1.5 h. The reaction mixture was cooled to 0° C. quenched with 2M NH₃ in isopropanol (i-PrOH) until basic then allowed to reach rt and stirred for an additional 2 h. The reaction mixture was filtered through a fritted Buchner funnel and washed with CH₂Cl₂. The filtrate was concentrated in vacuo and purified by chromatography on silica gel [eluting with 30% EtOAc in CH₂Cl₂] resulting in the title compound as an off-white solid; ¹H NMR (CDCl₃, 400 MHz) δ 1.93-2.04 (m, 1H), 2.05-2.18 (m, 1H), 2.35-2.45 (m, 2H), 2.49-2.62 (m, 2H), 4.00-4.12 (m, 1H), 7.82 (s, 1H); MS (ES+): m/z 316.08 (100) [MH⁺], HPLC: t$_R$=2.59 min (MicromassZQ, polar_5 min).

7-cyclobutyl-5-iodo-3H-imidazo[5,1-f][1,2,4]triazin-4-one (compound of Formula X where R¹=cyclobutyl and A¹¹=iodine) was prepared as follows:

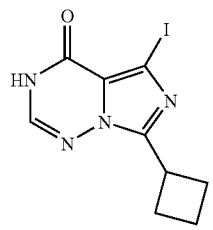

A solution of 7-cyclobutyl-3H-imidazo[5,1-f][1,2,4]triazin-4-one (789 mg, 4.15 mmol) and N-iodosuccinimide (933 mg, 4.15 mmol) in anhydrous DMF (40 mL) was stirred overnight at rt. An additional 4 equiv of N-iodosuccinimide was added and reaction was heated to 55° C. for 6 h. The reaction mixture was concentrated in vacuo and partitioned between CH₂Cl₂ and H₂O and separated. The aqueous layer was washed with CH₂Cl₂ (3×) and the combined organic fractions were washed with 1M sodium thiosulfate (Na₂S₂O₃) (1×), brine (1×), dried over sodium sulfate (Na₂SO₄), filtered, and concentrated in vacuo. The solid was triturated with 20% EtOAc in DCM and filtered through a fritted Buchner funnel resulting in the title compound as an off-white solid; ¹H NMR (DMSO-d₆, 400 MHz) δ 1.84-1.96 (m, 1H), 1.98-2.13 (m, 1H), 2.25-2.43 (m, 4H), 3.84-3.96 (m, 1H), 7.87 (s, 1H); MS (ES+): m/z 317.02 (100) [MH⁺], HPLC: t$_R$=2.62 min (MicromassZQ, polar_5 min).

7-cyclobutyl-3H-imidazo[5,1-f][1,2,4]triazin-4-one (Compound of Formula XI where R¹=cyclobutyl) was prepared as follows:

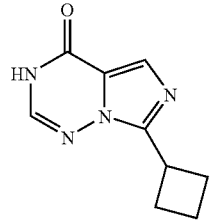

A solution of cyclobutanecarboxylic acid (5-oxo-4,5-dihydro-[1,2,4]triazin-6-ylmethyl)-amide (1.33 g, 6.39 mmol) in phosphorus oxychloride (POCl₃) (10 mL) was heated to 55° C. The reaction was heated for 2 h then concentrated in vacuo and the crude oil was cooled to 0° C. in an ice-bath and quenched with 2 M NH₃ in isopropanol (i-PrOH) until slightly basic. This crude reaction mixture was concentrated in vacuo and was partitioned between CH₂Cl₂ and H₂O and separated. The aqueous layer was extracted with CH₂Cl₂ (3×) and the combined organic fractions were dried over sodium sulfate (Na₂SO₄), filtered and concentrated in vacuo. The crude material was purified by chromatography on silica gel [eluting with 5% MeOH in CH₂Cl₂], resulting in the title compound as an off-white solid; ¹H NMR (DMSO-d₆, 400 MHz) δ 1.86-1.96 (m, 1H), 2.00-2.13 (m, 1H); 2.26-2.46 (m, 4H); 3.87-4.00 (m, 1H); 7.71 (s, 1H); 7.87 (d, J=3.6 Hz, 1H); 11.7 (brs, 1H); MS (ES+): m/z 191.27 (100) [MH⁺], HPLC: t$_R$=2.06 min (MicromassZQ, polar_5 min).

Cyclobutanecarboxylic acid (5-oxo-4,5-dihydro-[1,2,4]triazin-6-ylmethyl)-amide (compound of Formula XII where R¹=cyclobutyl) was prepared as follows:

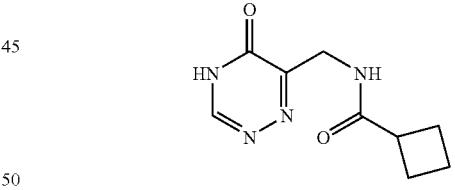

To a solution of 6-aminomethyl-4H-[1,2,4]triazin-5-one (500 mg, 3.96 mmol) and N,N'-diisopropylethylamine (DIEA) (0.829 mL, 4.76 mmol) in anhydrous N,N'-dimethylforamide (DMF) (20 mL) and anhydrous pyridine (2 mL) was dropwise charged with cyclobutanecarbonyl chloride (0.451 mL, 3.96 mmol) at 0° C. then warmed to rt and stirred for an additional 1.5 h. The reaction mixture was quenched with H₂O (2 mL), concentrated in vacuo, and purified by chromatography on silica gel [eluting with 5% MeOH in CH₂Cl₂ (200 mL)→10% MeOH in CH₂Cl₂ (800 mL)], affording the title compound; ¹H NMR (DMSO-d₆, 400 MHz) δ 1.7-1.82 (m, 1H), 1.70-1.92 (m, 1H); 1.97-2.07 (m, 2H); 2.07-2.19 (m, 2H); 3.55-3.67 (m, 1H); 4.19 (d, 2H); 7.97 (brt, J=5.6 Hz, 1H); 8.67 (s, 1H); MS (ES+): m/z 209.25 (100) [MH⁺], HPLC: t$_R$=1.56 min (MicromassZQ, polar_5 min).

6-aminomethyl-4H-[1,2,4]triazin-5-one (Compound of Formula XIII) was prepared as follows:

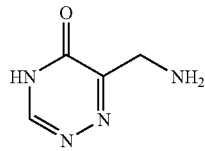

A slurry of 2-(5-oxo-4,5-dihydro-[1,2,4]triazin-6-ylmethyl)-isoindole-1,3-dione (4 g, 15.6 mmol) in CH$_2$Cl$_2$/EtOH (1:1) (150 mL) was charged with anhydrous hydrazine (1.23 mL, 39.0 mmol) and stirred at rt for 18 h. The reaction mixture was concentrated in vacuo and the off-white solid was triturated with warm CHCl$_3$ and filtered through a fritted funnel. The solid was then triturated with hot methanol (MeOH) and filtered through a fritted funnel resulting in an off-white solid. The material was triturated a second time as before and dried overnight resulting in the title compound as a white solid, which was taken on to the next step without further purification; $^1$H NMR (DMSO-d$_6$, 400 MHz) δ 3.88(s, 2H), 8.31 (2, 1H); MS (ES+): m/z 127.07 (100) [MH$^+$], HPLC: t$_R$=0.34 min (MicromassZQ, polar_5 min).

2-(5oxo-4,5-dihydro-[1,2,4]triazin-6-ylmethyl)-isoindole-1,3-dione (Compound of Formula XV) was prepared as follows:

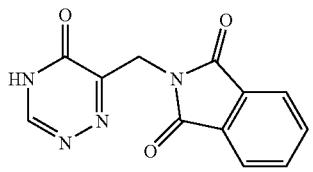

A slurry of 2-(5-oxo-3-thioxo-2,3,4,5-tetrahydro-[1,2,4]triazin-6-ylmethyl)-isoindole-1,3-dione (1.0 g, 3.47 mmol) in EtOH (40 mL) was charged with excess Raney Nickel (3 spatula) and heated to reflux for 2 h. The reaction mixture was filtered hot through a small pad of celite and washed with a hot mixture of EtOH/THF (1:1) (100 mL) and the filtrate was concentrated in vacuo resulting in the title compound as an off-white solid; $^1$H NMR (DMSO-d$_6$, 400 MHz) δ 4.75 (s, 2H), 7.84-7.98 (m, 4H), 8.66 (s, 1H); MS (ES+): m/z 257.22 (100) [MH$^+$], HPLC: t$_R$=2.08 min (MicromassZQ, polar_5 min).

2-(5-oxo-3-thioxo-2,3,4,5-tetrahydro-[1,2,4]triazin-6-ylmethyl)-indan-1,3-dione (Compound of Formula XVI) was prepared as follows:

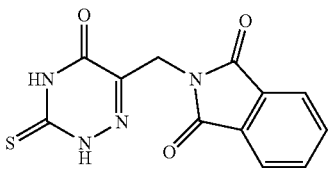

A slurry of 3-(1,3-dioxo-1,3-dihydro-isoindol-2-yl)-2-oxo-propionic acid ethyl ester (20 g, 76.6 mmol) in anhydrous EtOH (300 mL) was charged with thiosemicarbazide (6.98 g, 76.6 mmol) in one portion and heated to 80° C. for 2 h. The reaction mixture was charged with N,N'-diisopropylethylamine (DIEA) (26.7 mL, 76.56 mmol) and heated to 40° C. for 6 h then stirred at rt for an additional 10 h. The reaction mixture was concentrated in vacuo and solid was triturated with hot EtOH/EtOAc filtered and washed with EtOAc. The solid was dried overnight in a vacuum oven (40° C.) resulting in the title compound as an off-white solid; $^1$H NMR (DMSO-d$_6$, 400 MHz) δ 4.68 (s, 2H), 7.85-7.95 (m, 4H); MS (ES+): m/z 289.2 (100) [MH$^+$], HPLC: t$_R$=2.50 min (MicromassZQ, polar_5 min).

2-fluoro-3-benzyloxyphenylboronic acid pinacol ester (Compound of Formula XVIII where Q$^1$=2-fluoro-Ph) was prepared as follows:

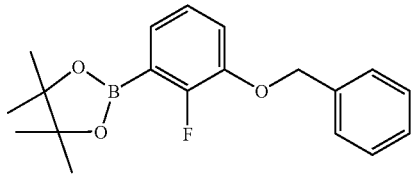

A mixture of 1-(benzyloxy)-3-chloro-2-fluorobenzene (7.1 g, 30.0 mmol), bis(pinacol)diboron (9.142 g, 36.0 mmol), Palladium(II) acetate (0.337 g, 1.50 mmol), potassium acetate (7.711 g, 78.6 mmol) and 1,3-bis(2,6-diisopropylphenyl)imidazolium chloride (0.9 g, 2.12 mmol) in THF was refluxed under nitrogen overnight. The mixture was diluted with ethyl acetate (100 mL) and brine (30 mL), then filtered through celite. The yellow liquid was then separated and the organic layer was dried over anhydrous sodium sulfate. Concentration of the liquid under reduced pressure gave a grey solid, which was recrystallized from hexanes to give the title compound as a white powder. $^1$H NMR (CDCl3, 400 MHz) δ 1.37(s, 12 Hs), 5.18(s, 2H), 7.04-7.18(m, 2Hs), 7.27-7.47(m, 6H).

1-(benzyloxy)-3-chloro-2-fluorobenzene

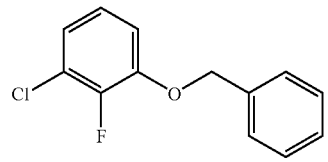

A mixture of 3-chloro-2-fluorophenol (1.5 g, 10.2 mmol), benzyl bromide (1.71 g, 10.0 mmol) and sodium carbonate (1.10 g, 10.38 mmol) in 20 mL ethylene glycol dimethyl ether and 10 mL H$_2$O was stirred at rt for 36 h. The reaction mixture was charged with 20 mL 1N KOH and 50 mL diethyl ether. The organic layer was separated, washed with brine, dried over sodium sulfate, and concentrated in vacuo to afford the title compound as a white solid which was used without further purification. $^1$H NMR (CDCl$_3$, 400 MHz) δ 5.16 (s, 2Hs) 6.86-7.03 (m, 3Hs) 7.31-7.48 (m, 5Hs).

What is claimed is:
1. A compound represented by Formula I:

or a pharmaceuticaly acceptable salt thereof, wherein:
$Q^1$ is phenyl substituted by $-(X^1)_{0-1}-(Y^1)_{0-1}-R^4$ wherein $X^1$ is 3-(O)—, 4-(O)—, 3-(NH)—, or 4-(NH)—; and $Y^1$ is $-CH_2-$ or $-(SO_2)-$;

$R^4$ is $C_{0-10}$alkyl, $C_{2-10}$alkenyl, $C_{2-10}$alkynyl, aryl, heteroaryl, cyclo$C_{3-10}$alkyl, heterocyclyl, cyclo$C_{3-10}$alkenyl, or heterocycloalkenyl, any of which is optionaly substituted by one or more independent $G^{41}$ substituents;

$R^1$ is $C_{0-10}$alkyl, cyclo$C_{3-10}$alkyl, bicyclo$C_{5-10}$alkyl, aryl, heteroaryl, aralkyl, heteroaralkyl, heterocyclyl, or heterobicyclo$C_{5-10}$alkyl, any of which is optionaly substituted by one or more independent $G^{11}$ substituents;

each $G^{11}$ is independently $-OR^{21}$, $-NR^{21}R^{31}$, $-CO_2R^{21}$, $-C(O)R^{21}$, $-CONR^{21}R^{31}$, $-NR^{21}C(=O)R^{31}$, $-NR^{21}C(=O)OR^{31}$, $-NR^{21}C(=O)NR^{31}R^{21a}$, $-NR^{21}S(O)_{j3}R^{31}$, $-OC(=O)OR^{21}$, $-OC(=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionaly substituted with one or more independent halo, oxo, $-CF_3$, $-OCF_3$, $-OR^{2221}$, $-NR^{2221}R^{3331}(R^{2221}a)_{j3a}$, $-C(O)R^{2221}$, $-CO_2R^{2221}$, $-CONR^{2221}R^{3331}$, $-NO_2$, $-CN$, $-S(O)_{j3a}R^{2221}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-C(=S)OR^{2221}$, $-C(=O)SR^{2221}$, $-NR^{2221}C(=NR^{3331})NR^{2221a}R^{3331a}$, $-NR^{2221}C(=NR^{3331})OR^{2221a}$, $-NR^{2221}C(=NR^{3331})SR^{2221a}$, $-OC(=O)OR^{2221}$, $-OC(=O)NR^{2221}R^{3331}$, $-OC(=O)SR^{2221}$, $-SC(=O)OR^{2221}$, or $-SC(=O)NR^{2221}R^{3331}$;

each $G^{41}$ is independently halo, oxo, $-CF_3$, $-OCF_3$, $-OR^2$, $-NR^2R^3(R^{2a})_{j1}$, $-C(O)R^2$, $-CO_2R^2$, $-CONR^2R^3$, $-NO_2$, $-CN$, $-S(O)_{j1}R^2$, $-SO_2NR^2R^3$, $-NR^2C(=O)R^3$, $-NR^2C(=O)OR^3$, $-NR^2C(=O)NR^3R^{2a}$, $-NR^2S(O)_{j1}R^3$, $-C(=S)OR^2$, $-C(=O)SR^2$, $-NR^2C(=NR^3)NR^{2a}R^{3a}$, $-NR^2C(=NR^3)OR^{2a}$, $-NR^2C(=NR^3)SR^{2a}$, $-OC(=O)OR^2$, $-OC(=O)NR^2R^3$, $-OC(=O)SR^2$, $-SC(=O)OR^2$, $-SC(=O)NR^2R^3$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionaly substituted with one or more independent halo, oxo, $-CF_3$, $-OCF_3$, $-OR^{222}$, $-NR^{222}R^{333}(R^{222a})_{j1a}$, $-C(O)R^{222}$, $-CO_2R^{222}$, $-CONR^{222}R^{333}$, $-NO_2$, $-CN$, $-S(O)_{j1a}R^{222}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(O)_{j1a}R^{333}$, $-C(=S)OR^{222}$, $-C(=S)SR^{222}$, $-NR^{222}C(=NR^{333})NR^{222a}R^{333a}$, $-NR^{222}C(=NR^{333})OR^{222a}$, $-NR^{222}C(=NR^{333})SR^{222a}$, $-OC(=O)OR^{222}$, $-OC(=O)NR^{222}R^{333}$, $-OC(=O)SR^{222}$, $-SC(=O)OR^{222}$, or $-SC(=O)NR^{222}R^{333}$ substituents;

or $G^{41}$ can be independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionaly substituted with one or more independent halo, $-CF_3$, $-OCF_3$, $-OR^{222}$, $-NR^{222}R^{333}(R^{222a})_{j2a}$, $-C(O)R^{222}$, $-CO_2R^{222}$, $-CONR^{222}R^{333}$, $-NO_2$, $-CN$, $-S(O)_{j2a}R^{222}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(O)_{j2a}R^{333}$, $-C(=S)OR^{222}$, $-C(=O)SR^{222}$, $-NR^{222}C(=NR^{333})NR^{222a}R^{333a}$, $-NR^{222}C(=NR^{333})OR^{222a}$, $-NR^{222}C(=NR^{333})SR^{222a}$, $-OC(=O)OR^{222}$, $-OC(=O)NR^{222}R^{333}$, $-OC(=O)SR^{222}$, $-SC(=O)OR^{222}$, or $-SC(=O)NR^{222}R^{333}$ substituents;

$R^2$, $R^{2a}$, $R^3$, $R^{3a}$, $R^{222}$, $R^{222a}$, $R^{333}$, $R^{333a}$, $R^{21}$, $R^{21a}$, $R^{31}$, $R^{2221}$, $R^{2221a}$, $R^{3331}$, and $R^{3331a}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionaly substituted by one or more independent $G^{13}$ substituents;

or in the case of $-NR^2R^3(R^{2a})_{j1}$ or $-NR^{21}R^{31}(R^{21a})_{j3}$ or $-NR^{222}R^{333}(R^{222a})_{j1a}$ or $-NR^{222}R^{333}(R^{222a})_{j2a}$ or $-NR^{2221}R^{3331}(R^{2221a})_{j3a}$, $R^2$ and $R^3$, or $R^{21}$ and $R^{31}$, or $R^{222}$ and $R^{333}$, or $R^{3331}$, or $R^{2221}$ and $R^{3331}$, respectfuly, are optionaly taken together with the nitrogen atom to which they are attached to form a 3-10 membered saturated or unsaturated ring, wherein said ring is optionaly substituted by one or more independent $G^{14}$ substituents and wherein said ring optionaly includes one or more independent heteroatoms other than the nitrogen to which $R^2$ and $R^3$, or $R^{222}$ and $R^{333}$, or $R^{222}$ and $R^{3331}$, are attached;

$G^{13}$ and $G^{14}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionaly substituted with one or more independent halo, $-CF_3$, $-OCF_3$, $-OR^{77}$, $-NR^{77}R^{87}$, $-C(O)R^{77}$, $-CO_2R^{77}$, $-CONR^{77}R^{87}$, $-NO_2$, $-CN$, $-S(O)_{j5a}R^{77}$, $-SO_2NR^{77}R^{87}$, $-NR^{77}C(=O)R^{87}$, $-NR^{77}C(=O)OR^{87}$, $-NR^{77}C(=O)NR^{87}R^{77a}$, $-NR^{77}S(O)_{j5a}R^{87}$, $-C(=S)OR^{77}$, $-C(=O)SR^{77}$, $-NR^{77}C(=NR^{87})$ $NR^{77a}R^{87a}$, $-NR^{77}C(=NR^{87})OR^{77a}$, $-NR^{77}C(=NR^{87})SR^{77a}$, $-OC(=O)OR^{77}$, $-OC(=O)NR^{77}R^{87}$, $-OC(=O)SR^{77}$, $-SC(=O)OR^{77}$, $-P(O)OR^{77}OR^{87}$, or $-SC(=O)NR^{77}R^{87}$ substituents;

$R^{41}$, $R^{51}$, $R^{77}$, $R^{77a}$, $R^{87}$, $R^{87a}$, $R^{778}$, and $R^{888}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{2-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl-$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, $C_{1-10}$alkyl(aryl)aminocarbonyl, monohetarylaminocarbonyl, dihetarylaminocarbonyl, or alkylhetarylaminocarbonyl, any of which is optionaly substituted with one or more independent halo, cyano, hydroxy, nitro, $C_{1-10}$alkoxy, $-SO_2N(C_{0-4}$alkyl)($C_{0-4}$alkyl), or $-N(C_{0-4}$alkyl)($C_{0-4}$alkyl) substituents;

or $R^{77}$, $R^{77a}$, $R^{87}$, and $R^{87a}$ are each independently aryl-$C_{0-10}$alkyl, aryl-$C_{2-10}$alkenyl aryl-$C_{2-10}$alkynyl, hetaryl-$C_{0-10}$alkyl, hetaryl-$C_{2-10}$alkenyl, hetaryl-$C_{2-10}$alkynyl, mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, monohetarylaminoalkyl, dihetarylaminoalkyl, or $-N(C_{1-6}$alkyl)-$C_{1-6}$alkyl-aryl, any of which is optionaly substituted with one or more independent halo, cyano, nitro, $-O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CON(C_{0-4}$alkyl)($C_{0-4}$alkyl), $-SO_2N(C_{0-4}$alkyl)($C_{0-4}$alkyl), or $-N(C_{0-4}$alkyl)($C_{0-4}$alkyl) substituents; and j1, j1a, j2a, j3, j3a, and j5a are each independently 0, 1, or 2.

2. The compound or salt of claim 1 wherein $X^1$ is 3-(O)— or 4-(O)—; $Y^1$ is $-CH_2$—; and n and m are each 1.

3. The compound or salt of claim 2 wherein $R^4$ is aryl, $C_{0-10}$alkyl, or cyclo$C_{3-10}$alkyl, any of which is optionaly substituted by one or more independent $G^{41}$ substituents.

4. The compound or salt of claim 2 wherein $R^4$ is phenyl optionally substituted by one or more independent $G^{41}$ substituents.

5. The compound or salt of claim 3 wherein $R^1$ is aryl, heteroaryl, cyclo$C_{3-10}$alkyl, or heterocyclyl, any of which is optionaly substituted by $G^{11}$.

6. The compound or salt of claim 3 wherein $R^1$ is cyclo$C_{3-10}$alkyl which is optionaly substituted by $G^{11}$.

7. The compound or salt of claim 3 wherein $R^1$ is represented by the structural formula:

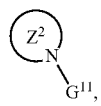

wherein $Z^2$ is a heterocyclyl.

8. The compound or salt of claim 3 wherein $R^1$ is represented by the structural formula:

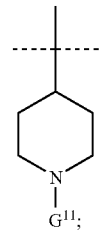

wherein $G^{11}$ is $-C(O)R^{21}$, $-CO_2R^{21}$, $-CONR^{21}R^{31}$, $-SO_2NR^{21}R^{31}$, $-S(O)_{j3}R^{31}$, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent oxo $-CF_3$, $-OCF_3$, $-OR^{2221}$, $-NR^{2221}R^{3331}$, $-C(O)R^{2221}$, $-CO_2R^{2221}$, $-CONR^{2221}R^{3331}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-NR^{2221}C(=NR^{3331})NR^{2221a}R^{3331a}$, or $-OC(=O)NR^{2221}R^{3331}$ substituents;

or $G^{11}$ is aryl-$C_{0-10}$alkyl or hetaryl-$C_{0-10}$alkyl, any of which is optionaly substituted with one or more independent halo, $-CF_3$, $-OCF_3$, $-OR^{2221}$, $-NR^{2221}R^{3331}$, $-C(O)R^{2221}$, $-CO_2R^{2221}$, $-CONR^{2221}R^{3331}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-NR^{2221}C(=NR^{3331})NR^{2221a}R^{3331a}$, or $-OC(=O)NR^{2221}R^{3331}$ substituents.

9. The compound or salt of claim 1 wherein $R^1$ is represented by the structural formula:

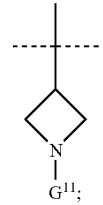

wherein $G^{11}$ is $-C(O)R^{21}$, $-CO_2R^{21}$, $-CONR^{21}R^{31}$, $-SO_2NR^{21}R^{31}$, $-S(O)_{j3}R^{31}$, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent oxo $-CF_3$, $-OCF_3$, $-OR^{2221}$, $-NR^{2221}R^{3331}$, $-C(O)R^{2221}$, $-CO_2R^{2221}$, $-CONR^{2221}R^{3331}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{2221a}$, $-NR^{2221}S(O)_{j3a}R^{3331}$, $-NR^{2221}C(=NR^{3331})NR^{2221a}R^{3331a}$, or $-OC(=O)NR^{2221}R^{3331}$ substituents;

or aryl-$C_{0-10}$alkyl or hetaryl-$C_{0-10}$alkyl, any of which is optionaly substituted with one or more independent halo, $-CF_3$, $-OCF_3$, $-OR^{2221}$, $-NR^{2221}R^{3331}$, $-C(O)R^{2221}$, $-CO_2R^{2221}$, $-CONR^{2221}R^{3331}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{2221}$R$^{3331}$, —NR$^{2221}$S(O)$_{\beta a}$R$^{3331}$, —NR$^{2221}$C(=NR$^{3331}$)NR$^{2221a}$R$^{3331a}$, or —OC(=O)NR$^{2221}$R$^{3331}$ substituents.

10. A compound selected from:

5-(3-benzyloxy-2-fluoro-phenyl)-7-cyclobutyl-imidazo[5,1-f][1,2,4]triazin-4-ylamine,
5-(3-Benzyloxy-phenyl)-7-cyclobutyl-imidazo[5,1-f][1,2,4]triazin-4-ylamine,
3-[4-Amino-5-(3-benzyloxy-phenyl)-imidazo[5,1-f][1,2,4]triazin-7-yl]-cyclobutanone,
3-[4-Amino-5-(3-benzyloxy-phenyl)-imidazo[5,1-f][1,2,4]triazin-7-y]-cyclobutanol,
3-[4-Amino-5-(3-benzyloxy-phenyl)-imidazo[5,1-f][1,2,4]triazin-7-yl]-1-methyl-cyclobutanol,
3-[4-Amino-5-(3-benzyloxy-phenyl)-imidazo[5,1-f][1,2,4]triazin-7-yl]-1ethyl-cyclobutanol,
5-(3-Benzyloxy-phenyl)-7-(3-methylamino-cyclobutyl)-imidazo[5,1-f][1,2,4]triazin-4-ylamine,
5-(3-Benzyloxy-phenyl)-7-(3-dimethylamino-cyclobutyl)-imidazo[5,1f][1,2,4]triazin-4-ylamine,
7-(3-Azetidin-1-yl-cyclobutyl)-5-(3-benzyloxy-phenyl)-imidazo[5,1-f][1,2,4]triazin-4-ylamine,
5-(3-Benzyloxy-phenyl)-7-(3-piperidin-1-yl-cyclobutyl)-imidazo[5,1-f][1,2,4]triazin-4-ylamine,
N-{3-[4-Amino-5-(3-benzyloxy-phenyl)-imidazo[5,1-f][1,2,4]triazin-7-yl]-cyclobutyl}-acetamide,
{3-[4-Amino-5-(3-benzyloxy-phenyl)-imidazo[5,1-f][1,2,4]triazin-7-yl]-cyclobutyl}-carbamic acid methyl ester,
1-{3-[4-Amino-5-(3-benzyloxy-phenyl)-imidazo[5,1-f][1,2,4]triazin-7-yl]-cyclobutyl}-3-methyl-urea,
N-{3-[4-Amino-5-(3-benzyloxy-phenyl)-imidazo[5,1-f][1,2,4]triazin-7-yl]-cyclobutyl}-methanesulfonamide,
7-Azetidin-3-yl-5-(3-benzyloxy-phenyl)-imidazo[5,1-f][1,2,4]triazin-4-ylamine,
1-{3-[4-Amino-5-(3-benzyloxy-phenyl)-imidazo[5,1-f][1,2,4]triazin-7-yl]-azetidin-1-yl}-ethanone,
{3-[4-Amino-5-(3-benzyloxy-phenyl)-imidazo[5,1-f][1,2,4]triazin-7-yl]-cyclobutyl}-methanol,
5-(3-Benzyloxy-phenyl)-7-(3-dimethylaminomethyl-cyclobutyl)-imidazo[5,1-f][1,2,4]triazin-4-ylamine,
5-(3-Benzyloxy-phenyl)-7-(3-diethylaminomethyl-cyclobutyl)-imidazo[5,1-f][1,2,4]triazin-4-ylamine,
7-(3-Azetidin-1-ylmethyl-cyclobutyl)-5-(3-benzyloxy-phenyl)-imidazo[5,1-f][1,2,4]triazin-4-ylamine,
5-(3-Benzyloxy-phenyl)-7-(3-piperidin-1-ylmethyl-cyclobutyl)-imidazo[5,1-f][1,2,4]triazin-4-ylamine,
3-[4-Amino-5-(3-benzyloxy-phenyl)-imidazo[5,1-f][1,2,4]triazin-7-yl]-cyclobutanecarboxylic acid amide,
5-(3-Benzyloxy-phenyl)-7-cyclohexyl-imidazo[5,1-f][1,2,4]triazin-4-ylamine,
4-[4-Amino-5-(3-benzyloxy-phenyl)-imidazo[5,1-f][1,2,4]triazin-7-yl]-cyclohexanone,
4-[4-Amino-5-(3-benzyloxy-phenyl)-imidazo[5,1-f][1,2,4]triazin-7-yl]-cyclohexanol,
4-[4-Amino-5-(3-benzyloxy-phenyl)-imidazo[5,1-f][1,2,4]triazin-7-yl]-1-methyl-cyclohexanol,
4-[4-Amino-5-(3-benzyloxy-phenyl)-imidazo[5,1-f][1,2,4]triazin-7-yl]-1-ethyl-cyclohexanol,
4-[4-Amino-5-(3-benzyloxy-phenyl)-imidazo[5,1-f][1,2,4]triazin-7-yl]-cyclohexanecarboxylic acid methyl ester,
4-[4-Amino-5-(3-benzyloxy-phenyl)-imidazo[5,1-f][1,2,4]triazin-7-yl]-cyclohexanecarboxylic acid amide,
4-[4-Amino-5-(3-benzyloxy-phenyl)-imidazo[5,1-f][1,2,4]triazin-7-yl]-cyclohexanecarboxylic acid methylamide,
{4-[4-Amino-5-(3-benzyloxy-phenyl)-imidazo[5,1-f][1,2,4]triazin-7-yl]-cyclohexyl}-methanol,
7-(4-Aminomethyl-cyclohexyl)-5-(3-benzyloxy-phenyl)-imidazo[5,1-f][1,2,4]triazin-4-ylamine,
5-(3-Benzyloxy-phenyl)-7-(4-dimethylaminomethyl-cyclohexyl)-imidazo[5,1-f][1,2,4]triazin-4-ylamine,
7-(4-Azetidin-1-ylmethyl-cyclohexyl)-5-(3-benzyloxy-phenyl)-imidazo[5,1-f][1,2,4]triazin-4-ylamine,
5-(3-Benzyloxy-phenyl)-7-(4-pyrrolidin-1-ylmethyl-cyclohexyl)-imidazo[5,1-f][1,2,4]triazin-4-ylamine,
5-(3-Benzyloxy-phenyl)-7-(4-piperidin-1-ylmethyl-cyclohexyl)-imidazo[5,1-f][1,2,4]triazin-4-ylamine,
5-(3-Benzyloxy-phenyl)-7-piperidin-4-yl-imidazo[5,1-f][1,2,4]triazin-4-ylamine,
1-{4-[4-Amino-5-(3-benzyloxy-phenyl)-imidazo[5,1-f][1,2,4]triazin-7-yl]-piperidin-1-yl}-ethanone,
5-(3-Benzyloxy-phenyl)-7-cyclopentyl-imidazo[5,1-f][1,2,4]triazin-4-ylamine,
3-[4-Amino-5-(3-benzyloxy-phenyl)-imidazo[5,1-f][1,2,4]triazin-7-yl]-cyclopentanecarboxylic acid methyl ester,
3-[4-Amino-5-(3-benzyloxy-phenyl)-imidazo[5,1-f][1,2,4]triazin-7-yl]-cyclopentanecarboxylic acid amide,
3-[4-Amino-5-(3-benzyloxy-phenyl)-imidazo[5,1-f][1,2,4]triazin-7-yl]-cyclopentanecarboxylic acid methylamide,
{3-[4-Amino-5-(3-benzyloxy-phenyl)-imidazo[5,1-f][1,2,4]triazin-7-yl]-cyclopentyl}-methanol,
7-(3-Aminomethyl-cyclopentyl)-5-(3-benzyloxy-phenyl)-imidazo[5,1-f][1,2,4]triazin-4-ylamine,
5(3-Benzyloxy-phenyl)-7-(3-dimethylaminomethyl-cyclopentyl)-imidazo [5,1-f][1,2,4]triazin-4-ylamine,
7-(3-Azetidin-1-ylmethyl-cyclopentyl)-5-(3-benzyloxy-phenyl)-imidazo[5,1-f][1,2,4]triazin-4-ylamine,
5(3-Benzyloxy-phenyl)-7-(3-pyrrolidin-1-ylmethyl-cyclopentyl)-imidazo [5,1-f][1,2,4]triazin-4-ylamine,
5(3-Benzyloxy-phenyl)-7-(3-piperidin-1-ylmethyl-cyclopentyl)-imidazo[5,1-f][1,2,4]triazin-4-ylamine,
N-{3-[4-Amino-5-(3-benzyloxy-phenyl)-imidazo[5,1-f][1,2,4]triazin-7-yl]-cyclopentylmethyl}-acetamide,
{3-[4-Amino-5-(3-benzyloxy-phenyl)-imidazo[5,1-f][1,2,4]triazin-7-yl]-cyclopentylmethyl}-carbamic acid methyl ester,
1-{3-[4-Amino-5-(3-benzyloxy-phenyl)-imidazo [5,1-f][1,2,4]triazin-7-yl]-cyclopentylmethyl}-3-methyl-urea,
3-[4-Amino-5-(3-benzyloxy-phenyl)-imidazo[5,1-f][1,2,4]triazin-7-yl]-cyclopentanone,
3-[4-Amino-5-(3-benzyloxy-phenyl)-imidazo[5,1-f][1,2,4]triazin-7-yl]-cyclopentanol,
7-(3-Amino-cyclopentyl)-5-(3-benzyloxy-phenyl)-imidazo[5,1-f][1,2,4]triazin-4-ylamine,
5(3-Benzyloxy-phenyl)-7-(3-dimethylamino-cyclopentyl)-imidazo[5,1-f][1,2,4]triazin-4-ylamine,
7-(3-Azetidin-1-yl-cyclopentyl)-5-(3-benzyloxy-phenyl)-imidazo [5,1-f][1,2,4]triazin-4-ylamine,
5(3-Benzyloxy-phenyl)-7-(3-pyrrolidin-1-yl-cyclopentyl)-imidazo[5,1-f][1,2,4]triazin-4-ylamine,
5-(3-Benzyloxy-phenyl)-7-(3-piperidin-1-yl-cyclopentyl)-imidazo[5,1-f][1,2,4]triazin-4-ylamine,
5-(3-Benzyloxy-phenyl)-7-phenyl-imidazo[5,1-f][1,2,4]triazin-4-ylamine,
4-[4-Amino-5-(3-benzyloxy-phenyl)-imidazo[5,1-f][1,2,4]triazin-7-yl]-benzoic acid methyl ester, 4-[4-Amino-5-(3-benzyloxy-phenyl)-imidazo[5,1-f][1,2,4]triazin-7-yl]-benzamide,
4-[4-Amino-5-(3-benzyloxy-phenyl)-imidazo[5,1-f][1,2,4]triazin-7-yl]-N-methyl-benzamide,
{4-[4-Amino-5-(3-benzyloxy-phenyl)-imidazo[5,1-f][1,2,4]triazin-7-yl]-phenyl}-methanol,
7-(4-Aminomethyl-phenyl)-5-(3-benzyloxy-phenyl)-imidazo[5,1-f][1,2,4]triazin-4-ylamine,
5-(3-Benzyloxy-phenyl)-7-(4-dimethylaminomethyl-phenyl)-imidazo[5,1-f][1,2,4]triazin-4-ylamine,
N-{4-[4-Amino-5-(3-benzyloxy-phenyl)-imidazo[5,1-f][1,2,4]triazin-7-yl]-benzyl}-acetamide,
{4-[4-Amino-5-(3-benzyloxy-phenyl)-imidazo[5,1-f][1,2,4]triazin-7-yl]-benzyl}-carbamic acid methyl ester,
1-{4-[4-Amino-5-(3-benzyloxy-phenyl)-imidazo[5,1-f][1,2,4]triazin-7-yl]-benzyl}-3-methyl-urea,
5-(3-Benzyloxy-phenyl)-7-(4-dimethylaminomethyl-phenyl)-imidazo[5,1-f][1,2,4]triazin-4-ylamine,
7-(4-Azetidin-1-ylmethyl-phenyl)-5-(3-benzyloxy-phenyl)-imidazo[5,1-f][1,2,4]triazin-4-ylamine,
5-(3-Benzyloxy-phenyl)-7-(4-pyrrolidin-1-ylmethyl-phenyl)-imidazo[5,1-f][1,2,4]triazin-4-ylamine,
5-(3-Benzyloxy-phenyl)-7-(4-piperidin-1-ylmethyl-phenyl)-imidazo[5,1-f][1,2,4]triazin-4-ylamine,
3-[4-Amino-5-(3-benzyloxy-phenyl)-imidazo[5,1-f][1,2,4]triazin-7-yl]-benzoic acid methyl ester,
3-[4-Amino-5-(3-benzyloxy-phenyl)-imidazo[5,1-f][1,2,4]triazin-7-yl]-benzamide,
3-[4-Amino-5-(3-benzyloxy-phenyl)-imidazo[5,1-f][1,2,4]triazin-7-yl]-N-methyl-benzamide,
{3-[4-Amino-5-(3-benzyloxy-phenyl)-imidazo[5,1-f][1,2,4]triazin-7-yl]-phenyl}-methanol,
7-(3-Aminomethyl-phenyl)-5-(3-benzyloxy-phenyl)-imidazo[5,1-f][1,2,4]triazin-4-ylamine,
N-{3-[4-Amino-5-(3-benzyloxy-phenyl)-imidazo[5,1-f][1,2,4]triazin-7-yl]-benzyl}-acetamide,
{3-[4-Amino-5-(3-benzyloxy-phenyl)-imidazo[5,1-f][1,2,4]triazin-7-yl]-benzyl}-carbamic acid methyl ester,
1-{3-[4-Amino-5-(3-benzyloxy-phenyl)-imidazo[5,1-f][1,2,4]triazin-7-yl]-benzyl}-3-methyl-urea,
N-{3-[4-Amino-5-(3-benzyloxy-phenyl)-imidazo[5,1-f][1,2,4]triazin-7-yl]-benzyl}-methanesulfonamide,
5-(3-Benzyloxy-phenyl)-7-(3-dimethylaminomethyl-phenyl)-imidazo[5,1-f][1,2,4]triazin-4-ylamine,
5-(3-Benzyloxy-phenyl)-7-(3-diethylaminomethyl-phenyl)-imidazo[5,1-f][1,2,4]triazin-4-ylamine,
7-(3-Azetidin-1-ylmethyl-phenyl)-5-(3-benzyloxy-phenyl)-imidazo[5,1-f][1,2,4]triazin-4-ylamine,
5-(3-Benzyloxy-phenyl)-7-(3-pyrrolidin-1-ylmethyl-phenyl)-imidazo[5,1-f][1,2,4]triazin-4-ylamine,
5-(3-Benzyloxy-phenyl)-7-(3-piperidin-1-ylmethyl-phenyl)-imidazo[5,1-f][1,2,4]triazin-4-ylamine,
5-(3-Benzyloxy-phenyl)-7-pyridin-4-yl-imidazo[5,1-f][1,2,4]triazin-4-ylamine,
5-(3-Benzyloxy-phenyl)-7-oxazol-2-yl-imidazo[5,1-f][1,2,4]triazin-4-ylamine,
5-(3-Benzyloxy-phenyl)-7-thiophen-3-yl-imidazo[5,1-f][1,2,4]triazin-4-ylamine,
5-(3-Benzyloxy-phenyl)-7-thiophen-2-yl-imidazo[5,1-f][1,2,4]triazin-4-ylamine,
5-(3-Benzyloxy-phenyl)-7-thiazol-5-yl-imidazo[5,1-f][1,2,4]triazin-4-ylamine,
5-(3-Benzyloxy-phenyl)-7-thiazol-2-yl-imidazo[5,1-f][1,2,4]triazin-4-ylamine,
5-(3-Benzyloxy-phenyl)-7-(1H-imidazol-2-yl)-imidazo[5,1-f][1,2,4]triazin-4-ylamine, or 5-(3-Benzyloxy-phenyl)-7-(1H-imidazol-4-yl)-imidazo[5,1-f][1,2,4]triazin-4-ylamine, or a pharmaceutically acceptable salt thereof.

11. A pharmaceutical composition comprising a therapeutically effective amount of a compound of claim 1, or a pharmaceutically acceptable salt thereof, and a pharmaceutically acceptable carrier.

12. A method of treating breast cancer, comprising administering a therapeutically effective amount of a compound of claim 10 or a pharmaceutically acceptable salt thereof to a patient in need thereof.

\* \* \* \* \*

UNITED STATES PATENT AND TRADEMARK OFFICE
CERTIFICATE OF CORRECTION

PATENT NO. : 7,741,324 B2
APPLICATION NO. : 11/185599
DATED : June 22, 2010
INVENTOR(S) : Andrew Philip Crew et al.

Page 1 of 1

It is certified that error appears in the above-identified patent and that said Letters Patent is hereby corrected as shown below:

In the claims, column 97, line 27, replace "$-NR^{21}R^{31}$" with -- $-NR^{21}R^{31}(R^{21a})_{j3}$ --;

In the claims, column 97, line 36, replace "$^{-CONR2221}R^{3331}$," with -- $-CONR^{2221}R^{3331}$ --;

In the claims, column 98, line 39, replace "$-NR^{2221}R^{3331(R2221a)}{}_{j3a}$" with -- $-NR^{2221}R^{3331}(R^{2221a})_{j3a}$ --;

In the claims, column 98, line 43, replace "optionaly" with -- optionally --;

In the claims, column 99, line 5, replace "$R^{41}$, $R^{51}$, $R^{77}$, $R^{77a}$, $R^{87}$, $R^{87a}$, $R^{778}$, and $R^{888}$" with -- $R^{77}$, $R^{77a}$, $R^{87}$, and $R^{87a}$ --; and In the claims, column 99, line 28, replace "aryl-$C_{2-10}$alkenyl aryl-$C_{2-10}$alkynyl" with -- aryl-$C_{2-10}$alkenyl, aryl-$C_{2-10}$alkynyl --.

Signed and Sealed this
Fifteenth Day of March, 2011

David J. Kappos
*Director of the United States Patent and Trademark Office*